United States Patent
Adams et al.

(10) Patent No.: US 8,436,035 B2
(45) Date of Patent: May 7, 2013

(54) ORGANIC COMPOUNDS

(75) Inventors: Christopher Adams, Somerville, MA (US); Qi-Ying Hu, Needham, MA (US); Gary Michael Ksander, Amherst, NH (US); Julien Papillon, Somerville, MA (US)

(73) Assignee: Novartis AG, Basel (CH)

( * ) Notice: Subject to any disclaimer, the term of this patent is extended or adjusted under 35 U.S.C. 154(b) by 979 days.

(21) Appl. No.: 12/519,697

(22) PCT Filed: Dec. 14, 2007

(86) PCT No.: PCT/US2007/025556
§ 371 (c)(1),
(2), (4) Date: Jun. 17, 2009

(87) PCT Pub. No.: WO2008/076336
PCT Pub. Date: Jun. 26, 2008

(65) Prior Publication Data
US 2010/0048562 A1    Feb. 25, 2010

Related U.S. Application Data

(60) Provisional application No. 60/870,499, filed on Dec. 18, 2006.

(51) Int. Cl.
*A61K 31/4174* (2006.01)
*C07D 233/64* (2006.01)

(52) U.S. Cl.
USPC ............... 514/397; 548/311.1; 548/316.4; 514/398

(58) Field of Classification Search ........ 548/311.1, 548/316.4; 514/397, 398
See application file for complete search history.

(56) References Cited

U.S. PATENT DOCUMENTS 4,659,730 A * 4/1987 Hirsch et al. ............ 514/396
5,000,777 A * 3/1991 Szczepanski et al. ........ 504/219

FOREIGN PATENT DOCUMENTS

| EP | 0165780 A | 12/1985 |
|---|---|---|
| WO | 2008/076860 A1 | 6/2008 |
| WO | 2008/076862 A2 | 6/2008 |

OTHER PUBLICATIONS

Ehmer et al. "Development of a test system for inhibitors of human aldosterone synthase (CYP11B2): screening in fission yeast and evaluation of selectivity in V79 cells", J. Steroid Biochemistry & Molecular Biology (2002), 81: 173-179.
Salmon et al., "Plant sterol biosynthesis: novel potent and selective inhibitors of cytochrome P450-dependent obtusifoliol 142-methyl demethylase", Database CA (Online) Chemical Abstracts Service, Columbus, Ohio, US (1992).

* cited by examiner

*Primary Examiner* — Kamal Saeed
*Assistant Examiner* — Janet L Coppins
(74) *Attorney, Agent, or Firm* — Ann R. Pokalsky, Esq.; Dilworth & Barrese, LLP

(57) ABSTRACT

The present invention provides a compound of formula I:

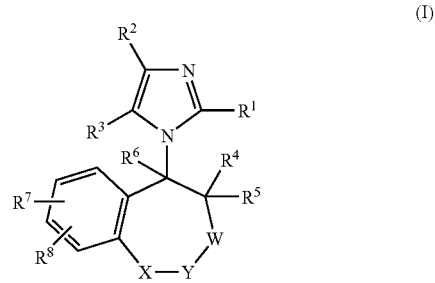

said compound is inhibitor of aldosterone synthase (CYP11B2), and/or 11 beta-hydroxylase (CYP11B1), and/or aromatase, and thus can be employed for the treatment of a disorder or disease mediated by aldosterone synthase, aromatase, or CYP11B1. Accordingly, the compound of formula I can be used in treatment of hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction. Finally, the present invention also provides a pharmaceutical composition.

9 Claims, No Drawings

ORGANIC COMPOUNDS

This application is the National Stage of Application No. PCT/US2007/025556, filed on Dec. 14, 2007, which claims benefit under 35 U.S.C. §119(e) of U.S. Provisional Application No. 60/870,499, filed Dec. 18, 2006, the contents of which are Incorporated herein by reference in their entirety.

The present invention relates to novel imidazole derivatives that are used as aldosterone synthase inhibitors, as well as for treatment of a disorder or disease mediated by aldosterone synthase (CYP11B2) and/or 11-beta-hydroxylase (CYP11B1).

The present invention provides a compound of formula (I):

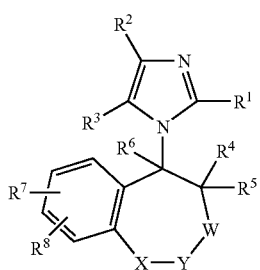

(I)

wherein $R^1$ is hydrogen, halogen, thiol, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^2$ is hydrogen, halogen, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^3$ is hydrogen, methyl, halogen, cyano, ($C_1$-$C_7$) alkenyl, ($C_1$-$C_7$) alkynyl, ($C_1$-$C_7$) alkyl-$SO_2$—, ($C_1$-$C_7$) alkoxy-$SO_2$—, sulfonamido, aryl, heteroaryl, H($R^9$ON=)C—, $R^{10}$O($CH_2$)$_n$—, $R^{11}R^{12}$($R^{13}$O)C—, $R^{14}$O—C(O)— or $R^{15}$—C(O)—, $R^{16}$—C(O)—N($R^{17}$)—; or $R^3$ is ($C_1$-$C_7$) alkyl that is optionally substituted by one to four substituents selected from halogen, mono-($C_1$-$C_7$) alkylamino, di-($C_1$-$C_7$) alkylamino; or $R^2$ and $R^3$ taken together with the carbon atoms to which they are attached optionally form a 5-9 membered ring;

$R^4$ and $R^5$ are independently hydrogen, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl; or $R^4$ and $R^5$ taken together with the carbon atom to which they are attached to optionally form a 3-9 membered ring;

$R^6$ is hydrogen, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^7$ and $R^8$ are independently ($C_1$-$C_7$) alkyl or ($C_3$-$C_7$) cycloalkyl, each of which are optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl; or $R^7$ and $R^8$ are independently hydrogen, halogen, cyano, nitro, mono-($C_1$-$C_7$) alkylamino, di-($C_1$-$C_7$) alkylamino, aryl, heteroaryl, $R^{18}$—O—, $R^{18}$—S—, $R^{19}$—C(O)—, or $R^{19}$—$SO_2$—;

n is 1, 2, 3, or 4;

X is —$R^{20}R^{21}$C—, —C(O)—, —O—, —C(N—$OR^{23}$)—, —C($NR^{23}$)—, —S—, —SO—, —$SO_2$—, or a bond;

W is —$R^{20}R^{21}$C—, —C(O)—, —O—, —$NR^{22}$—C(N—$OR^{23}$)—, —C($NR^{23}$)—, —S—, —SO—, —$SO_2$—, or a bond;

Y is —$R^{20}R^{21}$C—, —C(O)—, —O—, —$NR^{22}$—, —C(N—$OR^{23}$)—, —C($NR^{23}$)—, —S—, —SO—, —$SO_2$—, or a bond; or X-Y is —($R^{22}$)C=C($R^{22}$)—

$R^9$, $R^{10}$, $R^{11}$, $R^{12}$, $R^{13}$, and $R^{16}$ are independently hydrogen, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{14}$ is hydrogen, ($C_1$-$C_7$) alkyl, ($C_3$-$C_7$) cycloalkyl, aryl, heteroaryl, or ($C_3$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{15}$ is hydrogen, ($C_1$-$C_7$) alkyl, amino, mono-($C_1$-$C_7$) alkylamino, di-($C_1$-$C_7$) alkylamino, arylamino, diarylamino, aryl-mono-($C_1$-$C_7$) alkylamino;

$R^{17}$ and $R^{18}$ are independently hydrogen, ($C_1$-$C_7$) alkyl, aryl, or ($C_1$-$C_4$) haloalkyl;

$R^{19}$ is amino, hydroxy, mono-($C_1$-$C_7$) alkylamino, di-($C_1$-$C_7$) alkylamino, ($C_1$-$C_7$) alkoxy, or 5-9 membered heterocyclyl;

$R^{20}$ and $R^{21}$ are independently hydrogen, hydroxy, halogen, $R^{24}R^{25}$N—, ($C_3$-$C_7$) cycloalkyl, aryl, heteroaryl, or ($C_1$-$C_7$) alkyl; said aryl and ($C_1$-$C_7$) alkyl are optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{22}$, $R^{24}$, and $R^{25}$ are independently hydrogen, aryl, heteroaryl, $R^{26}$—$SO_2$—, $R^{27}$—C(O)—, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{23}$, $R^{25}$, $R^{26}$ and $R^{27}$ are independently ($C_1$-$C_7$) alkyl, aryl, heteroaryl or ($C_1$-$C_4$) haloalkyl;

With the proviso that (1) when $R^4$ and $R^5$ are hydrogen and X, Y, and W all are independently —$CH_2$—, or a bond, then $R^3$ is not hydrogen; (2). X, W, and Y cannot simultaneously be a bond; (3) when X is —O— or, then Y is not —C(O)— and W is not —C(O)—; (4). when Y is —O—, then X is not —C(O)— and W is not —C(O)—; (5). when W is —O—, then X is not —C(O)— and Y is not —C(O)—; 6) when Y is $NR^{22}$, then X is not a bond or —C(O)— and/or W is not —C(O)—; (7) when W is $NR^{22}$, then X is not a bond or —C(O)— and/or Y is not —C(O)—; or a pharmaceutically acceptable salt thereof; or an optical isomer thereof; or a mixture of optical isomers.

In one embodiment, the present invention provides the compound of formula (I), wherein $R^1$, $R^2$ and $R^6$ are hydrogen;

$R^3$ is hydrogen, ($C_1$-$C_7$) alkenyl, cyano, $R^{14}$—O—C(O)—, (Ra)(Rb)N—C(O)—, or (Ra)(Rb)N—C(O)—NH—, ($C_6$-$C_{10}$) aryloxy-($C_1$-$C_4$) alkyl, or ($C_1$-$C_7$) alkyl that is optionally substituted by one to four substituents selected from hydroxy, halogen, ($C_1$-$C_7$) alkyl, ($C_1$-$C_7$) alkoxy, ($C_6$-$C_{10}$) aryloxy, 5-7 membered heterocycle, or 5-7 membered heteroaryl;

wherein $R^{14}$ is hydrogen, ($C_1$-$C_7$) alkenyl, cyano, ($C_6$-$C_{10}$) aryl, 5-9 membered heteroaryl, 3-9 membered heterocyclyl, or ($C_1$-$C_7$) alkyl that is optionally substituted by one to three substituents selected from halogen, hydroxy, ($C_1$-$C_7$) alkoxy; Ra and Rb are independently hydrogen, ($C_3$-$C_7$) cycloalkyl, ($C_6$-$C_{10}$) aryl-($C_1$-$C_4$) alkyl, ($C_1$-$C_7$) alkyl, ($C_6$-$C_{10}$) aryl, said each of ($C_1$-$C_7$) alkyl, ($C_6$-$C_{10}$) aryl are optionally substituted by one to two substituents selected from halogen, hydroxy, or ($C_1$-$C_7$) alkyl; or Ra and Rb taken together with the nitrogen to which they are attached, form a 5-9 membered ring represented by the following structures:

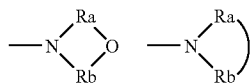

$R^4$ and $R^5$ are independently hydrogen, ($C_1$-$C_7$) alkyl, ($C_6$-$C_{10}$) aryl, ($C_6$-$C_{10}$) aryl-($C_1$-$C_7$) alkyl; or $R^4$ and $R^5$ taken together with the carbon atom to which they attach, form a 3-9 membered ring;

$R^7$ and $R^8$ are independently hydrogen, ($C_1$-$C_7$) alkoxy, ($C_1$-$C_7$) alkyl, nitro, cyano, halogen, 5-7 membered heteroaryl, 5-7 membered heterocyclyl, ($C_3$-$C_7$) cycloalkyl, 5-7 membered heterocyclyl-C(O)—, ($C_6$-$C_{10}$) aryl optionally substituted by one to three substituents selected from halogen, or (Ra')(Rb')N—, wherein Ra' is hydrogen, or ($C_1$-$C_7$) alkyl, Rb' is ($C_1$-$C_7$) alkanoyl, or ($C_1$-$C_7$) alkyl-$SO_2$—; or Ra' and Rb' taken together with the attached nitrogen form a 5-7 membered ring;

X is a bond, and Y and W are independently a bond, —($R^{20}$)($R^{21}$)C—, —C(O)—, —C(N—O$R^{23}$)—, —S—, —SO—$SO_2$—, —O—, —N(($C_1$-$C_4$) alkyl)-, —N(($C_1$-$C_4$) alkoxy)-, —N(($C_6$-$C_{10}$) aryloxy)-, wherein $R^{20}$ and $R^{21}$ are independently hydrogen, hydroxy, halogen, ($C_1$-$C_7$) alkoxy, ($C_5$-$C_{10}$) aryl that is optionally substituted by one to two ($C_1$-$C_4$) alkoxy groups; or ($C_1$-$C_7$) alkyl that is optionally substituted by one or two halogen atoms; or $R^{20}$ and $R^{21}$ are (Rc)(Rd)N—, wherein Rc and Rd are independently hydrogen, ($C_1$-$C_7$) alkyl, ($C_3$-$C_7$) cycloalkyl, ($C_6$-$C_{10}$) aryl-($C_1$-$C_4$) alkyl; $R^{23}$ is ($C_1$-$C_7$) alkyl, or ($C_6$-$C_{10}$) aryl; or $R^{20}$ and $R^{21}$ taken together with the attached carbon atom form a 3-7 membered cycloalkylidene; With the proviso that (1) when $R^4$ and $R^5$ are hydrogen and X, Y, and W are independently —$CH_2$—, or a bond, then $R^3$ is not hydrogen; (2). X, W, and Y cannot simultaneously be a bond; (3) when X is —O— or, then Y is not —C(O)— and W is not —C(O)—; (4). when Y is —O—, then X is not —C(O)— and W is not —C(O)—; (5). when W is —O—, then X is not —C(O)— and Y is not —C(O)—; 6) when Y is $NR^{22}$, then X is not a bond or —C(O)— and/or W is not —C(O)—; (7) when W is $NR^{22}$, then X is not a bond or —C(O)— and/or Y is not —C(O)—; or a pharmaceutically acceptable salt thereof; or an optical isomer thereof; or a mixture of optical isomers.

In another embodiment, the present invention provides the compound of formula (I), wherein $R^1$, $R^2$, $R^6$ and $R^7$ are hydrogen; $R^3$ is ($C_1$-$C_7$) alkyl-O—C(O)—, pyrrolidine-carbonyl, ($C_1$-$C_4$) alkyl substituted by one or two substituents selected from hydroxy, ($C_1$-$C_4$) alkoxy, halogen; or $R^3$ is Ra'-NH—C(O)—, wherein Ra' is ($C_6$-$C_{10}$) aryl-($C_1$-$C_4$) alkyl, or ($C_6$-$C_{10}$) aryl substituted by one or two halogen atoms; R4 and R5 are independently hydrogen, ($C_1$-$C_7$) alkyl; $R^7$ and $R^8$ are independently hydrogen, nitro, cyano, ($C_1$-$C_7$) alkanoyl-NH—, ($C_1$-$C_7$) alkyl, halogen, ($C_1$-$C_7$) alkoxy; X, Y and W are independently a bond, —$CH_2$—, —C(O)—, —C(=N—O—($C_1$-$C_7$) alkyl)-, —CHF—, —$CF_2$—, —S—, —SO—, or —O—; or a pharmaceutically acceptable salt thereof; or an optical isomer thereof; or a mixture of optical isomers.

In another embodiment, the present invention provides the compound of formula (I), wherein, $R^1$, $R^2$, $R^4$, $R^5$, $R^6$ and $R^7$ are hydrogen; $R^3$ is ($C_1$-$C_4$) alkyl-O—C(O)—; $R^8$ is ($C_1$-$C_7$) alkanoyl-NH—; X and Y are —$CH_2$—, W is a bond; or a pharmaceutically acceptable salt thereof; or an optical isomer thereof; or a mixture of optical isomers.

In another embodiment, the present invention provides the compound of formula (I), wherein, $R^1$, $R^2$, $R^6$, $R^7$ and $R^8$ are hydrogen; $R^3$ is ($C_1$-$C_4$) alky-O—C(O)—; $R^4$ and $R^5$ are ($C_1$-$C_4$) alkyl, X is —CHF—, Y is —$CH_2$—, W is a bond; or a pharmaceutically acceptable salt thereof; or an optical isomer thereof; or a mixture of optical isomers.

In another embodiment, the present invention provides the compound of formula (I), wherein, $R^1$, $R^2$, $R^6$, $R^7$ and $R^8$ are hydrogen; $R^3$ is ($C_1$-$C_4$) alky-O—C(O)—; $R^4$ and $R^5$ are ($C_1$-$C_4$) alkyl, X is —$CH_2$—, Y and W are a bond; or a pharmaceutically acceptable salt thereof; or an optical isomer thereof; or a mixture of optical isomers.

In another embodiment, the present invention provides the compound of formula (I), wherein, $R^1$, $R^2$, $R^6$, $R^7$ and $R^8$ are hydrogen; $R^3$ is Ra'-NH—C(O)—, wherein Ra' is ($C_6$-$C_{10}$) aryl-($C_1$-$C_4$) alkyl, or ($C_6$-$C_{10}$) aryl substituted by one or two halogen atoms; or $R^3$ is ($C_1$-$C_4$) alkyl substituted by one or two substituents selected from hydroxy, ($C_1$-$C_4$) alkoxy; $R^4$ and $R^5$ are ($C_1$-$C_4$) alkyl, X is —CHF—, Y is —$CH_2$—, W is a bond; or a pharmaceutically acceptable salt thereof; or an optical isomer thereof; or a mixture of optical isomers.

In another embodiment, the present invention provides the compound of formula (I), wherein, $R^1$, $R^2$, $R^6$, $R^7$ and $R^8$ are hydrogen; $R^3$ is ($C_1$-$C_4$) alkyl substituted by one or two substituents selected from hydroxy, halogen; $R^4$ and $R^5$ are ($C_1$-$C_4$) alkyl, X is —$CF_2$—, Y and W are a bond; or a pharmaceutically acceptable salt thereof; or an optical isomer thereof; or a mixture of optical isomers.

In another embodiment, the present invention provides the compound of formula (I), wherein, $R^1$, $R^2$, $R^4$, $R^5$, $R^6$, $R^7$ and $R^8$ are hydrogen; $R^3$ is ($C_1$-$C_4$) alkyl-O—C(O)—; X, Y and W are —CH$_2$—; or a pharmaceutically acceptable salt thereof; or an optical isomer thereof; or a mixture of optical isomers.

In another embodiment, the present invention provides the compound of formula (I), wherein, R$^1$, R$^2$, R$^6$, R$^7$ and R$^8$ are hydrogen; R$^3$ is hydrogen, (C$_1$-C$_4$) alkenyl, or (C$_1$-C$_4$) alkyl optionally substituted by one or two hydroxy groups or halogen atoms; R$^4$ and R$^5$ are (C$_1$-C$_4$) alkyl; X is —C(O)—, —S—, —SO$_2$—, —O—, —C(=N—(C$_1$-C$_4$) alkoxy)-, or —(R$^{20}$)(R$^{21}$)C—, wherein R$^{20}$ and R$^{21}$ are independently hydrogen, hydroxy, (C$_1$-C$_4$) alkyl, (C$_1$-C$_4$) alkoxy, or (C$_5$-C$_7$) aryl substituted by one to two (C$_1$-C$_4$) alkoxy groups; Y is —CH$_2$—, or a bond; W is a bond; or a pharmaceutically acceptable salt thereof; or an optical isomer thereof; or a mixture of optical isomers.

In another embodiment, the present invention provides the compound of formula (I), wherein, R$^1$, R$^2$, R$^4$, R$^5$, R$^6$, R$^7$ and R$^8$ are hydrogen; R$^3$ is (C$_1$-C$_4$) alkyl-O—C(O)—, or Rx-NH—, wherein Rx is (C$_3$-C$_7$) cycloalkyl-NH—, or 5-7 membered heterocyclyl; R$^8$ is cyano, 5-7 membered heteroaryl, (C$_3$-C$_7$) cycloalkyl, 5-7 membered heterocyclyl-C(O)—, or (C$_6$-C$_7$) aryl substituted by one to two halogen atoms; R$^8$ is (Ra')(Rb')N—, wherein Ra' is (C$_1$-C$_4$) alkyl, hydrogen, Rb' is (C$_1$-C$_4$) alkyl-SO$_2$—; X and Y are —CH$_2$—, W is a bond; or a pharmaceutically acceptable salt thereof; or an optical isomer thereof; or a mixture of optical isomers.

In another embodiment, the present invention provides the compound of formula (I), wherein, R$^1$, R$^2$, R$^6$, R$^7$ and R$^8$ are hydrogen; R$^3$ is CH$_3$—O—C(O)—; R$^4$ and R$^5$ are (C$_1$-C$_4$) alkyl; X is —(R$^{20}$)CH—, where R$^{20}$ is Rc-NH—, or (C$_6$-C$_7$) aryl optionally substituted by one to two (C$_1$-C$_4$) alkoxy groups, wherein Rc is (C$_5$-C$_7$) aryl-(C$_1$-C$_4$) alkyl; Y is —CH$_2$—; W is a bond; or a pharmaceutically acceptable salt thereof; or an optical isomer thereof; or a mixture of optical isomers.

In another embodiment, the present invention provides the compound of formula (I), wherein, R$^1$, R$^2$, R$^4$, R$^5$, R$^6$, R$^7$ and R$^8$ are hydrogen; R$^3$ is (C$_6$-C$_7$) aryloxy-(C$_1$-C$_4$) alkyl-; X is —CH$_2$—, Y is —S—, W is a bond; or a pharmaceutically acceptable salt thereof; or an optical isomer thereof; or a mixture of optical isomers.

In another embodiment, the present invention provides the compound of formula (I), wherein, R$^1$, R$^2$, R$^6$ and R$^7$ are hydrogen; R$^3$ is CH$_3$—O—C(O)—, 5-7 membered heterocyclyl-O—C(O)—, (C$_1$-C$_4$) alkenyl, (C$_1$-C$_4$) alky optionally substituted by one to two hydroxy groups or (C$_1$-C$_4$) alkoxy groups; R$^4$ and R$^5$ are independently hydrogen, (C$_1$-C$_4$) alkyl, or (C$_6$-C$_7$) aryl; R$_8$ is hydrogen, halogen, or cyano; X is —(R$^{20}$)(R$^{21}$)C—, wherein R$^{20}$ and R$^{21}$ are independently hydrogen, or (C$_1$-C$_4$) alkyl; Y and W are a bond; or a pharmaceutically acceptable salt thereof; or an optical isomer thereof; or a mixture of optical isomers.

In another embodiment, the present invention provides the compound of formula (I), wherein, R$^1$, R$^2$, R$^6$, R$^7$ and R$^8$ are hydrogen; R$^3$ is hydrogen, or (C$_1$-C$_4$) alkyl optionally substituted by one or two hydroxy groups or halogen atoms; R$^4$ and R$^5$ are (C$_1$-C$_4$) alkyl; X is —C(O)—, —O—, or —(R$^{20}$)(R$^{21}$) C—, wherein R$^{20}$ and R$^{21}$ are independently hydrogen, (C$_1$-C$_4$) alkyl; Y and W are a bond; or a pharmaceutically acceptable salt thereof; or an optical isomer thereof; or a mixture of optical isomers.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it can be referred to as an alkenyl (double bond) or an alkynyl (triple bond) group.

The term "aryl" refers to monocyclic or bicyclic aromatic hydrocarbon groups having 6-20 carbon atoms in the ring portion. Preferably, the aryl is a (C$_6$-C$_{10}$) aryl. Non-limiting examples include phenyl, biphenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—aryl-S—, nitro, cyano, carboxy, alkyl-O—C(O)—, carbamoyl, alkyl-S(O)—, sulfonyl, sulfonamido, heterocyclyl and the like, wherein R is independently hydrogen, alkyl, aryl, heteroaryl, aryl-alkyl-, heteroaryl-alkyl- and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 14 carbons.

As used herein, the term "acyl" refers to a group R—C (O)— of from 1 to 10 carbon atoms of a straight, branched, or cyclic configuration or a combination thereof, attached to the parent structure through carbonyl functionality. Such group can be saturated or unsaturated, and aliphatic or aromatic. Preferably, R in the acyl residue is alkyl, or alkoxy, or aryl, or heteroaryl. Also preferably, one or more carbons in the acyl residue may be replaced by nitrogen, oxygen or sulfur as long as the point of attachment to the parent remains at the carbonyl. Examples include but are not limited to, acetyl, benzoyl, propionyl, isobutyryl, t-butoxycarbonyl, benzyloxycarbonyl and the like. Lower acyl refers to acyl containing one to four carbons.

As used herein, the term "acylamino" refers to acyl-NH—, wherein "acyl" is defined herein.

As used herein, the term "alkanoyl" refers to alkyl-C(O)—, wherein alkyl is defined herein.

As used herein, the term "carbamoyl" refers to H$_2$NC (O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonyl" refers to R—SO$_2$—, wherein R is hydrogen, alkyl, aryl, hereoaryl, aryl-alkyl, heteroaryl-alkyl, aryl-O—, heteroaryl-O—, alkoxy, aryloxy, cycloalkyl, or heterocyclyl.

As used herein, the term "sulfonamido" refers to alkyl-S (O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S (O)$_2$—N(alkyl)-, heteroaryl-S(O)$_2$—N(alkyl)-, heteroaryl-alkyl-S(O)$_2$—N(alkyl)- and the like.

As used herein, the term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1, 4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" further refers to heterocyclic groups as defined herein substituted with 1, 2 or 3 substituents selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxy;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to optionally substituted saturated or unsaturated monocyclic, bicyclic or tricyclic hydrocarbon groups of 3-12 carbon atoms, each of which may be substituted by one or more substituents, such as alkyl, halo, oxo, hydroxy, alkoxy, alkyl-C(O)—, acylamino, carbamoyl, alkyl-NH—, (alkyl)$_2$N—, thiol, alkylthio, nitro, cyano, carboxy, alkyl-O—C(O)—, sulfonyl, sulfonamido, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

As used herein, the term "aryloxy" refers to both an —O-aryl and an —O— heteroaryl group, wherein aryl and heteroaryl are defined herein.

As used herein, the term "heteroaryl" refers to a 5-14 membered monocyclic- or bicyclic- or fused polycyclic-ring system, having 1 to 8 heteroatoms selected from N, O or S. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halogen" or "halo" refers to fluoro, chloro, bromo, and iodo.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences*, 20th ed., Mack Publishing Company, Easton, Pa., (1985), which is herein incorporated by reference.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by aldosterone synthase, or (ii) associated with aldosterone synthase activity, or (iii) characterized by abnormal activity of aldosterone synthase; or (2) reducing or inhibiting the activity of aldosterone synthase; or (3) reducing or inhibiting the expression of aldosterone synthase. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of aldosterone synthase; or at least partially reducing or inhibiting the expression of aldosterone synthase.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary*, (W.B. Saunders Co. 27th ed. 1988).

As used herein, the term "inhibition" or "inhibiting" refers to the reduction or suppression of a given condition, symptom, or disorder, or disease, or a significant decrease in the baseline activity of a biological activity or process. Preferably, the condition or symptom or disorder or disease is mediated by aldosterone synthase activity. More preferably, the condition or symptom or disorder or disease is associated with the abnormal activity of aldosterone synthase or the abnormal biological activity of aldosterone synthase, or the condition or symptom or disorder or disease is associated with the abnormal expression of aldosterone synthase.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "abnormal" refers to an activity or feature which differs from a normal activity or feature.

As used herein, the term "abnormal activity" refers to an activity which differs from the activity of the wild-type or native gene or protein, or which differs from the activity of the gene or protein in a healthy subject. The abnormal activity can be stronger or weaker than the normal activity. In one embodiment, the "abnormal activity" includes the abnormal (either over- or under-) production of mRNA transcribed from a gene. In another embodiment, the "abnormal activity" includes the abnormal (either over- or under-) production of polypeptide from a gene. In another embodiment, the abnormal activity refers to a level of a mRNA or polypeptide that is different from a normal level of said mRNA or polypeptide by about 15%, about 25%, about 35%, about 50%, about 65%, about 85%, about 100% or greater. Preferably, the abnormal level of the mRNA or polypeptide can be either higher or lower than the normal level of said mRNA or polypeptide. Yet in another embodiment, the abnormal activity refers to functional activity of a protein that is different from a normal activity of the wild-type protein. Preferably, the abnormal activity can be stronger or weaker than the normal activity. Preferably, the abnormal activity is due to the mutations in the corresponding gene, and the mutations can be in the coding region of the gene or non-coding regions such as transcriptional promoter regions. The mutations can be substitutions, deletions, insertions.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illustrate the invention and does not pose a limitation on the scope of the invention otherwise claimed. No language in the specification should be construed as indicating any non-claimed element essential to the practice of the invention.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans-(E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the present invention are either obtained in the free form, as a salt thereof, or as prodrug derivatives thereof.

When a basic group is present in the compounds of the present invention, the compounds can be converted into acid addition salts thereof, in particular, acid addition salts with the imidazolyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$)alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$)alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds are inactive or have low activity compared to the corresponding active drug compound, that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

2. Reductive reactions, such as reduction of carbonyl groups, reduction of alcoholic groups and carbon-carbon double bonds, reduction of nitrogen-containing functions groups, and other reduction reactions.

3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, application Ser. No. 10/656, 838, incorporated herein by reference. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxy groups with lipophilic carboxylic acids, or of carboxylic acid groups with alcohols, e.g., aliphatic alcohols. Wermuth, *The Practice of Medicinal Chemistry*, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties. The compounds of the present invention are useful as aldosterone synthase inhibitors. Aldosterone synthase (CYP11B2) is a mitcohondrial cytochrome P450 enzyme catalyzing the last step of aldosterone production in the adrenal cortex, i.e., the conversion of 11-deoxycorticosterone to aldosterone. Aldosterone synthase has been demonstrated to be expressed in all cardiovascular tissues such as heart, umbilical cord, mesenteric and pulmonary arteries, aorta, endothelium and vascular cells. Moreover, the expression of aldosterone synthase is closely correlated with aldosterone production in cells. It has been observed that elevations of aldosterone activities or aldosterone levels induce different diseases such as congestive heart failure, cardiac or myocardial fibrosis, renal failure, hypertension, ventricular arrhythmia and other adverse effects, etc., and that the inhibition of aldosterone or aldosterone synthase would be useful therapeutic approaches. See e.g., Ulmschenider et al. "Development and evaluation of a pharmacophore model for inhibitors of aldosterone synthase (CYP11B2)," *Bioorganic & Medicinal Chemistry Letters*, 16: 25-30 (2006); Bureik et al., "Development of test systems for the discovery of selective human aldosterone synthase (CYP11B2) and 11β-hydroxylase (CYP11B1) inhibitors, discovery of a new lead compound for the therapy of congestive heart failure, myocardial fibrosis and hypertension," *Moleculare and Cellular Endocrinology*, 217: 249-254 (2004); Bos et al., "Inhibition of catechnolamine-induced cardiac fibrosis by an aldosteron antagonist," *J. Cardiovascular Pharmacol*, 45(1): 8-13 (2005); Jaber and Madias, "Progression of chronic kidney disease: can it be prevented or arrested?" *Am. J. Med.* 118(12): 1323-1330 (2005); Khan and Movahed, "The role of aldosterone and aldosterone-receptor antagonists in heart failure," *Rev. Cardiovasc Med.*, 5(2): 71-81 (2004); Struthers, "Aldosterone in heart failure: pathophysiology and treatment," *Cyrr. Heart Fail.*, 1(4): 171-175 (2004); Harris and Rangan, "Retardation of kidney failure—applying principles to practice," *Ann. Acad. Med. Singapore*, 34(1): 16-23 (2005); Arima, "Aldosterone and the kidney: rapid regulation of renal microcirculation," *Steroids*, online publication November 2005; Brown, "Aldosterone and end-organ damage," *Curr. Opin. Nephrol Hypertens*, 14:235-241 (2005); Grandi, "Antihypertensive therapy: role of aldosteron antagonists," *Curr. Pharmaceutical Design*, 11: 2235-2242 (2005); Declayre and Swynghedauw, "Molecular mechanisms of myocardial remodeling: the role of aldosterone," *J. Mol. Cell. Cardiol.*, 34: 1577-1584 (2002). Accordingly, the compounds of the present invention as aldosterone synthase inhibitors, are also useful for treatment of a disorder or disease mediated by aldosterone synthase or responsive to inhibition of aldosterone synthase. In particular, the compounds of the present invention as aldosterone synthase inhibitors are useful for treatment of a disorder or disease characterized by abnormal aldosterone synthase activity. Preferably, the compounds of the present invention are also useful for treatment of a disorder or disease selected from hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, inflammation, increased formation of collagen, fibrosis such as cardiac or myocardial fibrosis and remodeling following hypertension and endothelial dysfunction.

Furthermore, the compounds of the present invention are useful as CYP11B1 (11-β-hydroxylase) inhibitors. CYP11B1 catalyzes the last steps of cortisol synthesis. Cortisol is the main glucocorticoid in human. It regulates energy mobilization and thus the stress response. In addition, it is involved in the immune response of the human body. Abnormally increased cortisol level is the cause of a variety of diseases including Cushing's syndrome. Accordingly, the compounds of the present invention as CYP11B1 inhibitors are also useful for the treatment of a disorder or a disease or a condition characterized by abnormal activity or abnormal level of CYP11B1. The compounds of the present invention can be used for the treatment of a disorder, a disease or a condition such as Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

Additionally, the present invention provides:
a compound of the present invention for use as a medicament;
the use of a compound of the present invention for the preparation of a pharmaceutical composition for the delay of progression and/or treatment of a disorder or disease mediated by aldosterone synthase, or characterized by abnormal activity of aldosterone synthase, or by abnormal expression of aldosterone synthase.
the use of a compound of the present invention for the preparation of a pharmaceutical composition for the delay of progression and/or treatment of a disorder or disease selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

Additionally, the present invention provides:
a compound of the present invention for use as a medicament;
the use of a compound of the present invention for the preparation of a pharmaceutical composition for the delay of progression and/or treatment of a disorder or disease or condition mediated by CYP11B1, or characterized by abnormal activity of CYP11B1, or by abnormal expression/level of CYP11B1.
the use of a compound of the present invention for the preparation of a pharmaceutical composition for the delay of progression and/or treatment of a disorder or disease or condition selected from Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

The compounds of formula (I) can be prepared by the procedures described in the following sections.

Generally, the compounds of formula (I) can be prepared according to Scheme A, which contains three steps.

Scheme A:

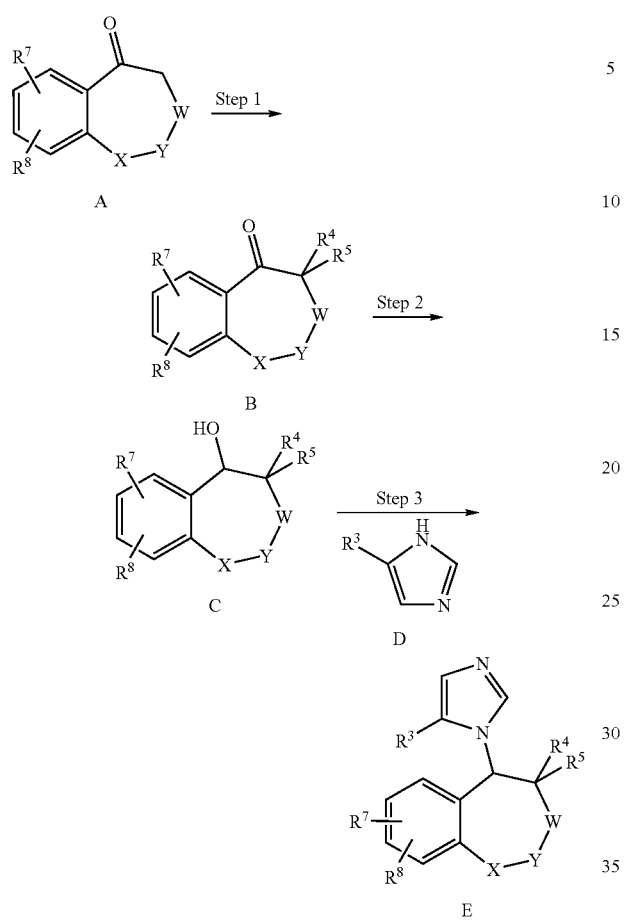

In step one ketones of type A can undergo alkylation by deprotonation with a non-nucleophilic strong base, preferably sodium hydride. Subsequent treatment with an alkyl halide, for example, iodomethane affords compounds of type B. Manipulation of the equivalents of base and alkyl halide permits mono- or di-alkylation. Alternatively, one can forgo Step 1 and proceed to Step 2 directly ($R^4$ & $R^5$=H). Compounds of type B can undergo reduction to alcohols of type C upon treatment with an appropriate hydride source, preferably sodium borohydride. Mitsunobu-type reactions of alcohols C with imidazole derivatives (D), in the presence of triphenylphosphine and an appropriate azodicarboxylate, for example diisopropyl azodicarboxylate yield compounds of type E.

Alternatively, the compounds of formula (I) can be prepared according to Schemes 1-10 in the following sections.

Scheme 1:

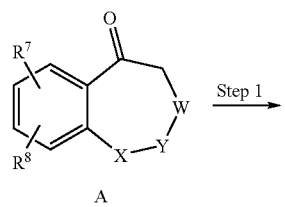

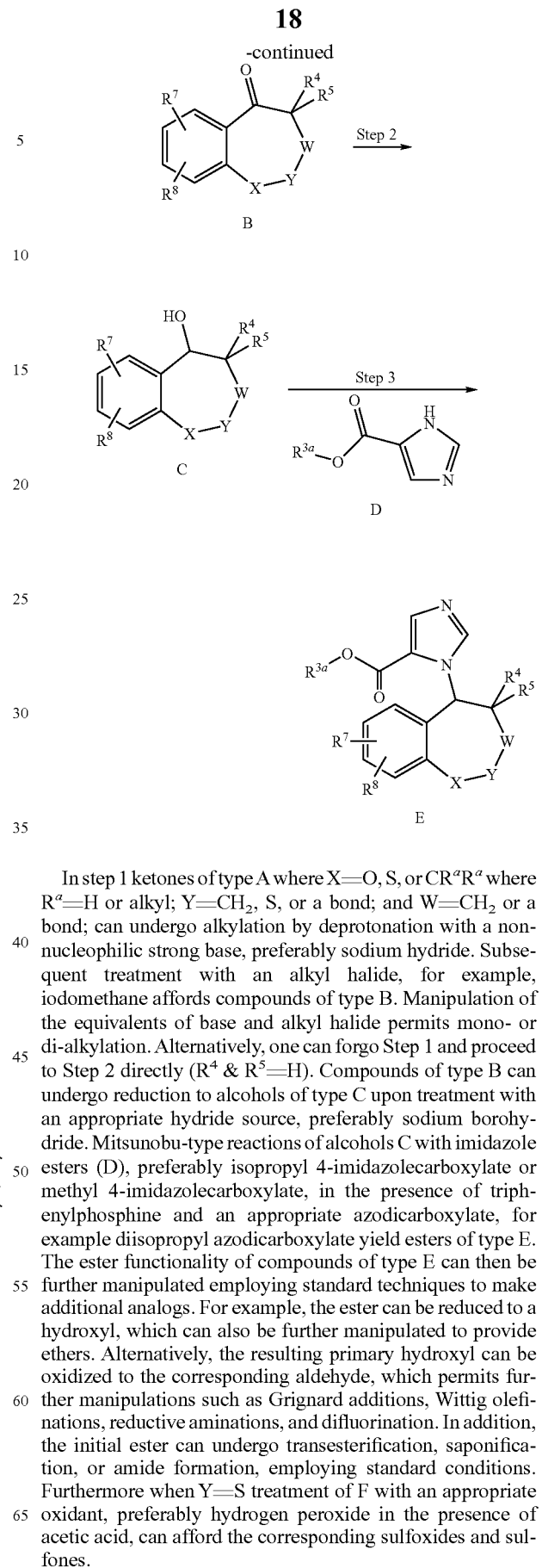

In step 1 ketones of type A where X=O, S, or $CR^aR^a$ where $R^a$=H or alkyl; Y=$CH_2$, S, or a bond; and W=$CH_2$ or a bond; can undergo alkylation by deprotonation with a non-nucleophilic strong base, preferably sodium hydride. Subsequent treatment with an alkyl halide, for example, iodomethane affords compounds of type B. Manipulation of the equivalents of base and alkyl halide permits mono- or di-alkylation. Alternatively, one can forgo Step 1 and proceed to Step 2 directly ($R^4$ & $R^5$=H). Compounds of type B can undergo reduction to alcohols of type C upon treatment with an appropriate hydride source, preferably sodium borohydride. Mitsunobu-type reactions of alcohols C with imidazole esters (D), preferably isopropyl 4-imidazolecarboxylate or methyl 4-imidazolecarboxylate, in the presence of triphenylphosphine and an appropriate azodicarboxylate, for example diisopropyl azodicarboxylate yield esters of type E. The ester functionality of compounds of type E can then be further manipulated employing standard techniques to make additional analogs. For example, the ester can be reduced to a hydroxyl, which can also be further manipulated to provide ethers. Alternatively, the resulting primary hydroxyl can be oxidized to the corresponding aldehyde, which permits further manipulations such as Grignard additions, Wittig olefinations, reductive aminations, and difluorination. In addition, the initial ester can undergo transesterification, saponification, or amide formation, employing standard conditions. Furthermore when Y=S treatment of F with an appropriate oxidant, preferably hydrogen peroxide in the presence of acetic acid, can afford the corresponding sulfoxides and sulfones.

Scheme 2:

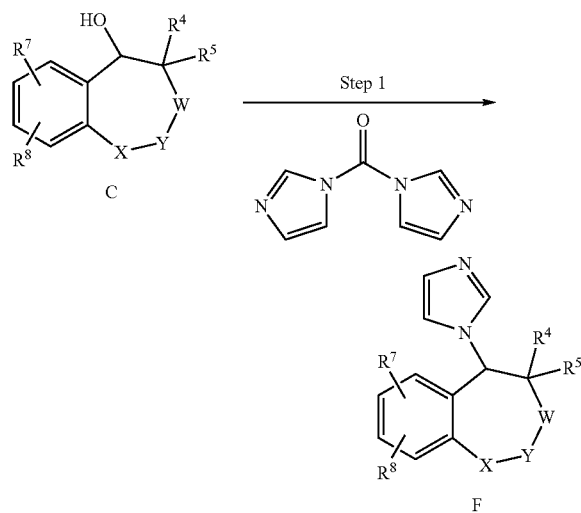

In step 1 alcohols of type C are treated with 1,1'-carbonyldiimidazole in acetonitrile at reflux to furnish mono-substituted imidazoles of type F.

Scheme 3:

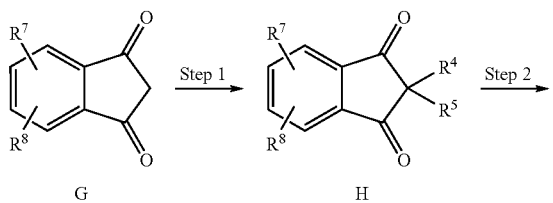

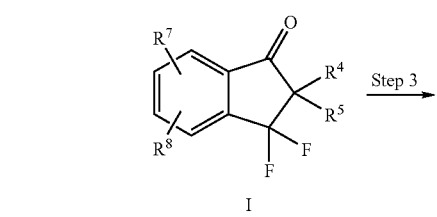

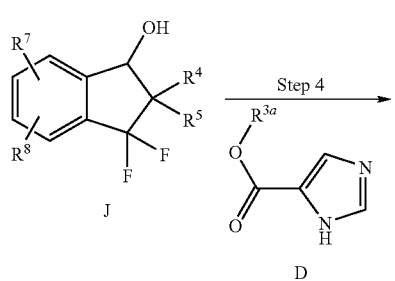

In Step 1, di-ketones of type G undergo alkylation upon action of a non-nucleophilic base, preferably potassium fluoride absorbed on Celite®, and an alkyl halide, preferably iodomethane to afford compounds of type H. Step 2 involves di-fluorination of one of the carbonyls via the employment of a suitable fluorinating reagent, preferably (diethylamino)sulfur trifluoride (DAST) in an appropriate solvent, preferably chlorobenzene, in the presence of an alcohol catalyst, preferably ethanol, at reflux to deliver I. Compounds of type I undergo reduction to alcohols of type J (Step 3) upon treatment with an appropriate hydride source, preferably sodium borohydride. Mitsunobu-type reaction of alcohols J with imidazole esters (D) in the presence of triphenylphosphine and an appropriate azodicarboxylate, for example, di-t-butyl azodicarboxylate yields esters of type K. The ester functionality of compounds of type K can then be further manipulated employing standard techniques to make additional analogs. For example, the ester can be reduced to a hydroxyl, which can also be further manipulated to provide ethers. Alternatively, the resulting primary hydroxyl can be oxidized to the corresponding aldehyde, which permits further manipulations such as Grignard additions, Wittig olefinations, reductive aminations, and difluorination. In addition, the initial ester can undergo transesterification, saponification, or amide formation, employing standard conditions.

Scheme 4:

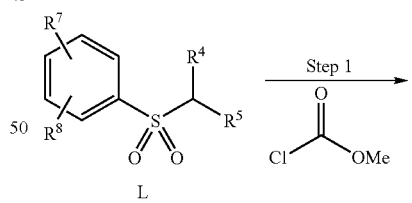

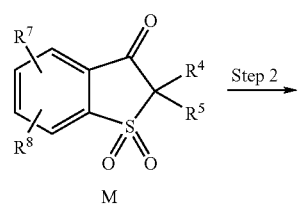

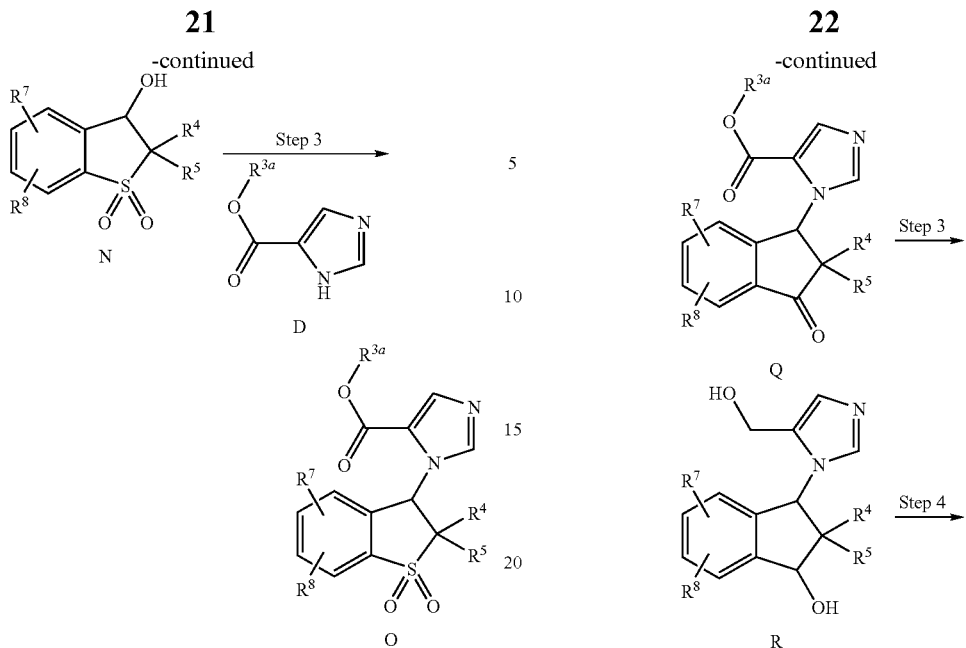

In step 1 phenyl sulfones of type L undergo di-lithiation via treatment with an appropriate organolithium reagent, preferably n-butyl lithium. The resultant dianion is trapped with methyl chloroformate to afford keto-sulfone M. Step 2 involves the reduction of the ketone with an appropriate hydride source, preferably sodium borohydride to furnish alcohols of type N. Mitsunobu-type reaction of alcohols N with imidazole esters (D) in the presence of triphenylphosphine and an appropriate azodicarboxylate, for example, di-t-butyl azodicarboxylate yields esters O. The ester functionality of compounds of type O can then be further manipulated employing standard techniques to make additional analogs. For example, the ester can be reduced to a hydroxyl, which can also be further manipulated to provide ethers. Alternatively, the resulting primary hydroxyl can be oxidized to the corresponding aldehyde, which permits further manipulations such as Grignard additions, Wittig olefinations, reductive aminations, and difluorination. In addition, the initial ester can undergo transesterification, saponification, or amide formation, employing standard conditions.

Scheme 5:

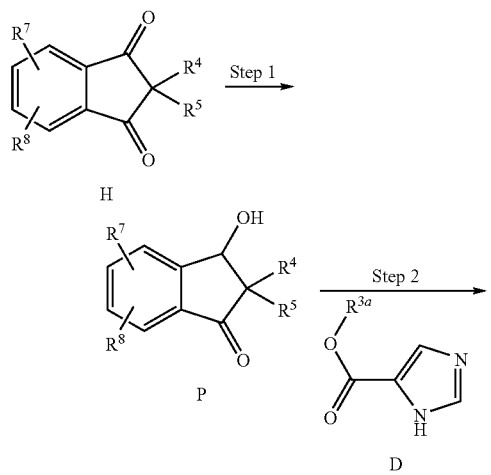

Beginning from compound H (Scheme 3), mono-reduction employing the appropriate source and equivalents of hydride, preferably, 0.3 equivalents of sodium borohydride, furnishes alcohols of type P. Mitsunobu-type reaction of alcohols P with imidazole esters (D) in the presence of triphenylphosphine and an appropriate azodicarboxylate, for example, di-t-butyl azodicarboxylate, yields esters of type Q (Step 2). The ester functionality of compounds of type Q can then be further manipulated employing standard techniques to make additional analogs. For example the ester can undergo transesterification, saponification, or amide formation, employing standard conditions. In addition, treatment of compounds of type Q with various hydroxylamines and amines under standard condensation conditions permits conversion of the ketone functionality to oxime and imine analogs. Alternatively, the esters of type Q, can undergo bis-reduction of the ester and ketone functionalities (Step 3) via employment of the appropriate hydride source, preferably lithium aluminum hydride. Step 4 involves the chemoselective protection of the resulting primary hydroxyl via employment of an appropriate protecting group, preferably t-butyldimethylsilyl ether via employment of t-butyldimethylsilyl chloride in the presence of imidazole. The resulting alcohol, S, can then be oxidized, preferably with manganese(IV) oxide to provide ketones of type T. Step 6 involves the deprotection of the primary hydroxyl, preferably via treatment with hydrochloric acid in dioxane to furnish compounds of type U. Alternatively, ketones of type U can be treated with various hydroxylamines and amines under standard condensation conditions followed by deprotection, preferably employing tetrabutylammonium fluoride to permit access to oxime and imine analogs of U. In addition the primary hydroxyl of compounds of type U can then be further manipulated employing standard techniques to make additional analogs. For example, the hydroxyl can be alkylated to provide ethers. Furthermore the hydroxyl can be oxidized to the corresponding aldehyde, which permits further manipulations such as Grignard additions, Wittig olefinations, reductive aminations, and difluorination.

Scheme 6

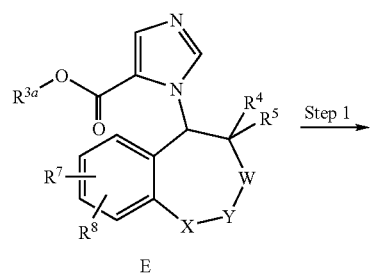

E

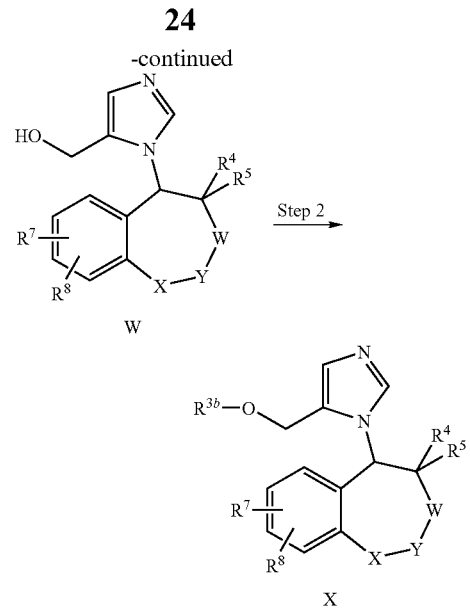

In step 1 esters of type E can be treated with a source of hydride, preferably LiAlH$_4$, to furnish alcohols of type W. If so desired, the resulting hydroxyls can then be further manipulated employing standard techniques to make additional analogs; for example, in Step 2 the hydroxyl can be deprotonated with the appropriate base, preferably NaH, and treated with alkyl halides to provide ethers of type X.

Scheme 8

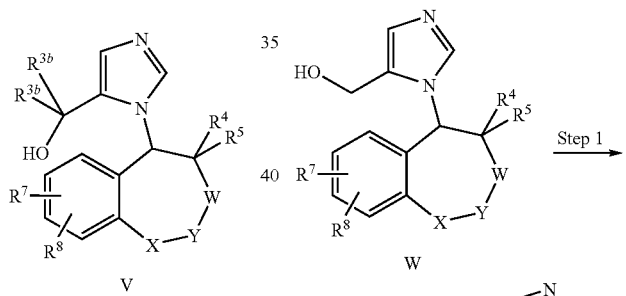

Compounds of type E can be treated with an excess of Grignard reagent, preferably short chain alkylmagnesium halides to afford alcohols of type V. In addition the hydroxyl of compounds of type V can then be further manipulated employing standard techniques to make additional analogs; for example, the hydroxyl can be alkylated to provide ethers.

Scheme 7

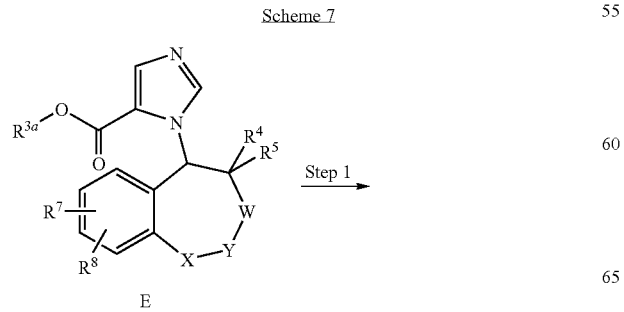

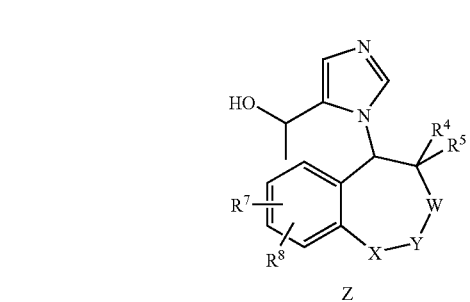

In step 1 alcohols of type W (Scheme 7) can be oxidized to aldehydes of type Y, via employment of a suitable oxidant, preferably manganese (IV) oxide. Upon treatment with Grignard reagents, preferably, short chain alkylmagnesium halides, aldehydes of type Y can be converted to secondary alcohols of type Z. In addition, the hydroxyl of compounds of type Z can then be further manipulated employing standard techniques to make additional analogs; for example, the hydroxyl can be alkylated to provide ethers.

Scheme 9

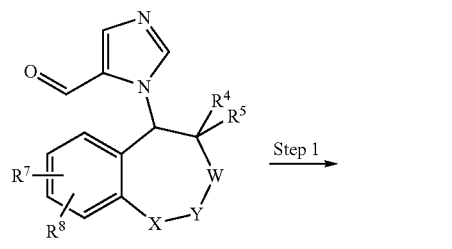

Y

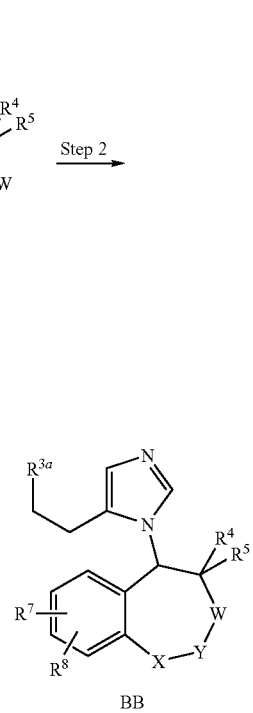

In Step 1 aldehydes of type Y can undergo olefinations, preferably by employing the Wittig reaction and common variations thereof, as described in Marynoff, B. E.; Reitz, Al. B. *Chemical Reviews*, 1989, 89, 863-927, to provide olefins of type AA. If so desired the olefins generated in step 1 can undergo hydrogenation (Step 2), preferably by employing palladium on carbon and a hydrogen atmosphere to furnish compounds of type BB.

Scheme 10

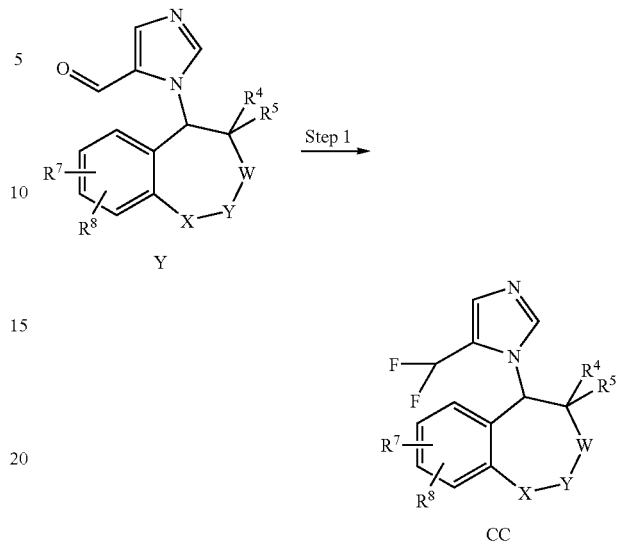

Aldehydes of type Y can be converted to the corresponding difluoro derivatives (CC) upon treatment with a fluorinating agent, preferably (diethylamino)sulfur trifluoride (DAST) at elevated temperatures.

Generally, enantiomers of the compounds of the present invention can be prepared by methods known to those skilled in the art to resolve racemic mixtures, such as by formation and recrystallization of diastereomeric salts or by chiral chromatography or HPLC separation utilizing chiral stationery phases.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxy groups are those that can be converted under mild conditions into free amino thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Preferably, the pharmaceutical compositions are tablets and gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical compositions contain a therapeutically effective amount of a compound of the invention as defined above, either alone or in a combination with one or more therapeutic agents, e.g., each at an effective therapeutic dose as reported in the art. Such therapeutic agents include at least one or two or more selected from the following groups:

(i) angiotensin II receptor antagonist or a pharmaceutically acceptable salt thereof, (ii) HMG-Co-A reductase inhibitor or a pharmaceutically acceptable salt thereof, (iii) angiotensin converting enzyme (ACE) Inhibitor or a pharmaceutically acceptable salt thereof, (iv) calcium channel blocker (CCB) or a pharmaceutically acceptable salt thereof, (v) dual angiotensin converting enzyme/neutral endopeptidase (ACE/NEP) inhibitor or a pharmaceutically acceptable salt thereof, (vi) endothelin antagonist or a pharmaceutically acceptable salt thereof, (vii) renin inhibitor or a pharmaceutically acceptable salt thereof, (viii) diuretic or a pharmaceutically acceptable salt thereof, (ix) an ApoA-I mimic;

(x) an anti-diabetic agent;

(xi) an obesity-reducing agent;

(xii) an aldosterone receptor blocker;

(xiii) an endothelin receptor blocker;

(xiv) a CETP inhibitor;

(xv) an inhibitor of Na-K-ATPase membrane pump;

(xvi) a beta-adrenergic receptor blocker or an alpha-adrenergic receptor blocker;

(xvii) a neutral endopeptidase (NEP) inhibitor; and (xviii) an inotropic agent.

An angiotensin II receptor antagonist or a pharmaceutically acceptable salt thereof is understood to be an active ingredients which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

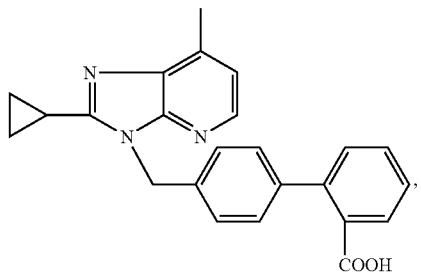 [SMILES: Cc1ccnc2c1nc(C1CC1)n2Cc1ccc(-c2ccccc2C(=O)O)cc1]

the compound with the designation SC-52458 of the following formula

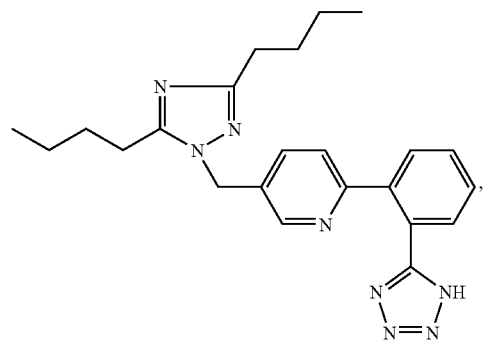 [SMILES: CCCCc1nc(CCCC)n(Cc2ccc(-c3ccccc3-c3nnn[nH]3)nc2)n1]

and the compound with the designation ZD-8731 of the following formula

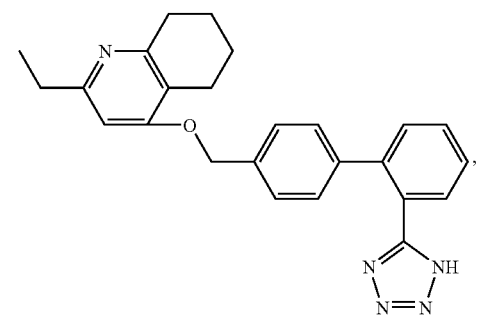 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are those agents which have been marketed, most preferred is valsartan or a pharmaceutically acceptable salt thereof.

HMG-Co-A reductase inhibitors (also called beta-hydroxy-beta-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is atorvastatin, fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

A preferred dual angiotensin converting enzyme/neutral endopetidase (ACE/NEP) inhibitor is, for example, omapatrilate (cf. EP 629627), fasidotril or fasidotrilate, or, if appropriable, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

Suitable renin inhibitors include compounds having different structural features. For example, mention may be made of compounds which are selected from the group consisting of ditekiren (chemical name: [1S-[1R*,2R*,4R*(1R*,2R*)]]-1-[(1,1-dimethylethoxy)carbonyl]-L-proly l-L-phenylalanyl-N-[2-hydroxy-5-methyl-1-(2-methylpropyl)-4-[[[2-methyl-1-[[(2-pyridinylmrthyl)amino]carbonyl]butyl]amino] carbonyl]hexyl]-N-alfa-methyl-L-histidinamide); terlakiren (chemical name: [R—(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), preferably, in each case, the hydrochloride salt thereof, SPP630, SPP635 and SPP800 as developed by Speedel.

Preferred renin inhibitor of the present invention include RO 66-1132 and RO 66-1168 of formula (A) and (B)

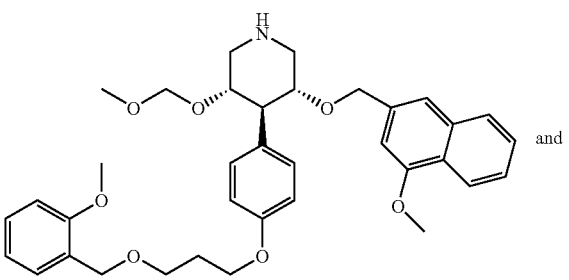

(A)

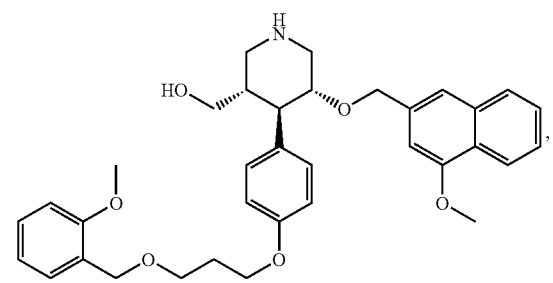

(B)

respectively, or a pharmaceutically acceptable salt thereof.

In particular, the present invention relates to a renin inhibitor which is a δ-amino-γ-hydroxy-ω-aryl-alkanoic acid amide derivative of the formula (C)

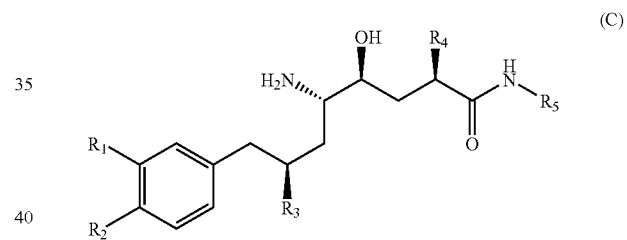

(C)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-6}$alkyl; and $R_5$ is cycloalkyl, $C_{1-6}$alkyl, $C_{1-6}$hydroxyalkyl, $C_{1-6}$alkoxy-$C_{1-6}$alkyl, $C_{1-6}$alkanoyloxy-$C_{1-6}$alkyl, $C_{1-6}$-aminoalkyl, $C_{1-6}$alkylamino-$C_{1-6}$alkyl, $C_{1-6}$dialkylamino-$C_{1-6}$alkyl, $C_{1-6}$alkanoylamino-$C_{1-6}$-alkyl, HO(O)C—$C_{1-6}$alkyl, $C_{1-6}$alkyl-O—(O)C—$C_{1-6}$alkyl, $H_2N$—C(O)—$C_{1-6}$alkyl, $C_{1-6}$alkyl-HN—C(O)—$C_{1-6}$alkyl or $(C_{1-6}$alkyl$)_2$N—C(O)—$C_{1-6}$alkyl; or a pharmaceutically acceptable salt thereof.

As an alkyl, $R_1$ may be linear or branched and preferably comprise 1 to 6 C atoms, especially 1 or 4 C atoms. Examples are methyl, ethyl, n- and i-propyl, n-, i- and t-butyl, pentyl and hexyl.

As a halogenalkyl, $R_1$ may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

As an alkoxy, $R_1$ and $R_2$ may be linear or branched and preferably comprise 1 to 4 C atoms. Examples are methoxy, ethoxy, n- and i-propyloxy, n-, i- and t-butyloxy, pentyloxy and hexyloxy.

As an alkoxyalkyl, $R_1$ may be linear or branched. The alkoxy group preferably comprises 1 to 4 and especially 1 or 2 C atoms, and the alkyl group preferably comprises 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxypropyl, 4-ethoxybutyl, 5-ethoxypentyl, 6-ethoxyhexyl, propyloxymethyl, butyloxymethyl, 2-propyloxyethyl and 2-butyloxyethyl.

As a $C_{1-6}$alkoxy-$C_{1-6}$alkyloxy, $R_1$ may be linear or branched. The alkoxy group preferably comprises 1 to 4 and especially 1 or 2 C atoms, and the alkyloxy group preferably comprises 1 to 4 C atoms. Examples are methoxymethyloxy, 2-methoxyethyloxy, 3-methoxypropyloxy, 4-methoxybutyloxy, 5-methoxypentyloxy, 6-methoxyhexyloxy, ethoxymethyloxy, 2-ethoxyethyloxy, 3-ethoxypropyloxy, 4-ethoxybutyloxy, 5-ethoxypentyloxy, 6-ethoxyhexyloxy, propyloxymethyloxy, butyloxymethyloxy, 2-propyloxyethyloxy and 2-butyloxyethyloxy.

In a preferred embodiment, $R_1$ is methoxy- or ethoxy-$C_{1-4}$alkyloxy, and $R_2$ is preferably methoxy or ethoxy. Particularly preferred are compounds of formula (III), wherein $R_1$ is 3-methoxypropyloxy and $R_2$ is methoxy.

As a branched alkyl, $R_3$ and $R_4$ preferably comprise 3 to 6° C. atoms. Examples are i-propyl, i- and t-butyl, and branched isomers of pentyl and hexyl. In a preferred embodiment, $R_3$ and $R_4$ in compounds of formula (C) are in each case i-propyl.

As a cycloalkyl, $R_5$ may preferably comprise 3 to 8 ring-carbon atoms, 3 or 5 being especially preferred. Some examples are cyclopropyl, cyclobutyl, cyclopentyl, cyclohexyl and cyclooctyl. The cycloalkyl may optionally be substituted by one or more substituents, such as alkyl, halo, oxo, hydroxy, alkoxy, amino, alkylamino, dialkylamino, thiol, alkylthio, nitro, cyano, heterocyclyl and the like.

As an alkyl, $R_5$ may be linear or branched in the form of alkyl and preferably comprise 1 to 6 C atoms. Examples of alkyl are listed herein above. Methyl, ethyl, n- and i-propyl, n-, i- and t-butyl are preferred.

As a $C_{1-6}$hydroxyalkyl, $R_5$ may be linear or branched and preferably comprise 2 to 6 C atoms. Some examples are 2-hydroxyethyl, 2-hydroxypropyl, 3-hydroxypropyl, 2-, 3 or 4-hydroxybutyl, hydroxypentyl and hydroxyhexyl.

As a $C_{1-6}$alkoxy-$C_{1-6}$alkyl, $R_5$ may be linear or branched. The alkoxy group preferably comprises 1 to 4 C atoms and the alkyl group preferably 2 to 4 C atoms. Some examples are 2-methoxyethyl, 2-methoxypropyl, 3-methoxypropyl, 2-, 3- or 4-methoxybutyl, 2-ethoxyethyl, 2-ethoxypropyl, 3-ethoxypropyl, and 2-, 3- or 4-ethoxybutyl.

As a $C_{1-6}$alkanoyloxy-$C_{1-6}$alkyl, $R_5$ may be linear or branched. The alkanoyloxy group preferably comprises 1 to 4 C atoms and the alkyl group preferably 2 to 4 C atoms. Some examples are formyloxymethyl, formyloxyethyl, acetyloxyethyl, propionyloxyethyl and butyroyloxyethyl.

As a $C_{1-6}$aminoalkyl, $R_5$ may be linear or branched and preferably comprise 2 to 4 C atoms. Some examples are 2-aminoethyl, 2- or 3-aminopropyl and 2-, 3- or 4-aminobutyl.

As $C_{1-6}$alkylamino-$C_{1-6}$alkyl and $C_{1-6}$dialkylamino-$C_{1-6}$alkyl, $R_5$ may be linear or branched. The alkylamino group preferably comprises $C_{1-6}$alkyl groups and the alkyl group has preferably 2 to 4 C atoms. Some examples are 2-methylaminoethyl, 2-dimethylaminoethyl, 2-ethylaminoethyl, 2-ethylaminoethyl, 3-methylaminopropyl, 3-dimethylaminopropyl, 4-methylaminobutyl and 4-dimethylaminobutyl.

As a HO(O)C—$C_{1-6}$alkyl, $R_5$ may be linear or branched and the alkyl group preferably comprises 2 to 4 C atoms. Some examples are carboxymethyl, carboxyethyl, carboxypropyl and carboxybutyl.

As a $C_{1-6}$alkyl-O—(O)C—$C_{1-6}$alkyl, $R_5$ may be linear or branched, and the alkyl groups preferably comprise independently of one another 1 to 4 C atoms. Some examples are methoxycarbonylmethyl, 2-methoxycarbonylethyl, 3-methoxycarbonylpropyl, 4-methoxy-carbonylbutyl, ethoxycarbonylmethyl, 2-ethoxycarbonylethyl, 3-ethoxycarbonylpropyl, and 4-ethoxycarbonylbutyl.

As a $H_2N$—C(O)—$C_{1-6}$alkyl, $R_5$ may be linear or branched, and the alkyl group preferably comprises 2 to 6 C atoms. Some examples are carbamidomethyl, 2-carbamidoethyl, 2-carbamido-2,2-dimethylethyl, 2- or 3-carbamidopropyl, 2-, 3- or 4-carbamidobutyl, 3-carbamido-2-methylpropyl, 3-carbamido-1,2-dimethylpropyl, 3-carbamido-3-ethylpropyl, 3-carbamido-2,2-dimethylpropyl, 2-, 3-, 4- or 5-carbamidopentyl, 4-carbamido-3,3- or -2,2-dimethylbutyl. Preferably, $R_5$ is 2-carbamido-2,2-dimethylethyl.

Accordingly, preferred are δ-amino-γ-hydroxy-ω-aryl-alkanoic acid amide derivatives of formula (C) having the formula

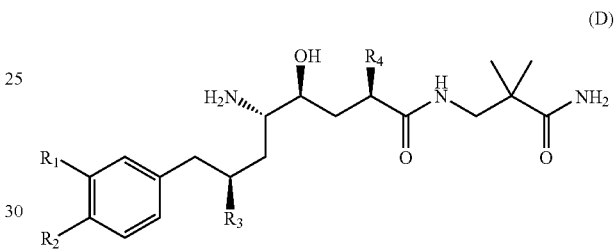

(D)

wherein $R_1$ is 3-methoxypropyloxy; $R_2$ is methoxy; and $R_3$ and $R_4$ are isopropyl; or a pharmaceutically acceptable salt thereof; chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide, also known as aliskiren.

The term "aliskiren", if not defined specifically, is to be understood both as the free base and as a salt thereof, especially a pharmaceutically acceptable salt thereof, most preferably a hemi-fumarate salt thereof.

A diuretic is, for example, a thiazide derivative selected from the group consisting of chlorothiazide, hydrochlorothiazide, methylclothiazide, and chlorothalidon. The most preferred is hydrochlorothiazide.

An ApoA-I mimic is, for example, D4F peptide, especially of formula D-W-F-K-A-F-Y-D-K-V-A-E-K-F-K-E-A-F An anti-diabetic agents include insulin secretion enhancers which are active ingredients that have the property to promote the secretion of insulin from pancreatic β-cells. Examples of insulin secretion enhancers are a biguanide derivative, for example, metformin or, if appropriate, a pharmaceutically acceptable salt thereof, especially the hydrochloride thereof. Other insulin secretion enhancers include sulfonylureas (SU), especially those which promote the secretion of insulin from pancreatic β-cells by transmitting signals of insulin secretion via SU receptors in the cell membrane, including (but are not limited to) tolbutamide; chlorpropamide; tolazamide; acetohexamide; 4-chloro-N-[(1-pyrrolidinylamino)carbonyl]-benzensulfonamide (glycopyramide); glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; and tolylcyclamide, or pharmaceutically acceptable salts thereof.

Insulin secretion enhancers furthermore include short-acting insulin secretion enhancers, such as the phenylalanine derivative nateglinide [N-(trans-4-isopropylcyclohexyl-carbonyl)-D-phenylalanine] (cf. EP 196222 and EP 526171) of the formula

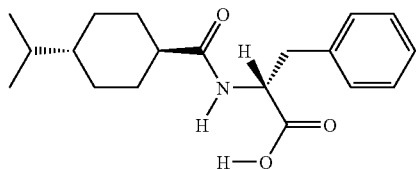 [SMILES: CC(C)[C@H]1CC[C@H](C(=O)N[C@H](Cc2ccccc2)C(=O)O)CC1]

and repaglinide [(S)-2-ethoxy-4-{2-[[3-methyl-1-[2-(1-piperidinyl)phenyl]butyl]amino]-2-oxoethyl}benzoic acid]. Repaglinide is disclosed in EP 589874, EP 147850 A2, in particular Example 11 on page 61, and EP 207331 A1. It can be administered in the form as it is marketed, e.g. under the trademark NovoNorm™; calcium (2S)-2-benzyl-3-(cis-hexahydro-2-isoindolinlycarbonyl)-propionate dihydrate (mitiglinide-cf. EP 507534); furthermore representatives of the new generation of SUs such as glimepiride (cf. EP 31058); in free or pharmaceutically acceptable salt form. The term nateglinide likewise comprises crystal modifications such as disclosed in EP 0526171 B1 or U.S. Pat. No. 5,488,510, respectively, the subject matter of which, especially with respect to the identification, manufacture and characterization of crystal modifications, is herewith incorporated by reference to this application, especially the subject matter of claims 8 to 10 of said U.S. patent (referring to H-form crystal modification) as well as the corresponding references to the B-type crystal modification in EP 196222 B1 the subject matter of which, especially with respect to the identification, manufacture and characterization of the B-form crystal modification. Preferably, in the present invention, the B- or H-type, more preferably the H-type, is used. Nateglinide can be administered in the form as it is marketed e.g. under the trademark STARLIX™.

Insulin secretion enhancers likewise include the long-acting insulin secretion enhancer DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is a insulinotropic proteine which was described, e.g., by W. E. Schmidt et al. in *Diabetologia,* 28, 1985, 704-707 and in U.S. Pat. No. 5,705,483.

The term "GLP-1 agonists" used herein means variants and analogs of GLP-1(7-36)$NH_2$ which are disclosed in particular in U.S. Pat. Nos. 5,120,712, 5,118,666, 5,512,549, WO 91/11457 and by C. Orskov et al in J. Biol. Chem. 264 (1989) 12826. The term "GLP-1 agonists" comprises especially compounds like GLP-1(7-37), in which compound the carboxy-terminal amide functionality of $Arg^{36}$ is displaced with Gly at the $37^{th}$ position of the GLP-1(7-36)$NH_2$ molecule and variants and analogs thereof including $GLN^9$-GLP-1(7-37), D-$GLN^9$-GLP-1(7-37), acetyl $LYS^9$-GLP-1(7-37), $LYS^{18}$-GLP-1(7-37) and, in particular, GLP-1(7-37)OH, $VAL^8$-GLP-1(7-37), $GLY^8$-GLP-1(7-37), $THR^8$-GLP-1(7-37), $MET^8$-GLP-1(7-37) and 4-imidazopropionyl-GLP-1. Special preference is also given to the GLP agonist analog exendin-4, described by Greig et al in Diabetologia 1999, 42, 45-50.

An insulin sensitivity enhancer restores impaired insulin receptor function to reduce insulin resistance and consequently enhance the insulin sensitivity.

An appropriate insulin sensitivity enhancer is, for example, an appropriate hypoglycemic thiazolidinedione derivative (glitazone).

An appropriate glitazone is, for example, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297). Preferred are pioglitazone, rosiglitazone and troglitazone.

Other anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; and $α_2$-adrenergic antagonists; in which the active ingredients are present in each case in free form or in the form of a pharmaceutically acceptable salt.

An obesity-reducing agent includes lipase inhibitors such as orlistat and appetite suppressants such as sibutramine, phentermine.

An aldosteron receptor blocker includes spironolactone and eplerenone.

An endothelin receptor blocker includes bosentan, etc.

A CETP inhibitor refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). The CETP inhibitors include those disclosed in U.S. Pat. No. 6,140,343 and U.S. Pat. No. 6,197,786. CETP inhibitors disclosed in these patents include compounds, such as [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, which is also known as torcetrapib. CETP inhibitors are also described in U.S. Pat. No. 6,723,752, which includes a number of CETP inhibitors including (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol. CETP inhibitors also include those described in U.S. patent application Ser. No. 10/807,838 filed Mar. 23, 2004. U.S. Pat. No. 5,512,548 discloses certain polypeptide derivatives having activity as CETP inhibitors, also certain CETP-inhibitory rosenonolactone derivatives and phosphate-containing analogs of cholesteryl ester are disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO2000/017165, WO2005/095409 and WO2005/097806.

A Na_K-ATPase inhibitor can be used to inhibit the Na and K exchange across the cell membranes. Such inhibitor can be for example digoxin.

A beta-adrenergic receptor blocker includes but is not limited to: esmolol especially the hydrochloride thereof; acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or U.S. Pat. No. 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., Journal of Medicinal Chemistry, 1982, 25, 670; epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Helv. Chim. Acta, 1971, 54, 241; metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,7691; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., *Journal of Medicinal Chemistry*, 1966, 9, 88; sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824.

An alpha-adrenergic receptor blocker includes but is not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol, which may be prepared as disclosed above; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art.

The natriuretic peptides constitute a family of peptides that include the atrial (ANP), brain-derived (BNP) and C-type natriuretic (CNP) peptides. The natriuretic peptides effect vasodilation, natriuresis, diuresis, decreased aldosterone release, decreased cell growth, and inhibition of the sympathetic nervous system and the renin-angiotensin-aldosterone system indicating their involvement in the regulation of blood pressure and of sodium and water balance. Neutral endopeptidase 24.11 (NEP) inhibitors impede degradation of natriuretic peptides and elicit pharmacological actions potentially beneficial in the management of several cardiovascular disorders. A NEP inhibitor useful in the said combination is an agent selected from the group represented by candoxatril, sinorphan, SCH 34826 and SCH 42495.

An inotropic agent is selected from the group consisting of: digoxin, digitoxin, digitalis, dobutamine, dopamine, epinephrine, milrinone, amrinone and norepinephrine, etc.

A compound of the present invention may be administered either simultaneously, before or after the other active ingredient, either separately by the same or different route of administration or together in the same pharmaceutical formulation.

Furthermore, the combinations as described above can be administered to a subject via simultaneous, separate or sequential administration (use). Simultaneous administration (use) can take place in the form of one fixed combination with two or three or more active ingredients, or by simultaneously administering two or three or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two, or three or more compounds are administered such that no overlap of measurable blood levels of both compounds are present in an overlapping manner (at the same time).

Also combinations of two or three or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Additionally, the present invention provides:
a pharmaceutical composition or combination of the present invention for use as a medicament;
the use of a pharmaceutical composition or combination of the present invention for the delay of progression and/or treatment of a disorder or disease mediated by or associated with aldosterone synthase, or responsive to inhibition of aldosterone synthase, or characterized by abnormal activity or expression of aldosterone synthase.
the use of a pharmaceutical composition or combination of the present invention for the delay of progression and/or treatment of a disorder or disease mediated by or associated with CYP11B1, or responsive to inhibition of CYP11B1, or characterized by abnormal activity or expression of CYP11B1.
the use of a pharmaceutical composition or combination of the present invention for the delay of progression and/or treatment of a disorder or disease selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.
the use of a pharmaceutical composition or combination of the present invention for the preparation of a pharmaceutical composition for the delay of progression and/or treatment of a disorder or disease or condition selected from Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

The pharmaceutical composition or combination of the present invention can be in unit dosage of about 1-1000 mg of active ingredients for a subject of about 50-70 kg, preferably about 1-500 mg, or 1-250 mg, or 1-200 mg, or 1-100 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, intraarterially, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, preferably between about 0.1-100 mg/kg.

The activities of a compound according to the present invention can be assessed by the following in vitro & in vivo methods well-described in the art. See Fieber, A et al. (2005), "Aldosterone Synthase Inhibitor Ameliorates Angiotensin II—Induced Organ Damage," *Circulation*, 111:3087-3094. The reference cited herein is incorporated by reference in its entirety.

In particular, the aldosterone synthase inhibitory activities in vitro can be determined by the following assay.

Human adrenocortical carcinoma NCI-H295R cell line is obtained from American Type Culture Collection (Manassas, Va.). Insulin/transferrin/selenium (ITS)-A supplement (100×), DMEM/F-12, antibiotic/antimycotic (100×), and fetal calf serum (FCS) are purchased from Gibco (Grand Island, N.Y.). Anti-mouse PVT scintillation proximity assay (SPA) beads and NBS 96-well plates are obtained from Amersham (Piscataway, N.J.) and Corning (Acton, Mass.), respectively. Solid black 96-well flat bottom plates were purchased from Costar (Corning, N.Y.). Aldosterone and angiotensin (Ang II) are purchased from Sigma (St. Louis, Mo.). D-[1,2, 6,7-$^3$H(N)]aldosterone was acquired from PerkinElmer (Boston, Mass.). Nu-serum was a product of BD Biosciences (Franklin Lakes, N.J.).

For in vitro measurement of aldosterone activity, human adrenocortical carcinoma NCI-H295R cells are seeded in NBS 96-well plates at a density of 25,000 cells/well in 100 µl of a growth medium containing DMEM/F12 supplemented with 10% FCS, 2.5% Nu-serum, 1 µg ITS/ml, and 1× antibiotic/antimycotic. The medium is changed after culturing for 3 days at 37° C. under an atmosphere of 5% $CO_2$/95% air. On the following day, cells are rinsed with 100 μl of DMEM/F12 and incubated with 100 μl of treatment medium containing 1 μM Ang II and a compound at different concentrations in quadruplicate wells at 37° C. for 24 hr. At the end of incubation, 50 μl of medium is withdrawn from each well for measurement of aldosterone production by an RIA using mouse anti-aldosterone monoclonal antibodies.

Measurement of aldosterone activity can also be performed using a 96-well plate format. Each test sample is incubated with 0.02 μCi of D-[1,2,6,7-$^3$H(N)]aldosterone and 0.3 μg of anti-aldosterone antibody in phosphate-buffered saline (PBS) containing 0.1% Triton X-100, 0.1% bovine serum albumin, and 12% glycerol in a total volume of 200 μl at room temperature for 1 hr. Anti-mouse PVT SPA beads (50 μl) are then added to each well and incubated overnight at room temperature prior to counting in a Microbeta plate counter. The amount of aldosterone in each sample is calculated by comparing with a standard curve generated using known quantities of the hormone.

The in vivo inhibitory activities for aldosterone synthase can be determined by the following assay.

Test compounds (i.e., potential aldosterone synthase inhibitors) are profiled in vivo in a conscious rat model of acute secondary hyperaldosteronism. Wild-type rats are instrumented with chronically indwelling arterial and venous cannulas, which are exteriorized through a tether/swivel system. The ambulatory rats are housed in specialized cages to allow blood sampling and parenteral drug administration without disturbing the animals. Angiotensin II is continuously infused intravenously at a level sufficient to elevate plasma aldosterone concentration (PAC) by ~200-fold to 1-5 nM. This PAC increase is sustained at a stable level for at least 8-9 hours. Test compounds are administered p.o. (via oral gavage) or parenterally (via the arterial catheter) after one hour of angiotensin II infusion at a time when PAC has increased to a steady-state level. Arterial blood samples are collected before and at various times (up to 24 hours) after test agent administration for later determination of PAC and concentration of test agent. From these measurements, various parameters can be derived, e.g., 1) onset and duration of PAC reduction by the test agent, 2) pharmacokinetic parameters of the test agent such as half-life, clearance, volume of distribution, and oral bioavailability, 3) dose/PAC response, dose/test-agent concentration, and test-agent concentration/PAC response relationships, and 4) dose- and concentration-potencies and efficacy of the test agent. A successful test compound decreases PAC in a dose- and time-dependent fashion in the dose range of about 0.01 to about 10 mg/kg i.a. or p.o.

The in vitro inhibitory activities for CYP11B1 can be determined by the following assay.

The cell line NCI-H295R was originally isolated from an adrenocortical carcinoma and has been characterized in the literature through the stimulable secretion of steroid hormones and the presence of the enzymes essential for steroidogenesis. Thus, the NCI-H295R cells have Cyp11 B1 (steroid 11 p-hydroxylase). The cells show the physiological property of zonally undifferentiated human foetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbeoco's Modified Eagle'Ham F-12 Medium (DME/F12), which has been I supplemented with Ulroser SF Serum (Soprachem, Cergy-Saint-Christophe, France), insulin, transferrin, selenite (I-T-S, Becton Dickinson Biosciences, Franklin lakes, NJ, USA) and antibiotics in 75 $cm^2$ cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum instead of Ultroser SF for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin 11 (1D or 100 nanomolar), potassium ions (16 millimolar), forskolin (10 micromolar) or a combination of two stimulants.

The excretion of aldosterone, cortisol, corticosterone and estradiol/estrone into the culture medium can be detected and quantified by commercially available, specific monoclonal antibodies in radioimmunoassays in accordance with the manufacturer's instructions.

Inhibition of the release of certain steroids can be used as a measure of the respective enzyme inhibition by the added test compounds. The dose-dependent inhibition of enzymic activity by a compound is calculated by means of an inhibition plot which is characterized by an IC50.

The IC50 values for active test compounds are ascertained by a simple linear regression analysis in order to construct inhibition plots without data weighting. The inhibition plot is calculated by fting a 4-parameter logistic function to the raw data points using the least squares method. The equation of the 4-parameter logistic function is calculated as follows: $Y=(d-a)/((1+(x/c)b))+a$ I where: a=minimum data level b=gradient I c=ICED, d=maximum data level x=inhibitor concentration.

TABLE 1

Inhibitory Activity of Compounds

| # | | Names | AS $IC_{50}$ (nM) | 11B1 % I @ 100 nM |
|---|---|---|---|---|
| 1 | Ent-2 | 3-(1,2,3,4-Tetrahydro-naphthalen-1-yl)-3H-imidazole-4-carboxylic acid isopropyl ester | 44 | 99 |
| 2 | R | Propionic acid 3-(1,2,3,4-tetrahydro-naphthalen-1-yl)-3H-imidazol-4-yl ester | 21 | |
| 3 | Ent-2 | 3-[7-(Pyrrolidine-1-carbonyl)-1,2,3,4-tetrahydro-naphthalen-1-yl]-3H-imidazole-4-carboxylic acid isopropyl ester | 215 | 87 |
| 4 | R | 3-(6-Acetylamino-1,2,3,4-tetrahydro-naphthalen-1-yl)-3H-imidazole-4-carboxylic acid isopropyl ester | 85 | |
| 5 | R | 3-(7-Methanesulfonyl-methyl-amino-1,2,3,4-tetrahydro-naphthalen-1-yl)-3H-imidazole-4-carboxylic acid isopropyl ester | 352 | |
| 6 | R | 3-(7-Cyano-1,2,3,4-tetrahydro-naphthalen-1-yl)-3H-imidazole-4-carboxylic acid isopropyl ester | 197 | |
| 7 | R | 3-(6-Cyclopropyl-1,2,3,4-tetrahydro-naphthalen-1-yl)-3H-imidazole-4-carboxylic acid isopropyl ester | 268 | |
| 8 | Ent-2 | 1-(4,4-Dimethyl-1,2,3,4-tetrahydro-naphthalen-1-yl)-5-ethyl-1H-imidazole | 35 | 100 |
| 9 | Ent-2 | 1-(4,4-Dimethyl-1,2,3,4-tetrahydro-naphthalen-1-yl)-5-ethyl-1H-imidazole | 6 | 100 |

TABLE 1-continued

Inhibitory Activity of Compounds

| # |  | Names | AS IC$_{50}$ (nM) | 11B1 % I @ 100 nM |
|---|---|---|---|---|
| 10 | Ent-1 | 3-(2,2-Dimethyl-4-oxo-1,2,3,4-tetrahydro-naphthalen-1-yl)-3H-imidazole-4-carboxylic acid methyl ester | 27 | 99 |
| 11 | Ent-1 | 3-(cis-4-Hydroxy-2,2-dimethyl-1,2,3,4-tetrahydro-naphthalen-r-1-yl)-3H-imidazole-4-carboxylic acid methyl ester | 59 | 100 |
| 12 | Ent-2 | 3-(cis-4-Hydroxy-2,2-dimethyl-1,2,3,4-tetrahydro-naphthalen-r-1-yl)-3H-imidazole-4-carboxylic acid methyl ester | 14 |  |
| 13 | R | 3-(4-Benzylamino-2,2-dimethyl-1,2,3,4-tetrahydro-naphthalen-1yl)-3H-imidazole-4-carboxylic acid methyl ester | 696 | 60 |
| 14 | R | 1-(3,3-Dimethyl-thiochroman-4-yl)-1H-imidazole | 125 | 92 |
| 15 | Ent-1 | 3-Chroman-4-yl-3H-imidazole-4-carboxylic acid isopropyl ester | 103 | 65 |
| 16 | Ent-2 | 3-Chroman-4-yl-3H-imidazole-4-carboxylic acid isopropyl ester | 150 |  |
| 17 | R | spiro[cyclopentane-1,2'-[3']-(7'-methyl-chroman-4'-yl)-3'H-imidazole-4'-carboxylic acid methyl ester]] | 175 | 100 |
| 18 | R | 5-Benzyloxy-1-isothiochroman-4-yl-1H-imidazole | 152 |  |
| 19 | R | 3-(2,2-Dimethyl-indan-1-yl)-3H-imidazole-4-carboxylic acid benzylamide | 17 |  |
| 20 | R | 3-(2,2-Dimethyl-indan-1-yl)-3H-imidazole-4-carboxylic acid (2-hydroxy-ethyl)-amide | 6 |  |
| 21 | R | 5-[3-(2,2-Dimethyl-indan-1-yl)-3H-imidazol-4-yl]-3-methyl-[1,2,4]oxadiazole | 129 | 98 |
| 22 | R | 1-(3,3-Dimethyl-indan-1-yl)-5-ethyl-1H-imidazole | 194 | 100 |
| 23 | Ent-2 | 1-(3,3-Difluoro-2,2-dimethyl-indan-1-yl)-5-ethoxymethyl-1H-imidazole | 3 | 97 |
| 23 | R | 3-Imidazol-1-yl-2,2-dimethyl-indan-1-one | 760 |  |
| 24 | R | [3-(2,2-Dimethyl-1,1-dioxo-2,3-dihydro-1H-1lambda*6*-benzo[b]thiophen-3-yl)-3H-imidazol-4-yl]-methanol | 194 | 93 |
| 25 | R | 3-(2,2-Dimethyl-2,3-dihydro-benzofuran-3-yl)-3H-imidazole-4-carboxylic acid methyl ester | 46 | 96 |
| 26 | R | 3-(6,7,8,9-Tetrahydro-5H-benzocyclohepten-5-yl)-3H-imidazole-4-carboxylic acid isopropyl ester | 5 | 99 |

Ent-1: the first eluting enantiomer.
Ent-2: the second eluting enantiomer.
AS: aldosterone synthase;
11B1: CYP11B1;
I %: percentage of inhibitory rate.

Abbreviations
aq.: aqueous
CDI: 1,1;-carbonyldiimidazole
DAST: (diethylamino)sulfur trifluoride
DCM: dichloromethane
DIBAL-H: diisobutylaluminum hydride
DMAP: 4-dimethylaminopyridine
DME: dimethoxyethane
DMF: N,N-dimethylformamide
DMSO: dimethylsulfoxide
EtOH: ethanol
ESI: electrospray ionization
h: hours
HPLC: high pressure liquid chromatography
HRMS: high resolution mass spectrometry
IPA: isopropanol
IR: infrared spectroscopy
KHMDS: potassium hexamethyldisilazide
LAH: lithium aluminum hydride
LC-MS: liquid chromatography/mass spectrometry
LDA: lithium diisoproylamide
LHMDS: lithium hexamethyldisilazide
min: minutes
MS: mass spectrometry
NBS: N-bromosuccinimide
NMR: nuclear magnetic resonance
sat.: saturated
TBSCI: tert-butyldimethylsilyl chloride
TFA: trifluoroacetic acid
THF: tetrahydrofuran
TMEDA: tetramethylethylenediamine
TBS: tert-butyl dimethylsilyl
TMSCI: trimethylsilyl chloride
TLC: thin layer chromatography
Tr: trityl
t$_r$: retention time
w/: with

EXAMPLES

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and/or spectroscopic characteristics, e.g., MS, IR, NMR. Abbreviations used are those conventional in the art. The compounds in the following examples have been found to have IC$_{50}$ values in the range of about 1 nM to about 1000 nM for aldosterone synthase and have percent inhibitions values in the range of about 10% to about 100% for CYP11B1 at 1 μM concentrations.

Examples for General Scheme 1

Example 1 a) Isopropyl 4-imidazolecarboxylate

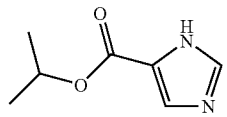

To imidazole-4-carboxylic acid (CAS#1072-84-0, 3.0 g, 26.7 mmol) in propan-2-ol (60 mL) is added thionyl chloride (15.9 g, 13.4 mmol) and the solution is refluxed overnight. The volatiles are removed in vacuo and the residue is partitioned between ethyl acetate and 4M aqueous sodium hydroxide. The organic layer is dried-over Na$_2$SO$_4$, filtered and concentrated to afford imidazole-4-carboxylic acid isopropyl ester; MS: (ESI) m/z 155.0 (M+H)+.

b) 3-(6,7,8,9-Tetrahydro-5H-benzocyclohepten-5-yl)-3H-imidazole-4-carboxylic acid isopropyl ester

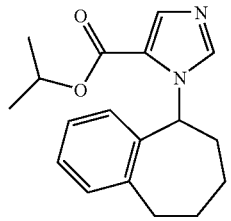 [SMILES: CC(C)OC(=O)c1cncn1C1CCCCc2ccccc21]

To a solution of isopropyl 4-imidazolecarboxylate (601 mg, 3.9 mmol) in THF (30 mL) is added 6,7,8,9-tetrahydro-5H-benzocyclohepten-5-ol (CAS#35550-94-8, 487 mg, 3.0 mmol), which can be prepared as described in Ollivier, R.; et al. *Journal of Medicinal Chemistry,* 1997, 40, 952-960, followed by triphenylphosphine (1.02 g, 3.9 mmol). The reaction is cooled to 0° C. and diisopropyl azodicarboxylate (755 µL, 3.9 mmol) is added. The reaction is permitted to warm to room temperature and stirred until LC-MS analysis indicates complete consumption of 6,7,8,9-tetrahydro-5H-benzocyclohepten-5-ol. The reaction mixture is diluted with saturated aqueous NaHCO$_3$ and ethyl acetate. The layers are separated and the organic layer is dried with Na$_2$SO$_4$, filtered, and concentrated. The resulting residue is purified by silica gel flash chromatography (ethyl acetate-dichloromethane, 0:1 to 1:1) to provide 3-(6,7,8,9-tetrahydro-5H-benzocyclohepten-5-yl)-3H-imidazole-4-carboxylic acid isopropyl ester; HRMS: (ESI) m/z 299.1775 [(M+H)+; calcd for C$_{18}$H$_{23}$N$_2$O$_2$: 299.1760]; $^1$H NMR (400 MHz, CDCl$_3$) δ ppm 1.18 (d, J=6.3 Hz, 3 H), 1.23 (d, J=6.3 Hz, 3 H), 1.36-1.50 (m, 1 H), 1.87-2.24 (m, 4 H), 2.37-2.49 (m, 1 H), 2.85-2.95 (m, 1 H), 2.97-3.09 (m, 1 H), 4.99-5.14 (m, 1 H), 5.94 (d, J=7.8 Hz, 1 H), 6.44 (d, J=10.6 Hz, 1 H), 6.97-7.08 (m, 1 H), 7.08-7.21 (m, 2 H), 7.82-7.93 (m, 2 H). The HCl salt of the title compound can be prepared by dissolution in diethyl ether, followed by treatment with an excess of 1N HCl in diethyl ether. The resulting heterogeneous solution is concentrated to furnish the HCl salt of 3-(6,7,8,9-tetrahydro-5H-benzocyclohepten-5-yl)-3H-imidazole-4-carboxylic acid isopropyl ester.

c) (R)- and (S)-3-(6,7,8,9-Tetrahydro-5H-benzocyclohepten-5-yl)-3H-imidazole-4-carboxylic acid isopropyl ester Resolution of the enantiomers of the free base of the title compound is achieved by chiral HPLC using a ChiralPak AD-H column with a 2.3:1 ethanol-heptane mobile phase to provide (R)-3-(6,7,8,9-Tetrahydro-5H-benzocyclohepten-5-yl)-3H-imidazole-4-carboxylic acid isopropyl ester (t$_r$=12.1 min) and (S)-3-(6,7,8,9-Tetrahydro-5H-benzocyclohepten-5-yl)-3H-imidazole-4-carboxylic acid isopropyl ester (t$_r$=14.8 min).

The Following Compounds can be Prepared in a Similar Fashion as Example 1

(R)- and (S)-3-(1,2,3,4-Tetrahydro-naphthalen-1-yl)-3H-imidazole-4-carboxylic acid isopropyl ester

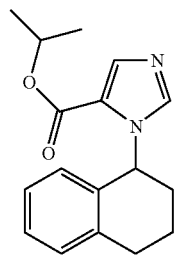 [SMILES: CC(C)OC(=O)c1cncn1C1CCCc2ccccc21]

$^1$H NMR (400 MHz, MeOD) of the HCl salt: δ ppm 1.43 (d, J=6.3 Hz, 3 H), 1.45 (d, J=6.3 Hz, 3 H), 1.71-1.82 (m, 1 H), 1.89-1.99 (m, 1 H), 2.27-2.42 (m, 2 H), 2.92 (ddd, J=16.9, 9.3, 5.3 Hz, 1 H), 3.06 (dt, J=16.9, 5.3 Hz, 1 H), 5.35 (sept, J=6.3 Hz, 1 H), 6.57 (t, J=4.9 Hz, 1 H), 7.14 (d, J=7.5 Hz, 1 H), 7.27 (t, J=7.5 Hz, 1 H), 7.30-7.42 (m, 2 H), 8.32 (s, 1 H), 8.54 (s, 1 H); MS: (ESI) m/z 285.2 (M+H)+.

Resolution of the enantiomers of the free base of the title compound is achieved by chiral HPLC using a ChiralPak IA column with a 15:85 ethyl acetate-hexanes mobile phase to provide (R)-3-(1,2,3,4-Tetrahydro-naphthalen-1-yl)-3H-imidazole-4-carboxylic acid isopropyl ester (t$_r$=27.6 min) and (S)-3-(1,2,3,4-Tetrahydro-naphthalen-1-yl)-3H-imidazole-4-carboxylic acid isopropyl ester (t$_r$=14.9 min).

3-Indan-1-yl-3H-imidazole-4-carboxylic acid isopropyl ester

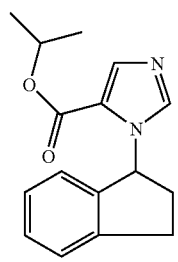 [SMILES: CC(C)OC(=O)c1cncn1C1CCc2ccccc21]

$^1$H NMR (400 MHz, CDCl$_3$) of the free base δ ppm 1.39 (d, J=6.3 Hz, 6 H), 2.07-2.22 (m, 1H), 2.67-2.90 (m, 1 H), 2.91-

3.19 (m, 2 H), 5.15-5.34 (m, 1 H), 6.54 (dd, J=7.6, 4.6 Hz, 1 H), 7.22-7.31 (m, 3 H), 7.33-7.40 (m, 2 H), 7.80 (s, 1 H); MS: (ESI) m/z 271 (M+H)+

(R)- and (S)-3-(2,3-Dihydro-benzofuran-3-yl)-3H-imidazole-4-carboxylic acid isopropyl ester

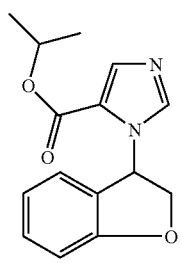 [SMILES: CC(C)OC(=O)c1cncn1C1COc2ccccc21]

¹H NMR (400 MHz, CDCl₃) of the free base: δ ppm 1.33-1.48 (m, 6 H), 4.51 (dd, J=11.1, 2.5 Hz, 1 H), 4.88 (dd, J=10.9, 7.6 Hz, 1 H), 5.15-5.38 (m, 1 H), 6.58 (dd, J=7.6, 2.5 Hz, 1 H), 6.93-7.13 (m, 2 H), 7.31-7.45 (m, 3 H), 7.83 (s, 1 H); MS: (ESI) m/z 271 (M+H)+

Resolution of the enantiomers of the free base of the title compound is achieved by chiral HPLC using a ChiralPak AS-H column with a 1:9 isopropanol-heptane mobile phase to provide (R)-3-(2,3-Dihydro-benzofuran-3-yl)-3H-imidazole-4-carboxylic acid isopropyl ester (t$_r$=14.2 min) and (S)-3-(2,3-Dihydro-benzofuran-3-yl)-3H-imidazole-4-carboxylic acid isopropyl ester (t$_r$=17.8 min).

3-(4,4-Dimethyl-1,2,3,4-tetrahydro-naphthalen-1-yl)-3H-imidazole-4-carboxylic acid isopropyl ester

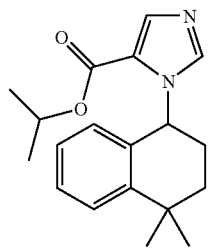 [SMILES: CC(C)OC(=O)c1cncn1C1CCC(C)(C)c2ccccc21]

¹H NMR (400 MHz, CDCl₃) of the free base: δ ppm 1.31 (s, 3 H), 1.36-1.42 (m, 9 H), 1.60-1.69 (m, 2 H), 2.02-2.14 (m, 1H), 2.23-2.38 (m, 1 H), 5.18-5.31 (m, 1 H), 6.23 (t, J=4.8 Hz, 1H), 6.99 (d, J=7.6 Hz, 1 H), 7.06 (s, 1 H), 7.11-7.18 (m, 1 H), 7.29-7.37 (m, 1 H), 7.42-7.49 (m, 1 H), 7.78 (d, J=1.0 Hz, 1 H); MS: (ESI) m/z 313.2 (M+H)+

3-(3,3-Dimethyl-indan-1-yl)-3H-imidazole-4-carboxylic acid isopropyl ester

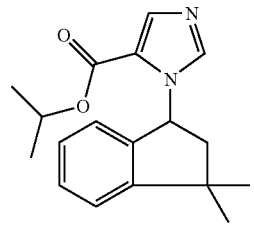 [SMILES: CC(C)OC(=O)c1cncn1C1CC(C)(C)c2ccccc21]

¹H NMR (400 MHz, CDCl₃) of the free base: δ ppm 1.31 (s, 3 H), 1.35 (s, 3H), 1.38 (s, 3 H), 1.40 (s, 3 H), 1.99 (dd, J=13.3, 6.7 Hz, 1 H), 2.72 (dd, J=13.3, 7.7 Hz, 1 H), 5.20-5.30 (m, 1 H), 6.56 (t, J=7.2 Hz, 1 H), 7.16 (d, J=8.3 Hz, 1 H), 7.25-7.32 (m, 2 H), 7.38 (d, J=7.3 Hz, 1 H), 7.40 (s, 1 H), 7.80 (d, J=1.0 Hz, 1 H); MS: (ESI) m/z 299 (M+H)+.

3-Isothiochroman-4-yl-3H-imidazole-4-carboxylic acid isopropyl ester

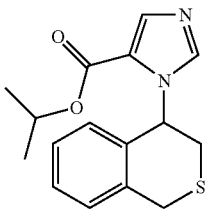 [SMILES: CC(C)OC(=O)c1cncn1C1CSCc2ccccc21]

¹H NMR (400 MHz, CDCl₃) of the free base: δ ppm 1.35-1.42 (m, 6 H), 3.02-3.16 (m, 1 H), 3.34 (dd, J=14.4, 3.5 Hz, 1 H), 3.73 (dd, J=16.4, 1.5 Hz, 1 H), 4.04 (d, J=16.4 Hz, 1 H), 5.18-5.29 (m, 1 H), 6.46 (t, J=3.5 Hz, 1 H), 7.09 (d, J=7.3 Hz, 1 H), 7.18-7.36 (m, 4 H), 7.79 (d, J=1.0 Hz, 1 H); MS: (ESI) m/z 303.2 (M+H)+.

Example 2 a) 3-(1,2,3,4-Tetrahydro-naphthalen-1-yl)-3H-imidazole-4-carboxylic acid methyl ester

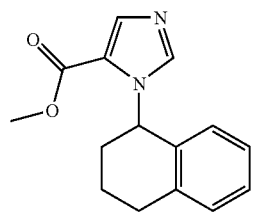 [SMILES: COC(=O)c1cncn1C1CCCc2ccccc21]

To a solution of 1,2,3,4-tetrahydro-1-naphthol (CAS#529-33-9, 1.00 g, 6.74 mmol), which can be prepared as described in Ollivier, R.; et al. *Journal of Medicinal Chemistry*, 1997, 40, 952-960, in THF (60 mL), at 0° C. is added methyl 4-imidazolecarboxylate (CAS#17325-26-7, 0.85 g, 6.74 mmol) and triphenylphosphine, followed by diisopropyl azodicarboxylate (1.36 g, 6.74 mmol). The cooling bath is then removed. After 16 hours, the solvent is evaporated in vacuo and the residue is purified by silica gel flash chromatography (elution with ethyl acetate) to give a partially purified product, which is dissolved in ethyl acetate and extracted with 1M aqueous HCl. The aqueous layer is basified to a pH of ca. 9 with 2M aqueous NaOH, and then extracted three times with dichloromethane. The organic layers are combined, dried with $MgSO_4$, filtered, and concentrated to furnish 3-(1,2,3,4-tetrahydro-naphthalen-1-yl)-3H-imidazole-4-carboxylic acid methyl ester; MS: (ESI) m/z 257.2 $(M+H)^+$. The $HNO_3$ salt of the title compound is prepared by dissolving the free base in methanol, followed by treatment with an excess of a 1:1 solution of $HNO_3$—$H_2O$. Concentration and trituration with diethyl ether and methanol, provides the nitric acid salt of 3-(1,2,3,4-tetrahydro-naphthalen-1-yl)-3H-imidazole-4-carboxylic acid methyl ester; $^1$H NMR (400 MHz, DMSO-$d_6$) δ ppm 1.66-1.87 (m, 2 H), 2.11-2.33 (m, 2 H), 2.81 (dt, J=17.2, 6.5 Hz, 1 H), 2.93 (dt, J=17.2, 6.0 Hz, 1 H), 3.87 (s, 3 H), 6.33 (t, J=5.9 Hz, 1 H), 6.99 (d, J=7.6 Hz, 1 H), 7.10-7.21 (m, 1 H), 7.21-7.35 (m, 2 H), 8.34 (s, 1 H), 8.58 (s, 1 H).

The Following Compounds can be Prepared in a Similar Fashion as Example 2

(R)- and (S)-3-(2,3-Dihydro-benzofuran-3-yl)-3H-imidazole-4-carboxylic acid methyl ester

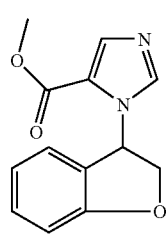 [SMILES: COC(=O)c1cncn1C1COc2ccccc21]

$^1$H NMR (400 MHz, CDCl$_3$) of the free base: δ ppm 1.33-1.48 (m, 6 H), 4.51 (dd, J=11.1, 2.5 Hz, 1 H), 4.88 (dd, J=10.9, 7.6 Hz, 1 H), 5.15-5.38 (m, 1 H), 6.58 (dd, J=7.6, 2.5 Hz, 1 H), 6.93-7.13 (m, 2 H), 7.31-7.45 (m, 3 H), 7.83 (s, 1 H); MS: (ESI) m/z 271 $(M+H)^+$.

Resolution of the enantiomers of the free base of the title compound is achieved by chiral HPLC using a ChiralPak AS-H column with a 1:9 isopropanol-heptane mobile phase to provide LDD871 ($t_r$=10.6 min) and LDD872 ($t_r$=12.2 min).

3-(6-Cyano-1,2,3,4-tetrahydro-naphthalen-1-yl)-3H-imidazole-4-carboxylic acid methyl ester

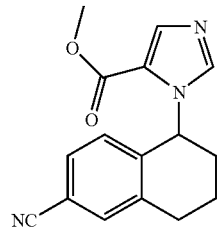

$^1$H NMR (400 MHz, CDCl$_3$) of the free base: δ ppm 1.83-1.96 (m, 2 H), 2.11-2.20 (m, 1 H), 2.25-2.34 (m, 1 H), 2.84-2.93 (m, 1 H), 2.97-3.05 (m, 1 H), 3.88 (s, 3 H), 6.31-6.36 (m, 1 H), 7.00 (d, J=8.1 Hz, 1 H), 7.25 (s, 1 H), 7.42 (d, J=8.1 Hz, 1 H), 7.52 (s, 1 H), 7.82 (s, 1 H); MS: (ESI) m/z 289.19 $(M+H)^+$.

3-(4,4-Dimethyl-1,2,3,4-tetrahydro-naphthalen-1-yl)-3H-imidazole-4-carboxylic acid methyl ester

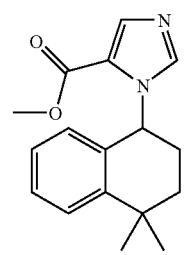 [SMILES: COC(=O)c1cncn1C1CCC(C)(C)c2ccccc21]

$^1$H NMR (400 MHz, CDCl$_3$) of the free base: δ ppm 1.31 (s, 3 H), 1.40 (s, 3 H), 1.60-1.77 (m, 2 H), 2.04-2.14 (m, 1 H), 2.24-2.37 (m, 1 H), 3.90 (s, 3 H), 6.23 (t, J=4.8 Hz, 1 H), 6.97 (d, J=7.6 Hz, 1 H), 7.09 (s, 1 H), 7.11-7.18 (m, 1 H), 7.29-7.37 (m, 1 H), 7.45 (d, J=8.1 Hz, 1 H), 7.81 (s, 1 H); MS: (ESI) m/z 285.2 $(M+H)^+$.

3-(3,3-Dimethyl-indan-1-yl)-3H-imidazole-4-carboxylic acid methyl ester

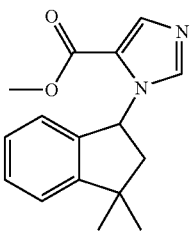 [SMILES: COC(=O)c1cncn1C1CC(C)(C)c2ccccc21]

$^1$H NMR (400 MHz, CDCl$_3$) of the free base: δ ppm 1.31 (s, 3 H), 1.34 (s, 3 H), 1.98 (dd, J=13.4, 6.6 Hz, 1 H), 2.71 (dd, J=13.4, 7.8 Hz, 1 H), 3.89 (s, 3 H), 6.55 (t, J=7.2 Hz, 1 H), 7.14

(d, J=7.1 Hz, 1 H), 7.24-7.31 (m, 2 H), 7.37 (d, J=7.3 Hz, 1 H), 7.41 (s, 1 H), 7.81 (s, 1 H); MS: (ESI) m/z 271 (M+H)+;

The resolution of the enantiomers of the titled compound is achieved by chiral HPLC using a ChiralPak IA column with 1:1 heptane:ethanol to give two enantiomers (t$_r$=9.5 min, and t$_r$=15.0 min)

Example 3 a) 3-(5-Fluoro-indan-1-yl)-3H-imidazole-4-carboxylic acid methyl ester

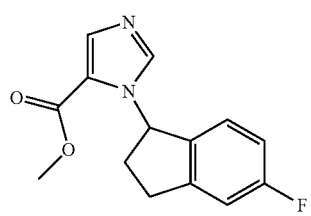 [SMILES: COC(=O)c1cncn1C1CCc2cc(F)ccc21]

To a solution of 5-fluoroindanone (CAS#700-84-5, 0.942 g, 6.274 mmol) in methanol (15 mL) at 0° C. is added sodium borohydride (0.356 g, 9.411 mmol) in one portion. The cooling bath is removed and after 2 hours, the mixture is poured into water (100 mL) and the volatile organics are removed in vacuo. Extraction with dichloromethane, drying over magnesium sulfate, filtering through a cotton plug and concentration affords 5-fluoro-indan-1-ol, which is used in the next step without further purification.

To a solution of 5-fluoro-indan-1-ol (0.293 g, 1.925 mmol) and methyl 4-imidazolecarboxylate (CAS#17325-26-7, 0.163 g, 1.290 mmol) in THF (10 mL) at 0° C. is added pMe$_2$NPhP(Ph)$_2$ (0.619 g, 1.925 mmol) and diisopropyl azodicarboxylate (94%, 0.414 g, 1.925 mmol). After 1 hour the mixture is warmed to room temperature and after 18 hours it is diluted with ethyl acetate and extracted with 1M aqueous HCl. The extracts are cooled to 0° C., and the pH is adjusted to ca. 9 with ice-cold 4M aqueous NaOH. The basic aqueous phase is extracted three times with dichloromethane, and the combined organic phases are dried over magnesium sulfate, filtered through a cotton plug, and concentrated. The resulting residue is purified by silica gel flash chromatography (elution with dichloromethane-methanol, 1:0 to 99:1 to 49:1) to afford 3-(5-fluoro-indan-1-yl)-3H-imidazole-4-carboxylic acid methyl ester; MS: (ESI) m/z 261.0 (M+H)+. The HCl salt of the title compound can be prepared by dissolution in diethyl ether followed by treatment with an excess of 1N HCl in diethyl ether. The resulting heterogeneous solution is concentrated to furnish the HCl salt of 3-(5-fluoro-indan-1-yl)-3H-imidazole-4-carboxylic acid methyl ester; $^1$H NMR (400 MHz, CDCl$_3$) δ ppm 2.06-2.20 (m, 1 H), 2.71-2.85 (m, 1 H), 2.87-3.00 (m, 1 H), 3.00-3.14 (m, 1 H), 3.87 (s, 3 H), 6.47 (dd, J=7.7, 4.7 Hz, 1 H), 6.88-6.97 (m, 1 H), 7.01 (dd, J=8.6, 2.3 Hz, 1 H), 7.16 (dd, J=8.6, 5.1 Hz, 1 H), 7.19 (s, 1 H), 7.77 (s, 1 H).

The Following Compounds can be Prepared in a Similar Fashion as Example 3

3-(5-Chloro-indan-1-yl)-3H-imidazole-4-carboxylic acid methyl ester

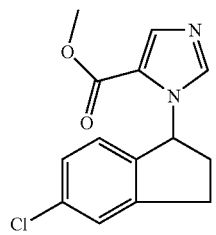 [SMILES: COC(=O)c1cncn1C1CCc2cc(Cl)ccc21]

$^1$H NMR (400 MHz, CDCl$_3$) of the HCl salt: δ ppm 2.10-2.18 (m, 1 H), 2.76-2.85 (m, 1 H), 2.93-3.01 (m, 1 H), 3.05-3.13 (m, 1 H), 3.89 (s, 3 H), 6.51 (dd, J=7.6, 5.1 Hz, 1 H), 7.14 (d, J=8.1 Hz, 1 H), 7.23-7.25 (m, 2 H), 7.34 (s, 1 H), 7.79 (s, 1 H); MS: (ESI) m/z 276.9, 278.9 (M+H)+.

3-(5-Cyano-indan-1-yl)-3H-imidazole-4-carboxylic acid methyl ester

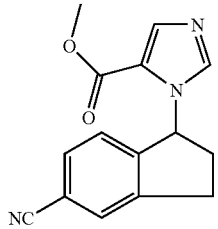

$^1$H NMR (400 MHz, MeOD) of the free base δ ppm 2.33-2.42 (m, 1 H), 2.84-2.94 (m, 1 H), 3.09-3.17 (m, 1 H), 3.24-3.32 (m, 1 H), 3.91 (s, 3 H), 6.71 (t, J=7.5 Hz, 1 H), 7.34 (d, J=7.8 Hz, 1 H), 7.65 (d, J=8.6 Hz, 1 H), 7.67 (s, 1 H), 7.79 (br. s., 1 H), 7.80 (s, 1 H); MS: (ESI) m/z 268.1 (M+H)+.

cis- and trans-3-(2-Phenyl-indan-1-yl)-3H-imidazole-4-carboxylic acid methyl ester

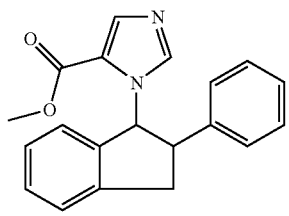 [SMILES: COC(=O)c1cncn1C1c2ccccc2CC1c1ccccc1]

The requisite alcohol, 2-phenyl-indan-1-ol (CAS #53786-92-8), for the construction of the title compound via the method described in Example 3 can be prepared as described by Christol, H.; et al. *Bulletin de la Societe Chimique de France*, 1960, 1696-1699.

MS: (ESI) m/z 319.11 (M+H)$^+$; $^1$H NMR (400 MHz, CDCl$_3$) of a ca. 1:1 mixture of diastereomers: δ ppm 3.24 (dd, J=15.9, 8.1 Hz, 1 H), 3.34-3.54 (m, 3 H), 3.68 (s, 3 H), 3.69-3.72 (m, 1 H), 3.73 (s, 3 H), 4.12 (q, J=7.7 Hz, 1 H), 6.72 (d, J=6.8 Hz, 1 H), 6.80-6.90 (m, 4 H), 7.04-7.20 (m, 6 H), 7.23-7.49 (m, 11 H), 7.51 (s, 1 H), 7.76 (d, J=1.0 Hz, 1 H).

Example 4 a) 3-(5-Methoxy-1,2,3,4-tetrahydro-naphthalen-1-yl)-3H-imidazole-4-carboxylic acid isopropyl ester

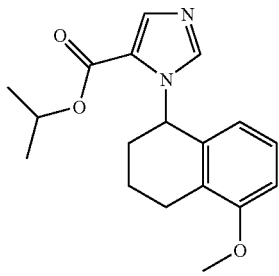 [SMILES: COc1cccc2c1CCCC2n1cncc1C(=O)OC(C)C]

To a solution of 5-methoxy-3,4-dihydro-2H-naphthalen-1-one (CAS#33892-75-0, 10 g, 5.67 mmol) in methanol (40 mL) and dichloromethane (5 mL) at 0° C. is added sodium borohydride (0.579 g, 8.51 mmol) in one portion. The cooling bath is removed and after 1.5 hours, the mixture is poured into water (75 mL) and the volatile organics are removed in vacuo. Extraction with dichloromethane, drying over sodium sulfate, filtering through a cotton plug and concentration affords 5-methoxy-1,2,3,4-tetrahydro-naphthalen-1-ol, which is used in the next step without further purification.

To a suspension of 5-methoxy-1,2,3,4-tetrahydro-naphthalen-1-ol (0.150 g, 0.842 mmol) and isopropyl 4-imidazolecarboxylate (0.087 g, 0.564 mmol), which can be prepared as described in Example 1, in THF (5 mL) at 0° C. is added triphenylphosphine (0.221 g, 0.842 mmol) followed by diisopropyl azodicarboxylate (94%, 0.181 g, 0.842 mmol). After 1 hour the mixture is diluted with ethyl acetate and extracted twice with 1M aqueous HCl. The aqueous phase is basified to a pH of ca. 9 with 2M aqueous NaOH and is extracted three times with dichloromethane. The combined organic phases are dried over magnesium sulfate, filtered, and concentrated to give a colorless residue, which is purified by silica gel flash chromatography (elution with dichloromethane-methanol, 99:1) to give 3-(5-methoxy-1,2,3,4-tetrahydro-naphthalen-1-yl)-3H-imidazole-4-carboxylic acid isopropyl ester; MS: (ESI) m/z 315.1 (M+H)$^+$. The HCl salt of the title compound can be prepared by dissolution in diethyl ether, followed by treatment with an excess of 1N HCl in diethyl ether. The resulting heterogeneous solution is concentrated to furnish the HCl salt of 3-(5-methoxy-1,2,3,4-tetrahydro-naphthalen-1-yl)-3H-imidazole-4-carboxylic acid isopropyl ester; $^1$H NMR (400 MHz, MeOD) δ ppm 1.44 (d, J=6.3 Hz, 3 H), 1.45 (d, J=6.0 Hz, 3 H), 1.62-1.72 (m, 1 H), 1.90-1.97 (m, 1 H), 2.26-2.34 (m, 2 H), 2.66-2.74 (m, 1 H), 2.95-3.02 (m, 1 H), 3.92 (s, 3 H), 5.30-5.40 (m, 1 H), 6.53 (t, J=4.7 Hz, 1 H), 6.74 (d, J=8.0 Hz, 1 H), 7.02 (d, J=8.0 Hz, 1 H), 7.27 (t, J=8.0 Hz, 1 H), 8.32 (s, 1 H), 8.56 (s, 1 H).

The Following Compounds can be Prepared in a Similar Fashion as Example 4

3-(7-Methoxy-1,2,3,4-tetrahydro-naphthalen-1-yl)-3H-imidazole-4-carboxylic acid isopropyl ester

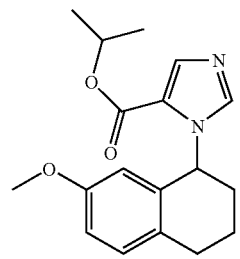 [SMILES: COc1ccc2c(c1)C(n1cncc1C(=O)OC(C)C)CCC2]

$^1$H NMR (400 MHz, CDCl$_3$) of the HCl salt: δ ppm 1.37 (d, J=6.3 Hz, 3 H), 1.38 (d, J=6.3 Hz, 3 H), 1.63-1.73 (m, 1 H), 1.76-1.84 (m, 1 H), 2.04-2.12 (m, 1 H), 2.14-2.22 (m, 1 H), 2.72-2.79 (m, 1 H), 2.87 (dt, J=16.7, 5.5 Hz, 1 H), 3.69 (s, 3 H), 5.23 (sept, J=6.3 Hz, 1 H), 6.23 (t, J=5.1 Hz, 1 H), 6.50 (d, J=2.5 Hz, 1 H), 6.84 (dd, J=8.6, 2.5 Hz, 1 H), 7.11 (d, J=8.6 Hz, 1 H), 7.15 (s, 1 H), 7.77 (s, 1 H); MS: (ESI) m/z 315.1 (M+H)$^+$.

3-(6-Cyano-1,2,3,4-tetrahydro-naphthalen-1-yl)-3H-imidazole-4-carboxylic acid isopropyl ester

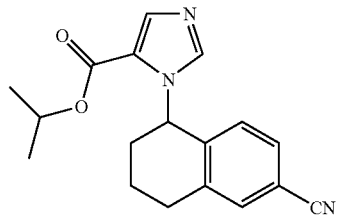 [SMILES: CC(C)OC(=O)c1cncn1C1CCCc2cc(C#N)ccc21]

$^1$H NMR (400 MHz, MeOD) of the HCl salt: δ ppm 1.40 (d, J=6.3 Hz, 3 H), 1.42 (d, J=6.3 Hz, 3 H), 1.86-2.03 (m, 2 H), 2.30-2.45 (m, 2 H), 2.97 (dt, J=17.4, 6.5 Hz, 1 H), 3.10 (dt, J=17.4, 6.3 Hz, 1 H), 5.28 (sept, J=6.3, 1 H), 6.55 (t, J=5.9 Hz, 1 H), 7.21 (d, J=8.1 Hz, 1 H), 7.56 (dd, J=8.1, 1.5 Hz, 1 H), 7.70 (s, 1 H), 8.20 (s, 1 H), 8.51 (s, 1 H); MS: (ESI) m/z 310.1 (M+H)⁺

3-(5,7-Dimethyl-1,2,3,4-tetrahydro-naphthalen-1-yl)-3H-imidazole-4-carboxylic acid isopropyl ester

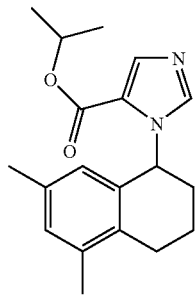 [SMILES: Cc1cc(C)c2c(c1)C(n1cncc1C(=O)OC(C)C)CCC2]

¹H NMR (400 MHz, MeOD) of the HCl salt δ ppm 1.43 (d, J=6.0 Hz, 3 H), 1.45 (d, J=6.3 Hz, 3 H), 1.58-1.74 (m, 1 H), 1.91-2.00 (m, 1 H), 2.24-2.29 (m, 2 H), 2.26 (s, 3 H), 2.31 (s, 3 H), 2.64-2.73 (m, 1 H), 2.90 (dt, J=17.4, 5.0 Hz, 1 H), 5.29-5.38 (m, 1 H), 6.44 (t, J=4.5 Hz, 1 H), 6.79 (s, 1 H), 7.10 (s, 1 H), 8.19 (s, 1 H), 8.20 (s, 1 H); MS: (ESI) m/z 313.2 (M+H)⁺.

Example 5 a) 7-Bromo-1,2,3,4-tetrahydro-naphthalen-1-ol

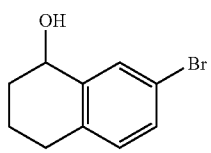 [SMILES: OC1CCCc2ccc(Br)cc21]

To a solution of 7-bromo-3,4-dihydro-2H-naphthalen-1-one (CAS#32281-97-3, 3.5 g, 0.015 mol) in methanol (7 mL) and dichloromethane (10 mL) at 0° C. is added sodium borohydride (1.47 g, 0.038 mol) in one portion. The cooling bath is removed and after 1.5 hours, the mixture is poured into water and the volatile organics are removed in vacuo. Extraction with dichloromethane, drying over sodium sulfate, filtering through a cotton plug and concentration in vacuo affords 7-bromo-1,2,3,4-tetrahydro-naphthalen-1-ol. ¹H NMR (400 MHz, CDCl₃) δ ppm 1.72 (d, J=6.3 Hz, 1 H), 1.74-1.90 (m, 2 H), 1.92-2.07 (m, 2 H), 2.62-2.71 (m, 1 H), 2.73-2.82 (m, 1 H), 4.73-4.77 (m, 1 H), 6.98 (d, J=8.2 Hz, 1 H), 7.31 (dd, J=8.2, 2.1 Hz, 1 H), 7.61 (d, J=2.1 Hz, 1 H).

b) 3-(7-Bromo-1,2,3,4-tetrahydro-naphthalen-1-yl)-3H-imidazole-4-carboxylic acid isopropyl ester

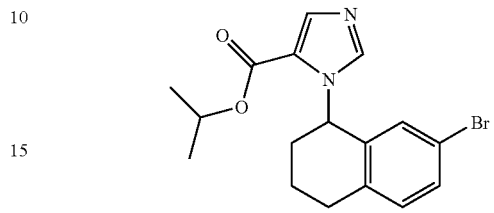

To a suspension of 7-bromo-1,2,3,4-tetrahydro-naphthalen-1-ol (2.5 g, 11.0 mmol) and isopropyl 4-imidazolecarboxylate (1.18 g, 7.66 mmol), which can be prepared as described in Example 1, (2.33 g, 10.98 mmol) in THF (20 mL) at 0° C. is added triphenylphosphine and dimethyl azodicarboxylate (40% wt. in toluene, 4.01 g, 10.98 mmol). After 10 min, the cooling bath is removed and after another 30 min, water is added and the mixture is extracted twice with ethyl acetate. The organic layers are dried over magnesium sulfate, filtered, and concentrated. The resulting residue is purified by silica gel chromatography (elution with hexanes-ethyl acetate mixtures) to give 3-(7-bromo-1,2,3,4-tetrahydro-naphthalen-1-yl)-3H-imidazole-4-carboxylic acid isopropyl ester; MS: (ESI) m/z 363.02, 365.02 (M+H)⁺; ¹H NMR (400 MHz, MeOD) δ ppm 1.42 (d, J=6.1 Hz, 3 H), 1.44 (d, J=6.3 Hz, 3 H), 1.73-1.84 (m, 1 H), 1.89-1.98 (m, 1 H), 2.26-2.40 (m, 2 H), 2.82-2.91 (m, 1 H), 3.00 (dt, J=17.2, 5.6 Hz, 1 H), 5.27-5.37 (m, 1 H), 6.50 (t, J=5.3 Hz, 1 H), 7.26 (d, J=8.3 Hz, 1 H), 7.32 (d, J=2.1 Hz, 1 H), 7.51 (dd, J=8.3, 2.1 Hz, 1 H), 8.23 (d, J=1.5 Hz, 1 H), 8.50 (d, J=1.0 Hz, 1 H).

The Following Compounds can be Prepared in a Similar Fashion as Example 5

3-(7-Nitro-1,2,3,4-tetrahydro-naphthalen-1-yl)-3H-imidazole-4-carboxylic acid isopropyl ester

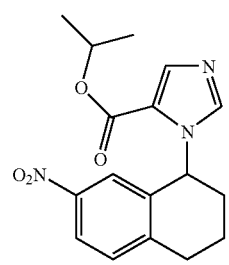 [SMILES: CC(C)OC(=O)c1cncn1C1CCCc2ccc([N+](=O)[O-])cc21]

¹H NMR (400 MHz, MeOD) of the HCl salt: δ ppm 1.36 (d, J=6.3 Hz, 3 H), 1.39 (d, J=6.3 Hz, 3 H), 1.94-2.01 (m, 2 H), 2.32-2.37 (m, 2 H), 3.02 (dt, J=17.7, 6.0 Hz, 1 H), 3.17 (dt, J=17.7, 6.8 Hz, 1 H), 5.20 (sept, J=6.3 Hz, 1 H), 6.41 (t, J=6.6 Hz, 1 H), 7.51 (d, J=8.6 Hz, 1 H), 7.68 (s, 1 H), 7.74 (d, J=2.0

Hz, 1 H), 7.80 (d, J=1.0 Hz, 1 H), 8.13 (dd, J=8.6, 2.0 Hz, 1 H); MS: (ESI) m/z 330.2 (M+H)+.

3-Chroman-4-yl-3H-imidazole-4-carboxylic acid isopropyl ester

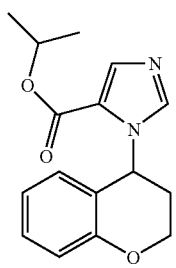 [SMILES: CC(C)OC(=O)c1cncn1C1CCOc2ccccc21]

$^1$H NMR (400 MHz, MeOD) of the HCl salt: δ ppm 1.40 (d, J=6.1 Hz, 6 H), 2.32-2.39 (m, 1 H), 2.43-2.52 (m, 1 H), 4.02-4.08 (m, 1 H), 4.31 (dd, J=11.4, 4.3 Hz, 1 H), 5.26 (sept, J=6.3 Hz, 1 H), 6.30 (t, J=4.8 Hz, 1 H), 6.94-6.97 (m, 2 H), 7.02-7.05 (m, 1 H), 7.29-7.33 (m, 1 H), 7.45 (s, 1 H), 7.77 (s, 1 H); MS: (ESI) m/z 287.0 (M+H)+.

Resolution of the enantiomers of the free base of the title compound is achieved by chiral HPLC using a ChiralPak IA column with a 1:19 isopropanol-heptane mobile phase to provide two enantiomers ($t_r$=12.7 min, and $t_r$=17.3 min).

Example 6 a) 7-Cyano-1,2,3,4-tetrahydro-naphthalen-1-ol

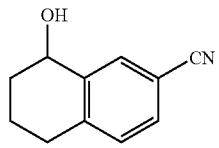 [SMILES: N#Cc1ccc2c(c1)C(O)CCC2]

To a solution of 7-bromo-1,2,3,4-tetrahydro-naphthalen-1-ol (0.708 g, 3.11 mmol), which can be prepared as described in Example 5, in DMF (6.5 mL) is added zinc cyanide (0.274 g, 2.33 mmol). Four evacuation-nitrogen fill cycles are performed and tetrakis(triphenylphosphine) palladium (0.072 g, 0.062 mmol) is added. The mixture is heated to 95° C. until the reaction is complete, whereupon water and diethyl ether are added. The mixture is filtered through Celite® and the organic phase is washed with water, dried with MgSO$_4$, filtered and concentrated to give 7-cyano-1,2,3,4-tetrahydro-naphthalen-1-ol; $^1$H NMR (400 MHz, CDCl$_3$) δ ppm 1.76-1.92 (m, 2 H), 1.95-2.13 (m, 2 H), 2.73-2.94 (m, 2 H), 4.77-4.80 (m, 1 H), 7.20 (d, J=8.0 Hz, 1 H), 7.46 (dd, J=8.0, 1.6 Hz, 1 H), 7.79 (br. s, 1 H).

b) 3-(7-Cyano-1,2,3,4-tetrahydro-naphthalen-1-yl)-3H-imidazole-4-carboxylic acid isopropyl ester

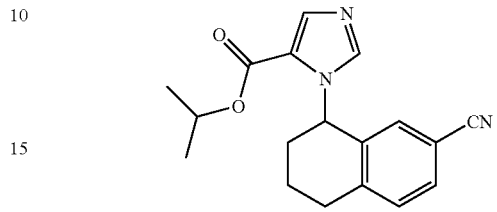

To a suspension of 7-cyano-1,2,3,4-tetrahydro-naphthalen-1-ol (0.298 g, 1.72 mmol) and isopropyl 4-imidazolecarboxylate (0.185 g, 1.204 mmol), which can be prepared as described in Example 1, in THF (10 mL) at 0° C. is added triphenylphosphine (0.451 g, 1.72 mmol), followed by diisopropyl azodicarboxylate (94%, 0.369 g, 1.72 mmol). After 1 hour the mixture is diluted with ethyl acetate and washed with water. The organic phase is dried over MgSO$_4$, filtered and concentrated. The resulting residue is purified by silica gel chromatography (elution with hexanes-ethyl acetate mixtures) to give 3-(7-cyano-1,2,3,4-tetrahydro-naphthalen-1-yl)-3H-imidazole-4-carboxylic acid isopropyl ester; MS: (ESI) m/z 310.1 (M+H)+. The HCl salt of the title compound can be prepared by dissolution in diethyl ether followed by treatment with an excess of 1N HCl in diethyl ether. The resulting heterogeneous solution is concentrated to furnish the HCl salt of 3-(7-cyano-1,2,3,4-tetrahydro-naphthalen-1-yl)-3H-imidazole-4-carboxylic acid isopropyl ester; $^1$H NMR (400 MHz, MeOD) δ ppm 1.36 (d, J=6.1 Hz, 3 H), 1.39 (d, J=6.3 Hz, 3 H), 1.90-1.98 (m, 2 H), 2.29-2.33 (m, 2 H), 2.97 (dt, J=17.7, 6.3 Hz, 1 H), 3.12 (dd, J=17.7, 6.8 Hz, 1 H), 5.21 (sept, J=6.3 Hz, 1 H), 6.35 (t, J=6.3 Hz, 1 H), 7.25 (s, 1 H), 7.45 (d, J=8.1 Hz, 1 H), 7.59 (s, 1 H), 7.62 (dd, J=8.1, 1.5 Hz, 1 H), 7.78 (d, J=1.5 Hz, 1 H).

Example 7 a) 7-Pyrrolidin-1-yl-3,4-dihydro-2H-naphthalen-1-one

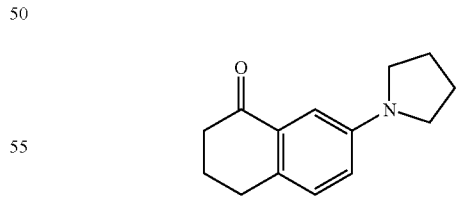

A dry flask is charged with 7-bromo-3,4-dihydro-2H-naphthalen-1-one (CAS#32281-97-3, 0.102 g, 0.454 mmol), pyrrolidine (0.065 g, 0.909 mmol), 2-(di-t-butylphosphino)-biphenyl (0.020 g, 0.067 mmol), sodium tert-butoxide (0.087 g, 0.905 mmol) and toluene (3 mL). The flask is evacuated and filled with nitrogen three times. Pd$_2$(dba)$_3$ (0.041 g, 0.045 mmol) is added and the mixture is heated to reflux for 3 hours, whereupon the mixture is cooled to room temperature, diluted with dichloromethane and washed with water. The organic phase is dried over sodium sulfate and concentrated. The resulting residue is purified by silica gel chromatography (elution with hexanes-ethyl acetate mixtures) to give 7-pyrrolidin-1-yl-3,4-dihydro-2H-naphthalen-1-one; $^1$H NMR (400 MHz, CDCl$_3$) δ ppm 1.99-2.03 (m, 4 H), 2.06-2.14 (m, 2 H), 2.60-2.65 (m, 2 H), 2.87 (t, J=6.1 Hz, 2 H), 3.28-3.35 (m, 4 H), 6.75 (dd, J=8.3, 2.8 Hz, 1 H), 7.12 (d, J=8.3 Hz, 1 H), 7.19 (d, J=2.8 Hz, 1 H).

b) 3-(7-Pyrrolidin-1-yl-1,2,3,4-tetrahydro-naphthalen-1-yl)-3H-imidazole-4-carboxylic acid isopropyl ester

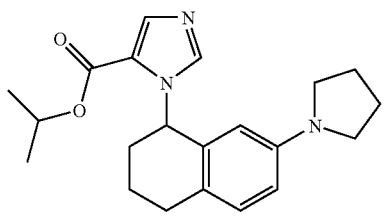 [SMILES: CC(C)OC(=O)c1cncn1C1CCCc2ccc(N3CCCC3)cc21]

To a solution of 7-pyrrolidin-1-yl-3,4-dihydro-2H-naphthalen-1-one (0.548 g, 2.55 mmol) in methanol (20 mL) at 0° C. is added sodium borohydride (0.241 g, 3.54 mmol) and the reaction is stirred for 1.5 hours, whereupon water is added and the volatiles are removed in vacuo. The mixture is extracted with dichloromethane. The organic phase is dried over sodium sulfate, filtered, and concentrated to give 7-pyrrolidin-1-yl-3,4-dihydro-2H-naphthalen-1-ol, which is used in the next step without further purification.

To a suspension of 7-pyrrolidin-1-yl-3,4-dihydro-2H-naphthalen-1-ol (0.300 g, 1.382 mmol), and isopropyl 4-imidazolecarboxylate (0.149 g, 0.967 mmol), which can be prepared as described in Example 1, in THF (10 mL) at 0° C. is added triphenylphosphine (0.293 g, 1.382 mmol) and dimethyl azodicarboxylate (40% wt. in toluene, 0.505 g, 1.382 mmol). After 10 minutes, the cooling bath is removed and the mixture is stirred for another 30 minutes. Water is added and the mixture is extracted with ethyl acetate. The organic phase is dried over sodium sulfate, filtered and concentrated. The resulting residue is purified by silica gel chromatography (elution with hexanes-ethyl acetate mixtures) to give 3-(7-pyrrolidin-1-yl-1,2,3,4-tetrahydro-naphthalen-1-yl)-3H-imidazole-4-carboxylic acid isopropyl ester; MS: (ESI) m/z 354.2 (M+H)$^+$; $^1$H NMR (400 MHz, MeOD) δ ppm 1.40 (d, J=6.3 Hz, 3 H), 1.41 (d, J=6.3 Hz, 3 H), 1.66-1.75 (m, 1 H), 1.79-1.87 (m, 1 H), 1.98-2.01 (m, 4 H), 2.13-2.25 (m, 2 H), 2.77 (ddd, J=16.7, 8.8, 5.3 Hz, 1 H), 2.88 (dt, J=16.7, 5.6 Hz, 1H), 3.12-3.24 (m, 4 H), 5.27 (sept, J=6.3 Hz, 1 H), 6.14 (d, J=2.5 Hz, 1 H), 6.24 (t, J=5.1 Hz, 1 H), 6.62 (dd, J=8.6, 2.5 Hz, 1 H), 7.08 (d, J=8.6 Hz, 1 H), 7.31 (s, 1 H), 7.73 (d, J=1.3 Hz, 1 H).

The Following Compound can be Prepared in a Similar Fashion as Example 7

3-(7-Morpholin-4-yl-1,2,3,4-tetrahydro-naphthalen-1-yl)-3H-imidazole-4-carboxylic acid isopropyl ester

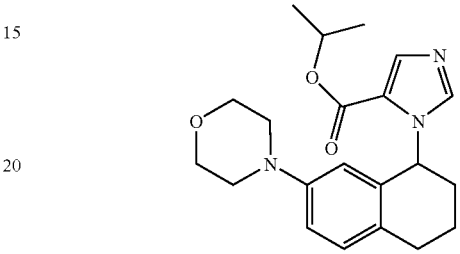

$^1$H NMR (400 MHz, MeOD) of the free base ☐ δ ppm 1.40 (d, J=6.3 Hz, 3 H), 1.40 (d, J=6.3 Hz, 3 H), 1.69-1.78 (m, 1 H), 1.81-1.90 (m, 1 H), 2.15-2.27 (m, 2 H), 2.80 (ddd, J=16.7, 9.0, 5.8 Hz, 1 H), 2.93 (dt, J=16.7, 5.6 Hz, 1 H), 2.98-3.09 (m, 4 H), 3.80 (t, J=4.8 Hz, 4 H), 5.25 (sept, J=6.3 Hz, 1 H), 6.27 (t, J=5.1 Hz, 1 H), 6.55 (d, J=2.5 Hz, 1 H), 6.99 (dd, J=8.5, 2.5 Hz, 1 H), 7.18 (d, J=8.5 Hz, 1 H), 7.32 (s, 1 H), 7.74 (d, J=1.0 Hz, 1 H); MS: (ESI) m/z 370.2 (M+H)$^+$.

Example 8 a) N-(5-Oxo-5,6,7,8-tetrahydro-naphthalen-2-yl)-acetamide

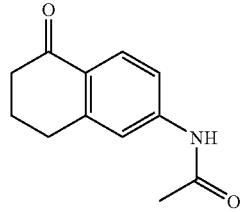

To a solution of 6-amino-3,4-dihydro-2H-naphthalen-1-one (CAS#3470-53-9, 0.875 g, 5.44 mmol) in pyridine (5 mL) is added acetic anhydride (0.83 g, 8.16 mmol). After 1 hour, the solution is diluted with dichloromethane and washed with water and 1M aqueous HCl. The organic phase is dried over sodium sulfate, filtered, and concentrated to give N-(5-oxo-5,6,7,8-tetrahydro-naphthalen-2-yl)-acetamide; $^1$H NMR (400 MHz, CDCl$_3$) δ ppm 2.09-2.16 (m, 2 H), 2.22

(s, 3 H), 2.59-2.67 (m, 2 H), 2.95 (t, J=6.1 Hz, 2 H), 7.21 (dd, J=8.3, 2.1 Hz, 1 H), 7.42 (br. s., 1 H), 7.70 (br. s., 1 H), 8.00 (d, J=8.3 Hz, 1 H).

b) 3-(6-Acetylamino-1,2,3,4-tetrahydro-naphthalen-1-yl)-3H-imidazole-4-carboxylic acid isopropyl ester

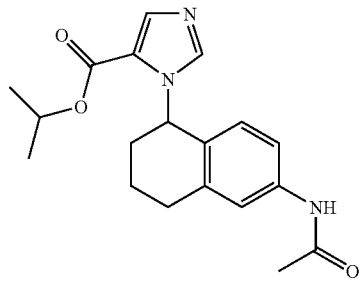 [SMILES: CC(=O)Nc1ccc2c(c1)CCCC2n1cncc1C(=O)OC(C)C]

To a solution of N-(5-oxo-5,6,7,8-tetrahydro-naphthalen-2-yl)-acetamide (1.00 g, 4.94 mmol) in methanol (20 mL) at 0° C. is added sodium borohydride (0.50 g, 7.41 mmol). The reaction is stirred for 1.5 hours, whereupon water is added and the volatiles are removed in vacuo. The mixture is extracted with dichloromethane and the organic phase is dried over sodium sulfate, filtered, and concentrated to give N-(5-hydroxy-5,6,7,8-tetrahydro-naphthalen-2-yl)-acetamide, which is used in the next step without further purification.

To a suspension of N-(5-hydroxy-5,6,7,8-tetrahydro-naphthalen-2-yl)-acetamide (0.553 g, 2.69 mmol) and isopropyl 4-imidazolecarboxylate (0.290 g, 1.88 mmol), which can be prepared as described in Example 1, in THF (10 mL) at 0° C. is added triphenylphosphine (1.415 g, 5.39 mmol) and dimethyl azodicarboxylate (40% wt. in toluene, 1.97 g, 5.39 mmol). The cooling bath is removed and the mixture is stirred for 15 min. Water is added and the mixture is extracted with ethyl acetate. The organic phase is dried over sodium sulfate, filtered and concentrated. The resulting residue is purified by silica gel chromatography (elution with dichloromethane-methanol mixtures) to give 3-(6-acetylamino-1,2,3,4-tetrahydro-naphthalen-1-yl)-3H-imidazole-4-carboxylic acid isopropyl ester; MS: (ESI) m/z 342.2 (M+H)+; 1H NMR (400 MHz, MeOD) δ ppm 1.39 (d, J=6.3 Hz, 3 H), 1.40 (d, J=6.0 Hz, 3 H), 1.71-1.82 (m, 1 H), 1.83-1.92 (m, 1 H), 2.16 (s, 3H), 2.17-2.30 (m, 2 H), 2.86 (ddd, J=16.9, 8.3; 5.6 Hz, 1 H), 3.00 (dt, J=16.9, 5.6 Hz, 1 H), 5.25 (sept., J=6.3 Hz, 1 H), 6.30 (t, J=5.3 Hz, 1 H), 6.93 (d, J=8.3 Hz, 1 H), 7.34-7.36 (m, 2 H), 7.53 (d, J=1.8 Hz, 1 H), 7.74 (d, J=1.0 Hz, 1 H).

d) (R)- and (S)-3-(6-Acetylamino-1,2,3,4-tetrahydro-naphthalen-1-yl)-3H-imidazole-4-carboxylic acid isopropyl ester Resolution of the enantiomers of the title compound is achieved by chiral HPLC using the ChiralPak IA column with a hexanes-ethanol 17:3 mobile phase to give (R)-3-(6-Acetylamino-1,2,3,4-tetrahydro-naphthalen-1-yl)-3H-imidazole-4-carboxylic acid isopropyl ester (t$_r$=12.8 min) and (S)-3-(6-Acetylamino-1,2,3,4-tetrahydro-naphthalen-1-yl)-3H-imidazole-4-carboxylic acid isopropyl ester (t$_r$=33.4 min).

Example 9 a) 7-Bromo-5-fluoro-3,4-dihydro-2H-naphthalen-1-one

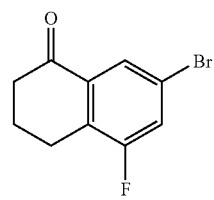 [SMILES: O=C1CCCc2c(F)cc(Br)cc21]

To a suspension of (2-carboxyethyl)triphenylphosphonium bromide (CAS#51114-94-4, 1.822 g, 4.256 mmol) and 2-fluoro-4-bromobenzaldehyde (CAS#188813-02-7, 0.900 g, 4.256 mmol) in THF (4 mL) and DMSO (4 mL) under nitrogen is added NaH (60% suspension in mineral oil, 0.34 g, 8.511 mmol). After 1.5 hours, the mixture is quenched with 1M aqueous potassium bisulfate and extracted with isopropyl acetate. The combined organic phase is washed with brine, dried over MgSO$_4$, filtered, and concentrated. The resulting residue is used in the next step without further purification.

To a solution of (E)-4-(4-bromo-2-fluoro-phenyl)-but-3-enoic acid (0.730 g, 2.536 mmol) in ethyl acetate (12 mL) is added palladium on carbon (10% wt., 0.270 g, 0.254 mmol) and the flask is flushed with hydrogen. After 16 hours under a H$_2$ atmosphere (balloon pressure), the mixture is filtered, concentrated and then resubmitted to the same conditions. After 6 hours, the mixture is filtered and concentrated to give 4-(4-bromo-2-fluoro-phenyl)-butyric acid, which is used in the next step without purification.

To a solution of 4-(4-bromo-2-fluoro-phenyl)-butyric acid (0.625 g, 2.154 mmol) and DMF (0.0084 g, 0.108 mmol) in dichloromethane (10 mL) is added oxalyl chloride (0.558 g, 4.309 mmol). The mixture is stirred for 30 min and concentrated in vacuo at room temperature to give a yellow oil, which is re-dissolved in dichloromethane (20 mL) and added dropwise to aluminum chloride (0.402 g, 3.016 mmol) in dichloromethane (20 mL). The mixture is refluxed for 3.5 hours, and then poured into ice-water. The resulting mixture is extracted twice with diethyl ether. The organic phases are combined, washed with saturated aqueous NaHCO$_3$, dried over MgSO$_4$, filtered through a cotton plug, and concentrated. The resulting residue is purified by silica gel flash chromatography (hexanes-ethyl acetate, 19:1 to 9:1) to afford 7-bromo-5-fluoro-3,4-dihydro-2H-naphthalen-1-one; 1H NMR (400 MHz, CDCl$_3$) δ ppm 2.13-2.19 (m, 2 H), 2.67 (t, J=6.6 Hz, 2 H), 2.90 (t, J=6.2 Hz, 2 H), 7.40 (dd, J=8.5, 1.9 Hz, 1 H), 7.98 (s, 1 H).

b) 3-(7-Bromo-5-fluoro-1,2,3,4-tetrahydro-naphthalen-1-yl)-3H-imidazole-4-carboxylic acid isopropyl ester

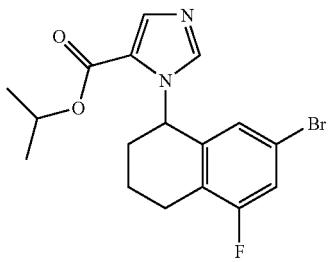 [SMILES: CC(C)OC(=O)c1cncn1C1CCCc2c(F)cc(Br)cc21]

To a solution of 7-bromo-5-fluoro-3,4-dihydro-2H-naphthalen-1-one (0.290 g, 1.145 mmol) in methanol (8 mL) and dichloromethane (2 mL) at 0° C. is added sodium borohydride (0.066 g, 1.718 mmol) in one portion. After 2 hours at 0° C., water (30 mL) is added and the volatile organics are removed in vacuo. The resulting mixture is extracted with dichloromethane, dried over magnesium sulfate, filtered, and concentrated to afford 7-bromo-5-fluoro-3,4-dihydro-2H-naphthalen-1-ol, which is used in the next step without further purification.

To a solution of 7-bromo-5-fluoro-3,4-dihydro-2H-naphthalen-1-ol (0.280 g, 1.10 mmol) and isopropyl 4-imidazolecarboxylate (0.121 g, 0.77 mmol), which can be prepared as described in Example 1, in THF (6 mL) at 0° C. is added triphenylphosphine (0.291 g, 1.10 mmol) and methyl azodicarboxylate (40% in toluene, 0.41 mL, 1.10 mmol). After 1 hour, the cooling bath is removed and after another hour, the mixture is diluted with ethyl acetate and washed with half-saturated brine, dried over magnesium sulfate, filtered, t and concentrated. The resulting residue is purified by semi-preparative reverse phase HPLC (5 to 100% acetonitrile/water w/0.1% TFA) to furnish affords a pale yellow oil. After free-basing, 3-(7-bromo-5-fluoro-1,2,3,4-tetrahydro-naphthalen-1-yl)-3H-imidazole-4-carboxylic acid isopropyl ester is obtained; MS: (ESI) m/z 381.1, 383.0 (M+H)$^+$; $^1$H NMR (400 MHz, CDCl$_3$) δ ppm 1.37 (d, J=6.3 Hz, 3 H), 1.39 (d, J=6.3 Hz, 3 H), 1.71-1.81 (m, 1 H), 1.83-1.92 (m, 1 H), 2.07-2.24 (m, 2 H), 2.72 (dt, J=17.7, 6.8 Hz, 1 H), 2.87 (dd, J=17.7, 5.8 Hz, 1 H), 5.22 (sept, J=6.3 Hz, 1 H), 6.29 (t, J=5.2 Hz, 1 H), 6.94 (br. s, 1 H), 7.18 (dd, J=8.8, 1.8 Hz, 1 H), 7.22 (s, 1 H), 7.79 (s, 1 H).

Example 10 a) 2,2-Dimethyl-indan-1-ol

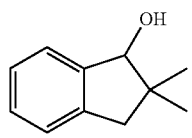

To a solution of 2,2-dimethyl-indan-1-one, which can be prepared as described in Ranu, B. C.; Jana, U. *Journal of Organic Chemistry,* 1999, 64, 6380-6386, (13.0 g, 81.3 mmol) in methanol (200 mL) at −20° C. is added NaBH$_4$ (3.07 g, 81.3 mmol). Upon complete consumption of the starting ketone, as determined by TLC analysis, the reaction is quenched with saturated aqueous NH$_4$Cl. The reaction mixture is then concentrated to near dryness, diluted with ethyl acetate and washed with water. The organic layer is then dried with Na$_2$SO$_4$, filtered, and concentrated. The resulting residue is purified by silica gel flash chromatography (ethyl acetate-heptane, 0:1 to 1:8) to provide 2,2-dimethyl-indan-1-ol. $^1$H NMR (400 MHz, CDCl$_3$) δ ppm 1δ ppm 1.05 (s, 3 H), 1.20 (s, 3 H), 2.56-2.89 (m, 2 H), 4.70 (s, 1 H), 7.16-7.26 (m, 3 H), 7.35-7.42 (m, 1 H).

b) 3-(2,2-Dimethyl-indan-1-yl)-3H-imidazole-4-carboxylic acid methyl ester

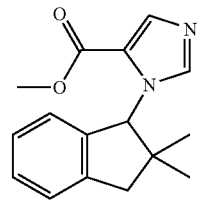 [SMILES: COC(=O)c1cncn1C1c2ccccc2CC1(C)C]

To a solution of 2,2-dimethyl-indan-1-ol (3.5 g, 21.6 mmol) in THF (160 mL) is added methyl 4-imidazolecarboxylate (CAS#17325-26-7, 4.1 g, 32.3 mmol), and triphenylphosphine (9.09 g, 34.5 mmol). The reaction is cooled to 0° C. and diisopropyl azodicarboxylate (6.67 mL, 34.5 mmol) is added. After one hour the reaction is diluted with saturated aqueous NaHCO$_3$ and ethyl acetate. The layers are separated and the organic layer is dried with Na$_2$SO$_4$, filtered, and concentrated. The resulting residue is purified by silica gel flash chromatography (ethyl acetate-dichloromethane, 0:1 to 1:1) to provide 3-(2,2-dimethyl-indan-1-yl)-3H-imidazole-4-carboxylic acid methyl ester. HRMS: (ESI) m/z 271.1440 [(M+H)$^+$: Calcd for C$_{16}$H$_{19}$N$_2$O$_2$: 271.1447]; $^1$H NMR (400 MHz, CDCl$_3$) δ ppm 2.60-3.08 (m, 2 H), 3.92 (s, 3 H), 6.25 (s, 1 H), 7.03 (s, 1 H), 7.15-7.46 (m, 4 H), 7.80 (d, J=1.0 Hz, 1 H). The HCl salt of the title compound can be prepared by dissolution in diethyl ether followed by treatment with an excess of 1N HCl in diethyl ether. The resulting heterogeneous solution is concentrated to furnish the HCl salt of 3-(2,2-dimethyl-indan-1-yl)-3H-imidazole-4-carboxylic acid methyl ester.

The Following Compounds can be Prepared in a Similar Fashion as Example 10

(R)- and (S)-3-(2,2-Dimethyl-1,2,3,4-tetrahydro-naphthalen-1-yl)-3H-imidazole-4-carboxylic acid methyl ester

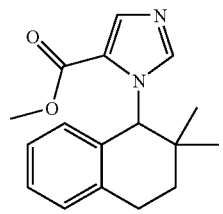

$^1$H NMR (400 MHz, MeOD) of the HNO$_3$ salt: δ ppm 0.87 (s, 3 H), 1.17 (s, 3 H), 1.67-1.74 (m, 1 H), 1.80-1.88 (m, 1 H), 2.97-3.15 (m, 2 H), 4.06 (s, 3 H), 6.57 (s, 1 H), 7.09 (d, J=7.8 Hz, 1 H), 7.22-7.26 (m, 1 H), 7.32-7.40 (m, 2 H), 8.32 (d, J=1.3 Hz, 1 H), 8.61 (s, 1 H); MS: (ESI) m/z 285.1 (M+H)$^+$.

Resolution of the enantiomers of the free base of the title compound is achieved by chiral HPLC using a ChiralPak IA column with a 1:4 ethyl acetate-hexanes mobile phase to provide (R)-3-(2,2-Dimethyl-1,2,3,4-tetrahydro-naphthalen-1-yl)-3H-imidazole-4-carboxylic acid methyl ester (t$_r$=12.7 min) and (S)-3-(2,2-Dimethyl-1,2,3,4-tetrahydro-naphthalen-1-yl)-3H-imidazole-4-carboxylic acid methyl ester (t$_r$=14.8 min).

3-(2,2-Dimethyl-indan-1-yl)-3H-imidazole-4-carboxylic acid oxetan-3-yl ester

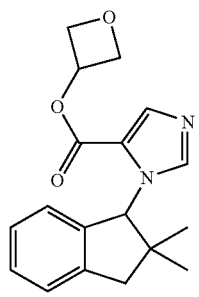 [SMILES: CC1(C)Cc2ccccc2C1n1cncc1C(=O)OC1COC1]

The title compound can be prepared by employing 3H-imidazole-4-carboxylic acid oxetan-3-yl ester in Step 3 of Scheme 1. 3H-imidazole-4-carboxylic acid oxetan-3-yl ester can be prepared as described in Part a of Example 1 by using oxetan-3-ol (CAS#7748-36-9) in place of isopropanol.

MS: (ESI) m/z 313.2 (M+H)$^+$; $^1$H NMR (400 MHz, CDCl$_3$) of the free base δ ppm 0.74 (s, 3 H), 1.24 (s, 3 H), 2.65-3.04 (m, 2 H), 4.82 (t, J=6.4 Hz, 2 H), 5.01 (t, J=6.9 Hz, 2 H), 5.60-5.73 (m, 1 H), 6.17 (s, 1 H), 7.04 (s, 1 H), 7.20-7.41 (m, 4 H), 7.89 (s, 1 H).

cis- and trans-3-[3-(4-Methoxy-phenyl)-2,2-dimethyl-indan-1-yl]-3H-imidazole-4-carboxylic acid methyl ester

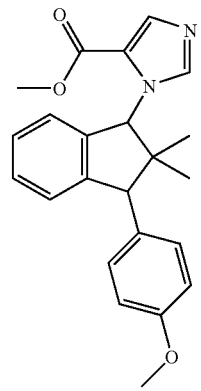 [SMILES: COC(=O)c1cncn1C1c2ccccc2C(c2ccc(OC)cc2)C1(C)C]

The requisite ketone, 3-(4-methoxy-phenyl)-indan-1-one (CAS #53786-92-8), for the construction of the title compound via the method described in Example 10 can be prepared as described by Barltrop, J. A.; et al. *Journal of the Chemical Society*, 1956, 2928-2940.

~10:1 diastereomeric mixture: MS: (ESI) m/z 377.2 (M+H); Major Diastereomer: $^1$H NMR (400 MHz, CDCl$_3$) of the free base δ ppm 0.75 (s, 3 H), 0.85 (s, 3 H), 3.83 (s, 3 H), 3.91 (s, 3 H), 4.23 (s, 1 H), 6.34 (s, 1 H), 6.86-6.92 (m, 2 H), 6.98 (s, 1 H), 7.02-7.06 (m, 2 H), 7.18 (d, J=7.6 Hz, 1 H), 7.30-7.44 (m, 3 H), 7.82 (d, J=1.0 Hz, 1 H); Minor Diastereomer: $^1$H NMR (400 MHz, CDCl$_3$) of the free base δ ppm 0.78 (s, 3 H), 0.89 (s, 3 H), 3.80 (s, 3 H), 3.90 (s, 3 H), 4.98 (s, 1 H), 6.38 (s, 1 H), 6.85-7.45 (m, 9 H), 7.78-7.84 (m, 1 H).

cis- or trans-3-[4-(4-Methoxy-phenyl)-2,2-dimethyl-1,2,3,4-tetrahydro-naphthalen-1-yl]-3H-imidazole-4-carboxylic acid methyl ester

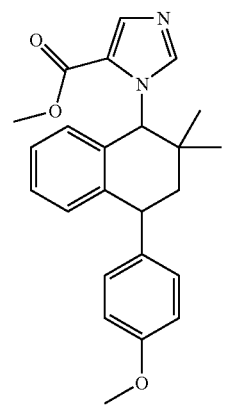

The requisite ketone, 4-(4-Methoxy-phenyl)-3,4-dihydro-2H-naphthalen-1-one (CAS #120133-20-2), for the construction of the title compound via the method described in Example 10 can be prepared as described by Murphy, W. S.; Kesra, A. *Journal of Chemical Research Synopses*, 1988, 10, 318-319.

MS: (ESI) m/z 391.2 (M+H)+; 1H NMR (400 MHz, CDCl3) of the free base δ ppm 0.98 (s, 3 H), 1.08 (s, 3 H), 1.96-2.11 (m, 2 H), 3.82 (s, 3 H), 3.91 (s, 3 H), 4.21 (dd, J=11.49, 6.19 Hz, 1 H), 6.54-6.61 (m, 1 H), 6.76 (br. s., 1 H), 6.83-6.93 (m, 3 H), 7.04-7.15 (m, 4 H), 7.55 (s, 1 H), 7.90 (s, 1 H).

Example 11 a) 2,2-Dimethyl-benzofuran-3-one

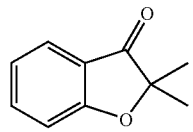

To a heterogeneous solution of a 60% oil dispersion of NaH (600 mg, 15.0 mmol) in THF (25 mL) at −30° C. is added dropwise a solution of benzofuran-3-one (CAS#7169-34-8, 670 mg, 5 mmol) in THF (10 mL). The reaction is allowed to stir at −30° C. for 20 min, at which time iodomethane (0.93 mL, 15 mmol) is added dropwise. The reaction is permitted to warm to room temperature and is then quenched with 2N aqueous HCl and diluted with ethyl acetate. The layers are separated and the aqueous layer is extracted two more times with ethyl acetate. The organic layers are combined, dried with Na2SO4, filtered, and concentrated. The resulting residue is purified by silica gel flash chromatography (ethyl acetate-heptane, 1:10) to provide 2,2-dimethyl-benzofuran-3-one. MS: (ESI) m/z 163.0 (M+H)+.

b) 2,2-Dimethyl-2,3-dihydro-benzofuran-3-ol

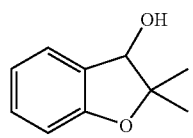

To a solution of 2,2-dimethyl-benzofuran-3-one (1.58 g, 9.7 mmol) in methanol (30 mL) at 0° C. is added NaBH4 (0.36 g, 9.7 mmol). The reaction is placed at room temperature and another equivalent of NaBH4 (0.36 g, 9.7 mmol) is added. After three hours the reaction is quenched with saturated aqueous NH4Cl. The reaction is concentrated to approximately ¾ of its original volume, diluted with ethyl acetate, and washed with 2N aqueous HCl, followed by brine. The organic layer is dried with Na2SO4, filtered, and concentrated. The resulting residue is purified by silica gel flash chromatography (ethyl acetate-heptane, 0:1 to 1:8) to provide 2,2-dimethyl-2,3-dihydro-benzofuran-3-ol; 1H NMR (400 MHz, CDCl3) δ ppm 1.34 (s, 3 H), 1.49 (s, 3 H), 1.96 (d, J=8.6 Hz, 1 H), 4.71 (d, J=8.6 Hz, 1 H), 6.79 (d, J=8.1 Hz, 1 H), 6.87-6.95 (m, 1 H), 7.21-7.26 (m, 1 H), 7.39 (d, J=7.3 Hz, 1 H).

c) 3-(2,2-Dimethyl-2,3-dihydro-benzofuran-3-yl)#H-imidazole-4-carboxylic acid methyl ester

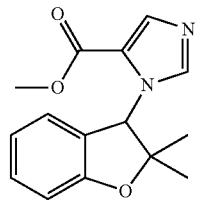 [SMILES: COC(=O)c1cncn1C1c2ccccc2OC1(C)C]

To a solution of 2,2-dimethyl-2,3-dihydro-benzofuran-3-ol (375 mg, 2.28 mmol) in THF (20 mL) is added methyl 4-imidazolecarboxylate (CAS#17325-26-7, 432 mg, 3.42 mmol), followed by triphenylphosphine (896 mg, 3.42 mmol). The reaction is cooled to 0° C. and di-t-butyl azodicarboxylate (787 mg, 3.42 mmol) is added. The reaction is permitted to warm to room temperature and stirred for 2 hours. The reaction mixture is then cooled to 0° C. and quenched with 4 N HCl in dioxane (5 mL, 20 mmol) and stirred for 30 minutes. The reaction is concentrated to near dryness and diluted with ethyl acetate. The organic layer is extracted three times with 1 N aqueous HCl. The aqueous extracts are combined, neutralized with Na2CO3, and extracted three times with ethyl acetate. The combined organic layers are dried with Na2SO4, filtered and concentrated. The resulting residue is purified by silica gel flash chromatography (ethyl acetate-dichloromethane, 0:1 to 1:5) to furnish 3-(2,2-dimethyl-2,3-dihydro-benzofuran-3-yl)-3H-imidazole-4-carboxylic acid methyl ester; HRMS: (ESI) m/z 245.0934 [(M+H)+: Calcd for C13H13N2O3: 245.0926]; 1H NMR (400 MHz, CDCl3) δ ppm 1.05 (s, 3H), 1.57 (s, 3 H), 3.92 (s, 3 H), 6.32 (s, 1 H), 6.92 (d, J=8.1 Hz, 1 H), 6.95-7.02 (m, 2 H), 7.25 (s, 1 H), 7.32-7.40 (m, 1 H), 7.80 (s, 1 H).

Example 12 a) 7-Iodo-isothiochroman-4-one

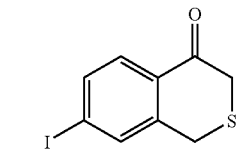 [SMILES: O=C1CSCc2cc(I)ccc21]

To a solution of 1-bromomethyl-3-iodo-benzene (CAS#49617-83-6, 25.0 g, 84 mmol) in acetone (500 mL) is added mercapto-acetic acid methyl ester (9.0 g, 85 mmol) followed by K2CO3 (15.2 g 110 mmol). The reaction is permitted to stir overnight. The next morning the reaction is filtered and concentrated. The resulting residue containing (3-iodo-benzylsulfanyl)-acetic acid methyl ester is then dissolved in methanol (300 mL). The methanol solution is charged with water (100 mL) and lithium hydroxide (6.0 g, 252 mmol). The reaction is permitted to stir at room temperature until the starting ester is consumed as determined by TLC analysis. The reaction is then brought to a pH<4 by the addition of 3N aqueous HCl. The reaction is then concentrated to approximately ¾ of its original volume and diluted with ethyl acetate. The layers are separated and the organic layer is dried with Na$_2$SO$_4$, filtered and concentrated to afford a residue containing 3-iodo-benzylsulfanyl)-acetic acid. The residue is dissolved in chlorobenzene (500 mL) and treated with P$_2$O$_5$ (64 g, 450 mmol). The reaction is heated at reflux overnight. The reaction is then cooled to room temperature and filtered. The eluent is then concentrated to dryness. The resulting residue is dissolved in ethyl acetate and washed with brine. The organic layer is then dried with Na$_2$SO$_4$, filtered, and concentrated. The resulting residue is purified by silica gel flash chromatography (ethyl acetate-hexanes, 0:1 to 1:5) to afford 7-iodo-isothiochroman-4-one; MS: (ESI) m/z 308.0 (M+NH$_4$)+ b) 4-Oxo-isothiochroman-7-carbonitrile

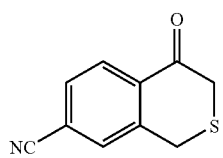

To a solution of 7-iodo-isothiochroman-4-one (290 mg, 1.0 mmol) in DMF (5 mL) is added Zn(CN)$_2$ (117 mg, 1.0 mmol) and Pd(PPh$_3$)$_4$ (124 mg, 0.1 mmol). The reaction is then heated to 95° C. for 3 hours, at which time it is cooled to room temperature and concentrated to dryness. The resulting residue is purified by silica gel flash chromatography (ethyl acetate-dichloromethane, 1:10 to 3:10) to furnish 4-oxo-isothiochroman-7-carbonitrile; MS: (ESI) m/z 188.2 (M–H)$^-$.

c) 4-Hydroxy-isothiochroman-7-carbonitrile

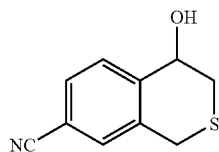

To a solution of 4-oxo-isothiochroman-7-carbonitrile (830 mg, 4.4 mmol) in methanol (25 mL) at 0° C. is added NaBH$_4$ (330 mg, 8.8 mmol). The reaction is permitted to stir for 1 hour and then quenched with 1N aqueous HCl. The reaction is concentrated to approximately half of its original volume and diluted with ethyl acetate. The organic layer is separated, dried with Na$_2$SO$_4$, filtered and concentrated. The resulting residue is purified by silica gel flash chromatography (ethyl acetate-hexanes, 0:1 to 1:1) to afford 4-hydroxy-isothiochroman-7-carbonitrile; MS: (ESI) m/z 192.1 (M+H)$^+$.

d) 3-(7-Cyano-isothiochroman-4-yl)-3H-imidazole-4-carboxylic acid methyl ester

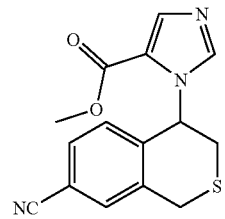

To a solution of 4-hydroxy-isothiochroman-7-carbonitrile (630 mg, 3.3 mmol) in THF (20 mL) is added methyl 4-imidazolecarboxylate (CAS#17325-26-7, 460 mg, 3.6 mmol), and triphenylphosphine (909 mg, 3.4 mmol). The reaction is cooled to 0° C. and diisopropyl azodicarboxylate (0.66 mL, 3.4 mmol) is added. The reaction is permitted to warm to room temperature and stirred until LC-MS analysis indicates complete consumption of 4-hydroxy-isothiochroman-7-carbonitrile. The reaction mixture is diluted with saturated aqueous NaHCO$_3$ and ethyl acetate. The layers are separated and the organic layer is dried with Na$_2$SO$_4$, filtered and concentrated. The resulting residue is purified by silica gel flash chromatography (ethyl acetate-dichloromethane, 0:1 to 1:1) to provide 3-(7-cyano-isothiochroman-4-yl)-3H-imidazole-4-carboxylic acid methyl ester; MS: (ESI) m/z 300.1 (M+H). $^1$H NMR (400 MHz, CDCl$_3$) δ ppm 3.08-3.23 (m, 1 H), 3.32 (dd, J=14.4, 4.0 Hz, 1 H), 3.73-4.07 (m, 2 H), 3.91 (s, 3 H), 6.46-6.61 (m, 1 H), 7.15 (d, J=8.1 Hz, 1 H), 7.46 (s, 1 H), 7.49-7.54 (m, 1 H), 7.56 (s, 1 H), 7.84 (s, 1 H). The HCl salt of the title compound can be prepared by dissolution in diethyl ether followed by treatment with an excess of 1N HCl in diethyl ether. The resulting heterogeneous solution is concentrated to furnish the HCl salt of 3-(7-cyano-isothiochroman-4-yl)-3H-imidazole-4-carboxylic acid methyl ester.

Example 13 a) Acetic acid 2,2-dimethyl-1,2,3,4-tetrahydro-naphthalen-1-yl ester

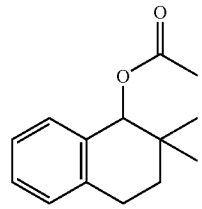 [SMILES: CC(=O)OC1c2ccccc2CCC1(C)C]

To a suspension of 60% NaH in an oil dispersion (20 g, 500 mmol) in THF (600 mL) at 0° C. is added a solution of α-tetralone (24.8 g, 166.5 mmol) in THF (40 mL) via cannula, followed by iodomethane (119 g, 833 mmol). The reaction is permitted to warm to room temperature and after one hour is quenched with 1 M aqueous sodium bisulfate. The reaction mixture is partitioned between water and ethyl acetate and the organic layer is washed with brine, dried over magnesium sulfate, filtered and concentrated. The resulting residue is then dissolved in methanol (600 mL) and dichloromethane (100 mL). Sodium borohydride (37.8 g, 262 mmol) is then added in five portions over 20 minutes. After one hour the reaction is diluted with water, and the organic solvents are then evaporated in vacuo. The resulting mixture is extracted with ethyl acetate, and the organic extract is dried with magnesium sulfate, filtered and concentrated. The resulting residue is then dissolved in dichloromethane (300 mL). To the resulting solution is added triethylamine (50 g, 490 mmol) and 4-dimethylaminopyridine (4 g, 33 mmol). The reaction is cooled to 0° C. and charged with acetic anhydride (42 g, 408 mmol). The reaction is permitted to stir for 10 minutes, then is diluted with ethyl acetate, and washed with 1 M aqueous $NaHSO_{4}$, followed by saturated aqueous $NaHCO_3$. The organic phase is dried with magnesium sulfate, filtered, and concentrated. The resulting oil is then purified by distillation (110° C. at 0.2 torr) to furnish acetic acid 2,2-dimethyl-1,2, 3,4-tetrahydro-naphthalen-1-yl ester; $^1H$ NMR (400 MHz, $CDCl_3$) δ ppm 0.95 (s, 3 H), 1.01 (s, 3 H), 1.50-1.63 (m, 1 H), 1.84-1.99 (m, 1 H), 2.10 (s, 3 H), 2.76-2.94 (m, 2 H), 5.74 (s, 1 H), 7.08-7.31 (m, 4 H).

b) Acetic acid 2,2-dimethyl-4-oxo-1,2,3,4-tetrahydro-naphthalen-1-yl ester

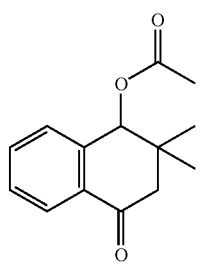 [SMILES: CC(=O)OC1c2ccccc2C(=O)CC1(C)C]

To a solution of 2,2-dimethyl-1,2,3,4-tetrahydro-naphthalen-1-yl ester (380 mg, 1.71 mmol) in 1,2-dichloroethane (7 mL) is added dirhodium (II) tetrakis(caprolactam) [$Rh_2(cap)_4$, CAS#138984-26-6] (15 mg, 0.017 mmol) followed by a 5.5 M decane solution of t-butyl hydroperoxide [TBHP] (3.1 mL, 17.1 mmol). The reaction mixture is placed at 40° C. After four hours the reaction is charged with additional $Rh_2(cap)_4$ (7.5 mg, 0.008 mmol) and TBHP (1.55 mL, 8.53 mmol). After stirring at 40° C. for an additional 20 hours the reaction mixture is charged again with $Rh_2(cap)_4$ (7.5 mg, 0.008 mmol) and TBHP (1.55 mL, 8.53 mmol). After a total of 48 hours the reaction is cooled to room temperature, diluted with water and extracted twice with dichloromethane. The organic extracts are then treated with 1.6 M aqueous $FeSO_4$ and the resulting biphasic solution is permitted to stir for 30 minutes, at which time the layers are separated and the organic layer is dried with magnesium sulfate, filtered and concentrated. The resulting residue is purified by silica gel flash chromatography (ethyl acetate-hexanes, 1:9 to 1:4) to provide acetic acid 2,2-dimethyl-4-oxo-1,2,3,4-tetrahydro-naphthalen-1-yl ester; $^1H$ NMR (400 MHz, $CDCl_3$) δ ppm 1.04 (s, 3H), 1.09 (s, 3 H), 2.14 (s, 3 H), 2.45-2.53 (m, 1 H), 2.85 (d, J=17.2 Hz, 1 H), 5.94 (s, 1 H), 7.38-7.49 (m, 2 H), 7.54-7.64 (m, 1 H), 8.05 (dd, J=7.7, 1.4 Hz, 1 H).

c) 4-Hydroxy-3,3-dimethyl-3,4-dihydro-2H-naphthalen-1-one

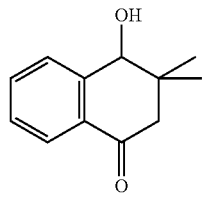

To a solution of acetic acid 2,2-dimethyl-4-oxo-1,2,3,4-tetrahydro-naphthalen-1-yl ester (4.03 g, 16.7 mmol) in methanol (50 mL) and dichloromethane (10 mL) is added potassium carbonate (2.33 g, 16.66 mmol). The reaction is permitted to stir for 8 hours at which time it is diluted with ethyl acetate and the resulting solution is washed successively with water and brine. The aqueous phases are then back-extracted with dichloromethane and the organic phases are then combined, dried over magnesium sulfate, filtered, and concentrated to furnish 4-hydroxy-3,3-dimethyl-3,4-dihydro-2H-naphthalen-1-one; $^1H$ NMR (400 MHz, $CDCl_3$) δ ppm 1.04 (s, 3 H), 1.11 (s, 3 H), 2.07 (d, J=6.1 Hz, 1 H), 2.46 (d, J=16. 7 Hz, 1 H), 2.78 (d, J=16.7 Hz, 1 H), 4.64 (d, J=5.8 Hz, 1 H), 7.38-7.46 (m, 1 H), 7.59-7.63 (m, 2 H), 8.02 (d, J=7.8 Hz, 1 H).

d) 3-(2,2-Dimethyl-4-oxo-1,2,3,4-tetrahydro-naphthalen-1-yl)-3H-imidazole-4-carboxylic acid methyl ester

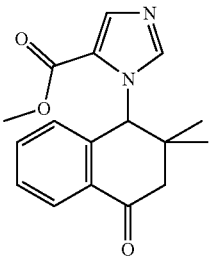

To a solution of 4-hydroxy-3,3-dimethyl-3,4-dihydro-2H-naphthalen-1-one (2.87 g, 13.88 mmol) and methyl 4-imidazolecarboxylate (CAS#17325-26-7, 1.25 g, 9.72 mmol) in THF (80 mL) at 0° C. is added triphenylphosphine (3.68 g, 13.88 mmol) and dimethyl azodicarboxylate (40% in toluene, 5.14 mL, 13.88 mmol) and the cooling bath is removed. After 15 hours, the mixture is concentrated and the resulting residue is dissolved in ethyl acetate (250 mL) and is extracted five times with 1M aqueous HCl (40 mL portions). The acidic aqueous phases are cooled to 0° C. and the pH is adjusted to ca. 12 with 4M aqueous NaOH at 0° C. The aqueous phase is then extracted three times with dichloromethane. The combined organic layers are dried over $MgSO_4$ and filtered, and concentrated. The resulting residue is purified by silica gel flash chromatography (dichloromethane-methanol, 49:1) to give 3-(2,2-dimethyl-4-oxo-1,2,3,4-tetrahydro-naphthalen- 1-yl)-3H-imidazole-4-carboxylic acid methyl ester; MS: (ESI) m/z 299.0 (M+H)+; $^1$H NMR (400 MHz, CDCl$_3$) δ ppm 0.97 (s, 3 H), 1.15 (s, 3 H), 2.63 (d, J=16.8 Hz, 1 H), 2.74 (d, J=16.8 Hz, 1 H), 3.93 (s, 3 H), 6.79 (s, 1 H), 7.02 (d, J=7.6 Hz, 1 H), 7.35 (s, 1 H), 7.47 (t, J=7.6 Hz, 1 H), 7.55 (td, J=7.6, 1.5 Hz, 1 H), 7.86 (s, 1 H), 8.13 (dd, J=7.6, 1.5 Hz, 1 H);

e) (R)- and (S)-3-(2,2-Dimethyl-4-oxo-1,2,3,4-tetrahydro-naphthalen-1-yl)-3H-imidazole-4-carboxylic acid methyl ester The resolution of the enantiomers the title compound is achieved by chiral HPLC using a ChiralPak IA column with 7:3 hexanes:reagent alcohol to give (R)-3-(2,2-Dimethyl-4-oxo-1,2,3,4-tetrahydro-naphthalen-1-yl)-3H-imidazole-4-carboxylic acid methyl ester (t$_r$=14.7 min) and (S)-3-(2,2-Dimethyl-4-oxo-1,2,3,4-tetrahydro-naphthalen-1-yl)-3H-imidazole-4-carboxylic acid methyl ester (t$_r$=20.9 min).

Example 14 a) 7-Methoxy-2,2-dimethyl-3,4-dihydro-2H-naphthalen-1-one

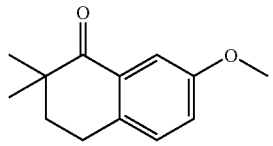

A solution of 7-methoxy-3,4-dihydro-2H-naphthalen-1-one (CAS#6836-19-7, 2.00 g, 11.24 mmol) in THF (20 mL) is cannulated to a suspension of NaH (60%, 1.35 g, 33.71 mmol) in THF (60 mL) at 0° C. under nitrogen. After 45 min at 0° C., iodomethane (8.05 g, 56.18 mmol) is added dropwise and the cooling bath is removed. After 19 hours, the mixture is quenched with 1M aqueous sodium bisulfate and then partitioned between water and diethyl ether. The aqueous layer is extracted once with diethyl ether. The combined organic phases are dried over magnesium sulfate, filtered, and concentrated. The resulting residue is purified by silica gel flash chromatography (hexanes-ethyl acetate, 97:3) to afford 7-methoxy-2,2-dimethyl-3,4-dihydro-2H-naphthalen-1-one; $^1$H NMR (400 MHz, CDCl$_3$) δ ppm 1.22 (s, 6 H), 1.97 (t, J=6.3 Hz, 2 H), 2.93 (t, J=6.3 Hz, 2 H), 3.84 (s, 3 H), 7.05 (dd, J=8.3, 2.8 Hz, 1 H), 7.14 (d, J=8.3 Hz, 1 H), 7.54 (d, J=2.8 Hz, 1 H).

b) Acetic acid 7-methoxy-2,2-dimethyl-4-oxo-1,2,3,4-tetrahydro-naphthalen-1-yl ester

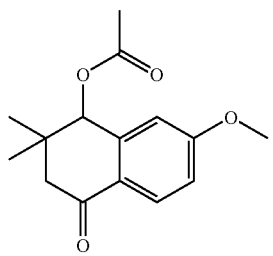

To a solution of 7-methoxy-2,2-dimethyl-3,4-dihydro-2H-naphthalen-1-one (1.42 g, 6.81 mmol) in methanol (15 mL) and dichloromethane (5 mL) is added NaBH$_4$ (1.04 g, 27.25 mmol) in one portion. After 15 min, water is added and the organic solvents are evaporated in vacuo. The aqueous layer is extracted with ethyl acetate. The combined organic phases are dried over magnesium sulfate, filtered, and concentrated to give 7-methoxy-2,2-dimethyl-3,4-dihydro-2H-naphthalen-1-ol, which is used in the next step without further purification.

To a solution of 7-methoxy-2,2-dimethyl-3,4-dihydro-2H-naphthalen-1-ol (1.40 g, 6.52 mmol) and DMAP (0.16 g, 1.30 mmol) in dichloromethane (30 mL) is added triethylamine (1.99 g, 19.55 mmol) and acetic anhydride (1.68 g, 16.29 mmol). After 45 min, the mixture is diluted with ethyl acetate and washed successively with 1M aqueous sodium bisulfate, saturated aqueous sodium bicarbonate, and brine. The organic phase is dried over magnesium sulfate, filtered, and concentrated to give acetic acid 7-methoxy-2,2-dimethyl-1,2,3,4-tetrahydro-naphthalen-1-yl ester, which is used in the next step without further purification.

To a solution of 7-methoxy-2,2-dimethyl-1,2,3,4-tetrahydro-naphthalen-1-yl ester (0.108 g, 0.426 mmol) in dichloromethane (2 mL) is added chromium (VI) oxide (0.022 g, 0.213 mmol) and water (0.5 mL) and the mixture is vigorously stirred until dissolution of the chromium (VI) oxide. TBHP (5-6M in decane, 0.45 mL, 2.25-2.7 mmol) is added and after 65 hours, another portion of TBHP (5-6M in decane, 0.45 mL, 2.25-2.7 mmol) is added. After another 7 hours, CrO$_3$ (0.022 g, 0.213 mmol) is added. After another 16 hours, water is added and the mixture is extracted twice with dichloromethane. The organic phases are dried over magnesium sulfate, filtered, and concentrated. The resulting residue is purified by silica gel flash chromatography (elution with hexanes-ethyl acetate, 9:1 to 4:1) to afford acetic acid 7-methoxy-2,2-dimethyl-4-oxo-1,2,3,4-tetrahydro-naphthalen-1-yl ester; $^1$H NMR (400 MHz, CDCl$_3$) δ ppm 1.02 (s, 3 H), 1.07 (s, 3 H), 2.13 (s, 3 H), 2.42 (d, J=16.9 Hz, 1 H), 2.79 (d, J=16.9 Hz, 1 H), 3.87 (s, 3 H), 5.86 (s, 1 H), 6.87 (d, J=2.5 Hz, 1 H), 6.93 (dd, J=8.6, 2.5 Hz, 1 H), 8.02 (d, J=8.6 Hz, 1 H).

c) 3-(7-Methoxy-2,2-dimethyl-4-oxo-1,2,3,4-tetrahydro-naphthalen-1-yl)-3H-imidazole-4-carboxylic acid isopropyl ester

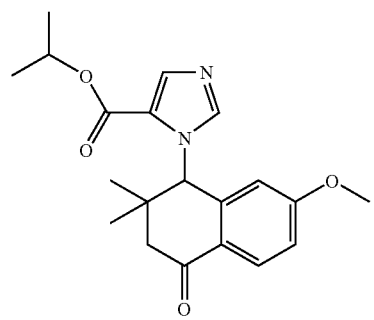 [SMILES: COc1ccc2c(c1)C(n1cncc1C(=O)OC(C)C)C(C)(C)CC2=O]

To a solution of acetic acid 7-methoxy-2,2-dimethyl-4-oxo-1,2,3,4-tetrahydro-naphthalen-1-yl ester (0.94 g, 3.44 mmol) in dichloromethane (2 mL) and methanol (10 mL) is added K$_2$CO$_3$ (0.48 g, 3.44 mmol) and the mixture is vigorously stirred for 8 hours. Ethyl acetate is added and the mixture is washed twice with water and brine. The aqueous phases are back-extracted once with dichloromethane and the combined organic phase is dried over magnesium sulfate, filtered, and concentrated to afford 6-methoxy-4-hydroxy-3,3-dimethyl-3,4-dihydro-2H-naphthalen-1-one, which is used in the next step without further purification.

To a solution of 6-methoxy-4-hydroxy-3,3-dimethyl-3,4-dihydro-2H-naphthalen-1-one (0.75 g, 3.28 mmol), isopropyl 4-imidazolecarboxylate (0.36 g, 2.30 mmol), which can be prepared as described in Example 1, in THF (20 mL) at 0° C. is added triphenylphosphine (0.87 g, 3.28 mmol), followed by dimethyl azodicarboxylate (40% in toluene, 1.2 mL, 3.28 mmol) and the cooling bath is removed. After 16 hours, the mixture is diluted with ethyl acetate and washed twice with half-saturated brine. The mixture is extracted five times with 1M aqueous HCl (20 mL portions). The acidic aqueous phases are then cooled to 0° C., the pH is adjusted to ca. 9 with 2M aqueous NaOH at 0° C. and the aqueous phase is extracted three times with dichloromethane. The combined organic phases are dried over MgSO$_4$, filtered, and concentrated. The resulting residue is purified by silica gel flash chromatography (dichloromethane-methanol, 99:1 to 49:1) to give 3-(7-methoxy-2,2-dimethyl-4-oxo-1,2,3,4-tetrahydro-naphthalen-1-yl)-3H-imidazole-4-carboxylic acid isopropyl ester; MS: (ESI) m/z 357.1 (M+H)$^+$ The HCl salt of the title compound can be prepared by dissolution in diethyl ether followed by treatment with an excess of 1N HCl in diethyl ether. The resulting heterogeneous solution is concentrated to furnish the HCl salt of 3-(7-methoxy-2,2-dimethyl-4-oxo-1,2,3,4-tetrahydro-naphthalen-1-yl)-3H-imidazole-4-carboxylic acid isopropyl ester $^1$H NMR (400 MHz, MeOD) δ ppm 1.00 (s, 3 H), 1.23 (s, 3 H), 1.48 (d, J=6.3 Hz, 3 H), 1.50 (d, J=6.3 Hz, 3 H), 2.61 (d, J=17.4 Hz, 1 H), 2.78 (d, J=17.4 Hz, 1 H), 3.89 (s, 3H), 5.34-5.47 (m, 1 H), 6.85 (d, J=2.3 Hz, 1 H), 6.95 (s, 1 H), 7.20 (dd, J=8.6, 2.3 Hz, 1 H), 8.16 (d, J=8.6 Hz, 1 H), 8.40 (s, 1 H), 8.94 (s, 1 H).

Examples for General Scheme 2

Example 15 a) (R)- and (S)-1-(2,2-Dimethyl-2,3-dihydro-benzofuran-3-yl)-1H-imidazole

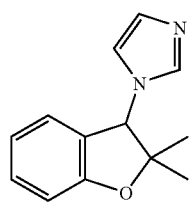 [SMILES: CC1(C)Oc2ccccc2C1n1ccnc1]

To a solution of 2,2-dimethyl-2,3-dihydro-benzofuran-3-ol, which can be prepared as described in Example 11, (260 mg, 1.58 mmol) in acetonitrile (5 mL) is added 1,1'-carbonyldiimidazole (310 mg, 1.90 mmol). The mixture is then heated at reflux overnight. The reaction is cooled to room temperature and concentrated. The resulting residue is dissolved in dichloromethane and washed with saturated aqueous NaHCO$_3$ and brine. The organic solution is dried with Na$_2$SO$_4$, filtered, and concentrated. The resulting residue is purified by silica gel flash chromatography (ethyl acetate-dichloromethane, 0:1 to 4:1) to furnish 1-(2,2-dimethyl-2,3-dihydro-benzofuran-3-yl)-1H-imidazole; HRMS: (ESI) m/z 215.1187 [(M+H)$^+$: Calcd for C$_{13}$H$_{14}$N$_2$O: 215.1184]. The HCl salt of the title compound can be prepared by dissolution in diethyl ether, followed by treatment with an excess of 1N HCl in diethyl ether. The resulting heterogeneous solution is concentrated to furnish the HCl salt of 1-(2,2-dimethyl-2,3-dihydro-benzofuran-3-yl)-1H-imidazole. $^1$H NMR (400 MHz, CD$_3$OD) δ ppm 1.17 (s, 3 H), 1.55 (s, 3 H), 5.90 (s, 1 H), 6.99 (d, J=8.08 Hz, 1 H), 7.06 (t, J=7.58 Hz, 1 H), 7.25 (s, 1 H), 7.40 (d, J=7.58 Hz, 1 H), 7.42-7.49 (m, 1 H), 7.59 (s, 1 H), 8.81 (s, 1 H).

Resolution of the enantiomers of the free base of this compound is achieved by chiral HPLC using a ChiralPak IA column with 9:1 heptane:ethanol to give LDA568 (t$_r$=13.0 min) and LDA569 (t$_r$=15.0 min)

The Following Compounds can be Prepared in a Similar Fashion as Example 15

(R)- and (S)-1-(2,2-Dimethyl-indan-1-yl)-1H-imidazole

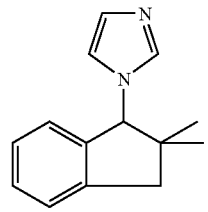 [SMILES: CC1(C)Cc2ccccc2C1n1ccnc1]

$^1$H NMR of the free base (400 MHz, CDCl$_3$) δ ppm 0.75 (s, 3 H), 1.28 (s, 3 H), 2.70-3.03 (m, 2 H), 5.19 (s, 1 H), 6.73 (s, 1 H), 7.07 (s, 1 H), 7.15-7.38 (m, 4 H), 7.46 (s, 1 H); MS: (ESI) m/z 213.2 (M+H)$^+$.

Resolution of the enantiomers of the free base of this compound is achieved by chiral HPLC using a ChiralPak IA column with 1:4 isopropanol-heptane to give (R)-1-(2,2-Dimethyl-indan-1-yl)-1H-imidazole (t$_r$=13.7 min) and (S)-1-(2,2-Dimethyl-indan-1-yl)-1H-imidazole (t$_r$=15.9 min)

Example 16 a) 1-Thiochroman-4-yl-1H-imidazole

A mixture of thiochroman-4-ol (CAS#40316-60-7, 320 mg, 2.0 mmol) and 1,1'-carbonyl diimidazole (320 mg, 2 mmol) in 15 mL of dry acetonitrile is heated to reflux for 4 hours. The reaction is concentrated and the resulting residue is purified by silica gel flash chromatography (methanol-dichloromethane, 1:9) to furnish 1-thiochroman-4-yl-1H-imidazole; MS: (ESI) m/z 217 (M+H)$^+$; $^1$H NMR (400 MHz, CDCl$_3$) δ ppm 2.38-2.63 (m, 2H), 2.87-3.04 (m, 2H), 5.41-5.44 (m, 1H), 6.86-7.54 (m, 7H)

Example 17 a) 2,2-Dimethyl-3-phenylsulfanyl-propionic acid

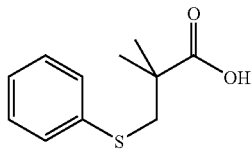

To a solution of thiophenol (5 g, 45 mmol) in DMF (100 mL) is added 3-bromo-2,2-dimethyl-propionic acid (CAS#2843-17-6, 3.98 g, 22 mmol), and potassium fluoride (1.56 g, 27 mmol). The reaction is heated at 120° C. overnight. The reaction is then cooled to room temperature and poured into ice water. A white precipitate is filtered and washed with ice water. The solid is then dissolved in 1M aqueous NaOH and is washed with dichloromethane. The aqueous solution is acidified with 1M HCl and the resulting precipitate is collected to provide 2,2-dimethyl-3-phenylsulfanyl-propionic acid; $^1$H NMR (400 MHz, CDCl$_3$) δ ppm 1.31 (s, 6 H), 2.72 (br. s., 1 H), 3.19 (s, 2 H), 7.09-7.21 (m, 1 H), 7.21-7.32 (m, 2 H), 7.40 (d, J=7.8 Hz, 2 H).

b) 3,3-Dimethyl-thiochroman-4-ol

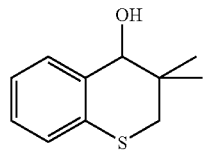

A mixture of 2,2-dimethyl-3-phenylsulfanyl-propionic acid (290 mg, 1.38 mmol) and Eaton's reagent (7 mL) is stirred for overnight at 65° C. The mixture is poured onto ice and basified by the addition of 1M aqueous NaOH. The mixture is extracted three times with dichloromethane. The combined extracts are dried with Na$_2$SO$_4$, filtered and concentrated. The resulting residue is then dissolved in ethanol (10 mL). The resulting solution is charged with NaBH$_4$ (82.6 mg, 2.18 mmol). The mixture is stirred for 48 hours, quenched with 10% aqueous HCl, and concentrated to dryness. The resulting residue is purified by silica gel flash chromatography (ethyl acetate-heptane, 1:4) to afford (3,3-dimethyl-thiochroman-4-ol); $^1$H NMR (400 MHz, CDCl$_3$) δ ppm 0.98 (s, 3 H), 1.21 (s, 3 H), 1.58 (d, J=5.1 Hz, 1 H), 2.50 (d, J=13.4 Hz, 1 H), 3.26 (d, J=12.4 Hz, 1 H), 4.17 (d, J=4.6 Hz, 1 H), 6.99-7.09 (m, 1 H) 7.11-7.20 (m, 2 H), 7.27 (m, 1 H).

c) 1-(3,3-Dimethyl-thiochroman-4-yl)-1H-imidazole

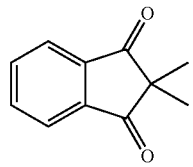

To a solution of 3,3-dimethyl-thiochroman-4-ol (675 mg, 3.5 mmol) in acetonitrile (15 mL) is added 1,1'-carbonyldiimidazole (845 mg, 5.2 mmol). The resulting solution is heated at reflux for 4 hours. The solvent is then concentrated and the resulting residue is dissolved in dichloromethane (20 mL) and washed with water, dried with Na$_2$SO$_4$, filtered and concentrated. The resulting residue is purified by silica gel flash chromatography (methanol-dichloromethane, 0:1 to 1:50) to furnish 1-(3,3-dimethyl-thiochroman-4-yl)-1H-imidazole; HRMS: (ESI) m/z 245.1107 [(M+H)$^+$ Calcd for C$_{14}$H$_{17}$N$_2$S 245.1112); $^1$H NMR (400 MHz, CDCl$_3$) δ ppm 1.04 (s, 3 H) 1.15 (s, 3 H) 2.61 (dd, J=13.1, 1.3 Hz, 1 H) 3.00 (d, J=13.1 Hz, 1 H) 4.78 (s, 1 H) 6.78-6.87 (m, 1 H) 6.98-7.02 (m, 2 H) 7.04 (s, 1 H) 7.17-7.23 (m, 2 H) 7.57 (s, 1 H).

d) (R)- and (S)-1-(3,3-Dimethyl-thiochroman-4-yl)-1H-imidazole

Resolution of the enantiomers is achieved by chiral HPLC using the ChiralPak OD-H column with 1:9 ethanol-heptane as mobile phase to give (R)- and (S)-1-(3,3-Dimethyl-thiochroman-4-yl)-1H-imidazole with t$_r$=12.7 min and (R)- and (S)-1-(3,3-Dimethyl-thiochroman-4-yl)-1H-imidazole t$_r$=14.9 min.

Examples for General Scheme 3

Example 18 a) 2,2-Dimethyl-indan-1,3-dione

Potassium fluoride on Celite® [loading wt: 50% purchased from Sigma-Aldrich Co.] (5.8 g, ~50 mmol) is heated at 135° C. for 2 hours under vacuum (<20 torr). The solid is then permitted to cool to room temperature and placed under a nitrogen atmosphere at which time a solution of indan-1,3-dione (CAS#606-23-5, 1.46 g, 10.0 mmol) in acetonitrile (15 mL) is added followed by iodomethane (1.8 mL, 30 mmol). The reaction is heated in a sealed vessel at 70° C. overnight. The reaction mixture is cooled to room temperature and filtered through a pad of Celite®. The eluent is concentrated and the resulting residue is purified by silica gel flash chromatography (ethyl acetate-heptane, 0:1 to 1:9) to furnish 2,2-dimethyl-indan-1,3-dione $^1$H NMR (400 MHz, CDCl$_3$) δ ppm 1.30 (s, 6 H), 7.84-7.89 (m, 2 H), 7.96-8.02 (m, 2 H).

b) 3,3-Difluoro-2,2-dimethyl-indan-1-one

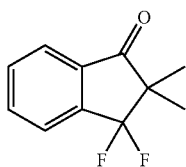

To a solution of 2,2-dimethyl-indan-1,3-dione (770 mg, 4.42 mmol) in chlorobenzene (3 mL) is added (diethylamino)sulfur trifluoride (2.9 mL, 22.1 mmol) followed by ethanol (52 µL, 0.9 mmol). The reaction is heated to reflux for 3 hours, at which time the mixture is cooled to room temperature and diluted with water and saturated aqueous NaHCO$_3$. The solution is extracted two times with ethyl acetate and the organic extracts are combined, dried with Na$_2$SO$_4$, filtered, and concentrated. The resulting residue is purified by silica gel flash chromatography (ethyl acetate-heptane, 0:1 to 1:10) to furnish 3,3-difluoro-2,2-dimethyl-indan-1-one; $^1$H NMR (400 MHz, CDCl$_3$) δ ppm 1.31 (t, J=1.9 Hz, 6 H), 7.69 (t, J=7.3 Hz, 1 H), 7.78-7.89 (m, 3 H).

c) 3,3-Difluoro-2,2-dimethyl-indan-1-ol

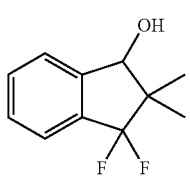

To a solution of 3,3-difluoro-2,2-dimethyl-indan-1-one (520 mg, 2.65 mmol) in ethanol (15 mL) is added NaBH$_4$ (100 mg, 2.65 mmol). After 15 minutes the reaction is quenched with saturated aqueous NH$_4$Cl and concentrated to near dryness. The resulting residue is diluted with ethyl acetate and washed with brine, dried with Na$_2$SO$_4$, filtered, and concentrated. The resulting residue is purified by silica gel flash chromatography (ethyl acetate-heptane, 0:1 to 1:6) to provide 3,3-difluoro-2,2-dimethyl-indan-1-ol; $^1$H NMR (400 MHz, CDCl$_3$) δ ppm 1.07 (d, J=2.3 Hz, 2 H), 1.27 (d, J=2.3 Hz, 2 H), 4.79-4.83 (m, 1 H), 7.41-7.46 (m, 1 H), 7.48-7.60 (m, 3 H).

d) 3-(3,3-Difluoro-2,2-dimethyl-indan-1-yl)-3H-imidazole-4-carboxylic acid methyl ester

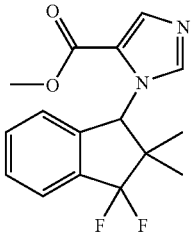 [SMILES: COC(=O)c1cncn1C1c2ccccc2C(F)(F)C1(C)C]

To a solution of 3,3-difluoro-2,2-dimethyl-indan-1-ol (388 mg, 1.96 mmol) in THF (16 mL) is added methyl 4-imidazolecarboxylate (CAS#17325-26-7, 370 mg, 2.94 mmol), and triphenylphosphine (770 mg, 2.94 mmol). The reaction is cooled to 0° C. and di-t-butyl azodicarboxylate (670 mg, 2.94 mmol) is added. The reaction is placed at room temperature and permitted to stir for six hours and then is heated to 40° C. overnight. The next day the reaction mixture is cooled to 0° C. and quenched with 4 N HCl in dioxane (5 mL, 20 mmol) and stirred for 30 minutes. The reaction is concentrated to near dryness and diluted with ethyl acetate. The organic layer is extracted three times with 1 N aqueous HCl. The aqueous extracts are combined, neutralized with Na$_2$CO$_3$, and extracted three times with ethyl acetate. The combined organic layers are dried with Na$_2$SO$_4$ filtered, and concentrated. The resulting residue is purified by silica gel flash chromatography (ethyl acetate-dichloromethane, 0:1 to 1:5) to furnish 3-(3,3-difluoro-2,2-dimethyl-indan-1-yl)-3H-imidazole-4-carboxylic acid methyl ester. MS: (ESI) m/z 307.0 (M+H)$^+$; $^1$H NMR (400 MHz, CDCl$_3$) δ ppm 0.87 (d, J=2.5 Hz, 3 H), 1.33 (d, J=3.0 Hz, 3 H), 3.96 (s, 3 H), 6.43 (d, J=2.8 Hz, 1 H), 7.17 (s, 1 H), 7.30-7.37 (m, 1 H), 7.56-7.64 (m, 2 H), 7.69-7.76 (m, 1 H), 7.85 (s, 1 H)

Examples for General Scheme 4

Example 19 a) 2,2-Dimethyl-1,1-dioxo-1,2-dihydro-1lambda*6*-benzo[b]thiophen-3-one

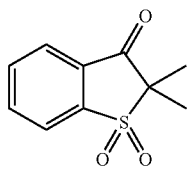

To a solution of (propane-2-sulfonyl)-benzene (CAS#4238-09-9), which can be prepared as described in Cram, D. J. et al. *Journal of the American Chemical Society*, 1967, 89, 2072-2077, (1.18 g, 6.4 mmol) in THF (60 mL) at 0° C. is added a 2.5 M solution of n-butyl lithium in hexanes (5.8 mL, 14.7 mmol). The solution is slowly warmed to room temperature over an hour, at which time it is re-cooled to −78° C. and methylchloroformate (0.74 mL, 9.6 mmol) is added.

The reaction is brought to room temperature and permitted to stir for 16 hours. The reaction is then quenched with saturated aqueous NH₄Cl and diluted with ethyl acetate. The layers are separated and the aqueous layer is extracted twice with ethyl acetate. The organic layers are combined, dried with Na₂SO₄, filtered, and concentrated. The resulting residue is purified by silica gel flash chromatography (ethyl acetate-heptane, 0:1 to 1:4) to provide 2,2-dimethyl-1,1-dioxo-1,2-dihydro-1lambda*6*-benzo[b]thiophen-3-one. ¹H NMR (400 MHz, CDCl₃) δ ppm 1.63 (s, 6 H), 7.79-7.86 (m, 1 H), 7.92-7.99 (m, 1 H), 8.03 (d, J=8.1 Hz, 2 H).

b) 2,2-Dimethyl-1,1-dioxo-2,3-dihydro-1H-1lambda*6*-benzo[b]thiophen-3-ol

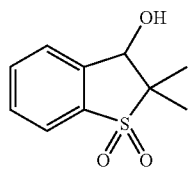

To a solution of 2,2-dimethyl-1,1-dioxo-1,2-dihydro-1lambda*6*-benzo[b]thiophen-3-one (240 mg, 1.14 mmol) in ethanol (30 mL) at 0° C. is added NaBH₄ (43 mg, 1.14 mmol). The reaction is placed at room temperature and permitted to stir for one hour. The reaction is quenched with saturated aqueous NH₄Cl, and concentrated to near dryness. The resulting residue is diluted with ethyl acetate and washed with brine, dried with Na₂SO₄, filtered, and concentrated. The resulting residue is purified by silica gel flash chromatography (ethyl acetate-heptane, 0:1 to 1:0) to provide 2,2-dimethyl-1,1-dioxo-2,3-dihydro-1H-1lambda*6*-benzo[b]thiophen-3-ol; MS: (ESI) m/z 213 (M+H)⁺.

c) 3-(2,2-Dimethyl-1,1-dioxo-2,3-dihydro-1H-1lambda*6*-benzo[b]thiophen-3-yl)-3H-imidazole-4-carboxylic acid methyl ester

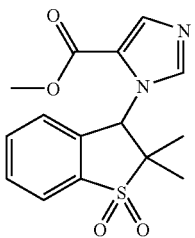 [SMILES: COC(=O)c1cncn1C1c2ccccc2S(=O)(=O)C1(C)C]

To a solution of 3,2-dimethyl-1,1-dioxo-2,3-dihydro-1H-1lambda*6*-benzo[b]thiophen-3-ol (3.1 g, 14.6 mmol) in THF (100 mL) is added methyl 4-imidazolecarboxylate (CAS#17325-26-7, 2.76 g, 2.1.9 mmol), and triphenylphosphine (5.73 g, 21.9 mmol). The reaction is cooled to 0° C. and di-t-butyl azodicarboxylate (5.04 g, 21.9 mmol) is added. The reaction is placed at room temperature and permitted to stir for three hours. The reaction mixture is cooled to 0° C. and quenched with 4 N HCl in dioxane (5 mL, 20 mmol) and stirred for 30 minutes. The reaction is concentrated to near dryness and diluted with ethyl acetate. The organic layer is extracted three times with 1 N aqueous HCl. The aqueous extracts are combined, neutralized with Na₂CO₃, and extracted three times with ethyl acetate. The combined organic layers are dried with Na₂SO₄, filtered, and concentrated. The resulting residue is purified by silica gel flash chromatography (ethyl acetate-dichloromethane, 0:1 to 3:7) to furnish 3-(2,2-dimethyl-1,1-dioxo-2,3-dihydro-1H-1lambda*6*-benzo[b]thiophen-3-yl)-3H-imidazole-4-carboxylic acid methyl ester; MS: (ESI) m/z 321 (M+H)⁺; ¹H NMR: (400 MHz, CDCl₃) δ ppm 1.18 (s, 3 H), 1.62 (s, 3 H), 3.96 (s, 3 H), 6.69 (s, 1 H), 7.29 (s, 1 H), 7.38-7.46 (m, 1 H), 7.68-7.76 (m, 2 H), 7.84 (s, 1 H), 7.91-7.97 (m, 1 H).

The Following Compounds can be Prepared in a Similar Fashion as Example 19

3-(2,2-Dimethyl-1,1-dioxo-2,3-dihydro-1H-1lambda*6*-benzo[b]thiophen-3-yl)-3H-imidazole-4-carboxylic acid isopropyl ester

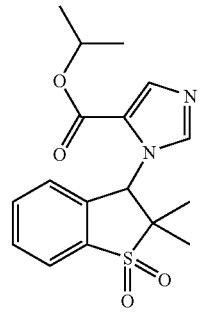 [SMILES: CC(C)OC(=O)c1cncn1C1c2ccccc2S(=O)(=O)C1(C)C]

¹H NMR (400 MHz, CDCl₃) of the free base δ ppm 1.19 (s, 3 H), 1.42 (s, 3 H), 1.44 (s, 3 H), 1.62 (s, 3 H), 5.15-5.40 (m, 1 H), 6.74 (s, 1 H), 7.38 (s, 1 H), 7.41-7.48 (m, 1 H), 7.70-7.80 (m, 2 H), 7.85 (s, 1 H), 7.92-7.98 (m, 1 H); HRMS: (ESI) m/z 349.1221 [(M+H)⁺: Calcd for C₁₇H₂₁N₂O₄S: 349.1222]

Resolution of the enantiomers is achieved by chiral HPLC using the ChiralPak AS-H column with 1:9 ethanol-heptane as mobile phase to give two enantiomers with t$_r$=15.2 min and t$_r$=18.8 min.

Examples for General Scheme 5

Example 20 a) 3-Hydroxy-2,2-dimethyl-indan-1-one

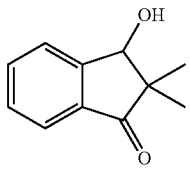

To a solution of 2,2-dimethyl-indan-1,3-dione (430 mg, 2.47 mmol), which can be prepared as described in Example 18, in ethanol (80 mL) at −30° C. is added a solution of NaBH₄ (29 mg, 0.74 mmol) in ethanol (3 mL). After one hour the reaction is quenched with saturated aqueous NH₄Cl and the mixture is brought to room temperature. The reaction mixture is concentrated to approximately half of its original volume and then diluted with ethyl acetate and washed with water. The aqueous layer is then back-extracted two times with ethyl acetate. The organic layers are combined, dried with Na$_2$SO$_4$, filtered, and concentrated. The resulting residue is purified by silica gel flash chromatography (ethyl acetate-heptane, 0:1 to 1:6) to afford 3-hydroxy-2,2-dimethyl-indan-1-one; MS: (ESI) m/z 177.0 (M+H)$^+$.

b) 3-(2,2-Dimethyl-3-oxo-indan-1-yl)-3H-imidazole-4-carboxylic acid methyl ester

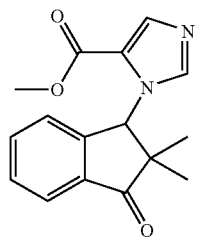 [SMILES: COC(=O)c1cncn1C1c2ccccc2C(=O)C1(C)C]

To a solution of 3-hydroxy-2,2-dimethyl-indan-1-one (2.0 g, 11.3 mmol) in THF (50 mL) is added methyl 4-imidazole-carboxylate (CAS#17325-26-7, 1.72 g, 13.6 mmol), and triphenylphosphine (3.56 g, 13.6 mmol). The reaction is cooled to 0° C. and di-t-butyl azodicarboxylate (3.13 g, 13.6 mmol) is added. The reaction is placed at room temperature and permitted to stir for three hours. The reaction mixture is cooled to 0° C. and quenched with 4 N HCl in dioxane (5 mL, 20 mmol) and stirred for 30 minutes. The reaction is concentrated to near dryness and diluted with ethyl acetate. The organic layer is extracted three times with 1 N aqueous HCl. The aqueous extracts are combined, neutralized with Na$_2$CO$_3$, and extracted three times with ethyl acetate. The combined organic layers are dried with Na$_2$SO$_4$ filtered, and concentrated. The resulting residue is purified by silica gel flash chromatography (ethyl acetate-dichloromethane, 0:1 to 3:7) to furnish 3-(2,2-dimethyl-3-oxo-indan-1-yl)-3H-imidazole-4-carboxylic acid methyl ester; HRMS: (ESI) m/z 285.1246 [(M+H)$^+$: Calcd for C$_{16}$H$_{16}$N$_2$O$_3$: 285.1239]; $^1$H NMR (400 MHz, CDCl$_3$) δ ppm 0.82 (s, 3 H), 1.46 (s, 3 H), 4.02 (s, 3 H), 6.70 (s, 1 H), 7.39 (s, 1 H), 7.47-7.52 (m, 1 H), 7.72 (t, J=7.45 Hz, 1 H), 7.79-7.86 (m, 1 H), 7.93-7.99 (m, 2 H).

Example 21 a) cis- and trans-3-(5-Hydroxymethyl-imidazol-1-yl)-2,2-dimethyl-indan-1-ol

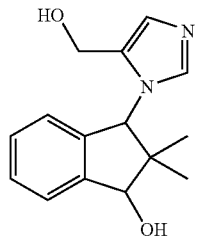 [SMILES: CC1(C)C(O)c2ccccc2C1n1cncc1CO]

To a solution of 3-(2,2-dimethyl-3-oxo-indan-1-yl)-3H-imidazole-4-carboxylic acid methyl ester (1.5 g, 5.3 mmol), which can be prepared as described in Example 20, in THF (35 mL) at 0° C. is added LiAlH$_4$ (300 mg, 7.9 mmol). The reaction is permitted to stir for 30 minutes, at which time it is quenched at 0° C. by the consecutive addition of 9:1 THF/H$_2$O (4.0 mL), 2M aqueous NaOH (4.5 mL), and H$_2$O (2.9 mL). The reaction is warmed to room temperature and diluted with THF (30 mL). After addition of MgSO$_4$ (4.2 g), the heterogeneous mixture is stirred for 15 min and then filtered through a pad of Celite®. The pad of Celite® is washed with ethyl acetate and the combined filtrate is concentrated. The resulting residue is purified by silica gel flash chromatography (methanol-dichloromethane, 0:1 to 1:9) to afford a ca. 5.5:1 diastereomeric mixture of 3-(5-hydroxymethyl-imidazol-1-yl)-2,2-dimethyl-indan-1-ol; MS: (ESI) m/z 259.0 (M+H)$^+$; $^1$H NMR (400 MHz, MeOD) Major Diastereomer: δ ppm 0.77 (s, 3 H), 1.25 (s, 3 H), 4.69 (s, 1 H), 4.73 (s, 2 H), 5.43 (s, 1 H), 6.96 (br. s., 1 H), 7.18 (d, J=7.6 Hz, 1 H), 7.30-7.57 (m, 4 H); Minor Diastereomer: δ ppm 0.82 (s, 3 H), 1.14 (s, 3 H), 4.73 (s, 2 H), 4.97 (s, 1 H), 5.59 (s, 1 H), 6.96 (br. s., 1 H), 7.23 (d, J=7.3 Hz, 1 H), 7.31-7.57 (m, 4 H).

b) 3-[5-(tert-Butyl-dimethyl-silanyloxymethyl)-imidazol-1-yl]-2,2-dimethyl-indan-1-ol

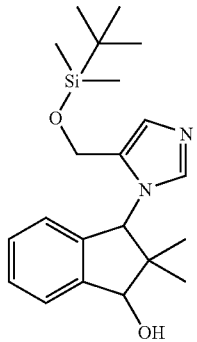 [SMILES: CC1(C)C(O)c2ccccc2C1n1cncc1CO[Si](C)(C)C(C)(C)C]

To a solution of 3-(5-hydroxymethyl-imidazol-1-yl)-2,2-dimethyl-indan-1-ol (348 mg, 1.34 mmol) in DMF (8 mL) is added imidazole (96 mg, 1.41 mmol) and the reaction is cooled to −20° C. Then a solution of t-butyldimethylsilyl chloride (193 mg, 1.28 mmol) in DMF (3 mL) is added. The reaction is allowed to warm to room temperature overnight. The next morning the reaction is concentrated to near dryness and diluted with water and ethyl acetate. The layers are separated and the aqueous layer is extracted with ethyl acetate. The organic layers are combined, dried with Na$_2$SO$_4$, filtered, and concentrated. The resulting residue is purified by silica gel flash chromatography (methanol-dichloromethane, 0:1 to 1:20) to furnish 3-[5-(tert-Butyl-dimethyl-silanyloxymethyl)-imidazol-1-yl]-2,2-dimethyl-indan-1-ol; MS: (ESI) m/z 373.1 (M+H)+.

c) 3-[5-(tert-Butyl-dimethyl-silanyloxymethyl)-imidazol-1-yl]-2,2-dimethyl-indan-1-one

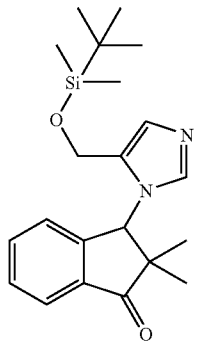 [SMILES: CC1(C)C(=O)c2ccccc2C1n1cncc1CO[Si](C)(C)C(C)(C)C]

To a solution of 3-[5-(tert-butyl-dimethyl-silanyloxymethyl)-imidazol-1-yl]-2,2-dimethyl-indan-1-ol (372 mg, 1.0 mmol) in 1,4-dioxane is added manganese(IV) oxide (1.74 g, 20 mmol). The reaction is then heated at 100° C. for one hour, cooled to room temperature, filtered, and concentrated to afford 3-[5-(tert-butyl-dimethyl-silanyloxymethyl)-imidazol-1-yl]-2,2-dimethyl-indan-1-one without the need for further purification; MS: (ESI) m/z 371.1 (M+H)+.

d) (R)- and (S)-3-(5-Hydroxymethyl-imidazol-1-yl)-2,2-dimethyl-indan-1-one

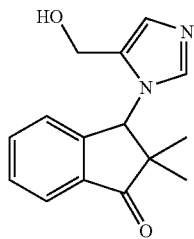 [SMILES: CC1(C)C(=O)c2ccccc2C1n1cncc1CO]

To 3-[5-(tert-butyl-dimethyl-silanyloxymethyl)-imidazol-1-yl]-2,2-dimethyl-indan-1-one (370 mg, 1 mmol) is added 4N HCl in 1,4-dioxane (20 mL, 0.80 mmol). The reaction is permitted to stir for 2 hours, at which time it is quenched with saturated aqueous NaHCO₃ and diluted with ethyl acetate. The layers are separated and the aqueous layer is extracted twice with ethyl acetate. The combined organic layers are dried with Na₂SO₄, filtered, and concentrated. The resulting residue is purified by silica gel flash chromatography (methanol-dichloromethane, 0:1 to 1:20) to furnish 3-(5-Hydroxymethyl-imidazol-1-yl)-2,2-dimethyl-indan-1-one; HRMS: (ESI) m/z 257.1295 [(M+H)+: Calcd for $C_{15}H_{17}N_2O_2$: 257.1290]; ¹H NMR (400 MHz, CDCl₃) δ ppm 0.87 (s, 3 H), 1.46 (s, 3 H), 4.69-4.97 (m, 2 H), 5.93 (s, 1 H), 7.16 (s, 1 H), 7.19 (s, 1 H), 7.54 (d, J=7.6 Hz, 1 H), 7.65 (t, J=7.5 Hz, 1 H), 7.72-7.82 (m, 1 H), 7.93 (d, J=7.6 Hz, 1 H).

The resolution of the enantiomers of the this compound is achieved by chiral HPLC using a ChiralPak IA column with 85:15 heptane:ethanol to give (R)-3-(5-Hydroxymethyl-imidazol-1-yl)-2,2-dimethyl-indan-1-one ($t_r$=13.6 min) and (S)-3-(5-Hydroxymethyl-imidazol-1-yl)-2,2-dimethyl-indan-1-one ($t_r$=15.7 min).

Examples for General Scheme 6

Example 22 a) (R)- and (S)-2-[3-(3,3-Difluoro-2,2-dimethyl-indan-1-yl)-3H-imidazol-4-yl]-propan-2-ol

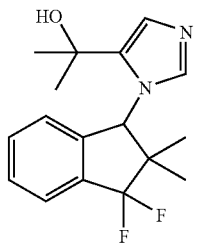 [SMILES: CC(C)(O)c1cncn1C1c2ccccc2C(F)(F)C1(C)C]

To a solution of 3-(3,3-difluoro-2,2-dimethyl-indan-1-yl)-3H-imidazole-4-carboxylic acid methyl ester (300 mg, 0.98 mmol), which can be prepared as described in Example 18, in THF (10 mL) at 0° C. is added a 3.0 M solution of methylmagnesium bromide in diethyl ether (1.63 mL, 4.9 mmol). After one hour of stirring the reaction is quenched with saturated aqueous NH₄Cl. The reaction is extracted three times with ethyl acetate and the organic extracts are combined, washed with brine, dried with Na₂SO₄, filtered, and concentrated. The resulting residue is purified by silica gel flash chromatography (ethyl acetate-dichloromethane, 0:1 to 1:5) to afford 2-[3-(3,3-difluoro-2,2-dimethyl-indan-1-yl)-3H-imidazol-4-yl]-propan-2-ol; HRMS: (ESI) m/z 307.1628 [(M+H)+: Calcd for $C_{17}H_{21}N_2OF_2$: 307.1622]; ¹H NMR (400 MHz, CDCl₃) δ ppm 0.97 (d, J=2.53 Hz, 3 H), 1.29 (d, J=3.28 Hz, 3 H), 1.79 (s, 6 H), 6.16 (d, J=3.79 Hz, 1 H), 6.89 (s, 1 H), 7.03 (s, 1 H), 7.33-7.41 (m, 1 H), 7.47-7.59 (m, 2 H), 7.62-7.72 (m, 1 H).

Resolution of the enantiomers of this compound is achieved by chiral HPLC using a ChiralPak AS-H column with 4:1 heptane:ethanol to give (R)-2-[3-(3,3-Difluoro-2,2-dimethyl-indan-1-yl)-3H-imidazol-4-yl]-propan-2-ol ($t_r$=8.5 min) and (S)-2-[3-(3,3-Difluoro-2,2-dimethyl-indan-1-yl)-3H-imidazol-4-yl]-propan-2-ol ($t_r$=11.0 min).

The Following Compounds can be Prepared in a Similar Fashion as Example 22

2-[3-(2,2-Dimethyl-indan-1-yl)-3H-imidazol-4-yl]-propan-2-ol

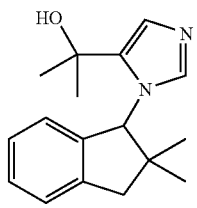 [SMILES: CC(C)(O)c1cncn1C1c2ccccc2CC1(C)C]

¹H NMR (400 MHz, CDCl₃) of the free base δ ppm 0.89 (s, 3 H), 1.24 (s, 3 H), 1.76 (s, 3 H), 1.78 (s, 3 H), 2.13 (br. s., 1 H), 2.75-3.11 (m, 2 H), 5.92 (s, 1 H), 6.88 (s, 1 H), 6.97 (br. s., 1 H), 7.18-7.24 (m, 2 H), 7.28-7.36 (m, 2 H); HRMS: (ESI) m/z 271.1809 [(M+H)⁺: Calcd for $C_{17}H_{23}N_2O$: 271.1810].

(R)- and (S)-2-[3-(2,2-Dimethyl-2,3-dihydro-benzofuran-3-yl)-3H-imidazol-4-yl]-propan-2-ol

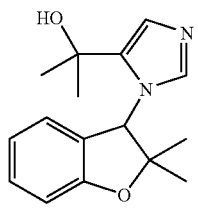 [SMILES: CC(C)(O)c1cncn1C1c2ccccc2OC1(C)C]

¹H NMR (400 MHz, CDCl₃) of the free base δ ppm 1.14 (s, 3 H), 1.48 (s, 3 H), 1.74 (s, 6 H), 6.05 (s, 1 H), 6.81 (s, 1 H), 6.87-6.95 (m, 3 H), 7.21 (d, J=7.6 Hz, 1 H), 7.28-7.34 (m, 1 H); HRMS: (ESI) m/z 273.1613 [(M+H)⁺: Calcd for $C_{16}H_{21}N_2O_2$: 273.1603]

Resolution of the enantiomers of this compound is achieved by chiral HPLC using a ChiralPak IA column with 9:1 heptane:ethanol to give (R)-2-[3-(2,2-Dimethyl-2,3-dihydro-benzofuran-3-yl)-3H-imidazol-4-yl]-propan-2-ol (t_r=6.5 min) and (S)-2-[3-(2,2-Dimethyl-2,3-dihydro-benzofuran-3-yl)-3H-imidazol-4-yl]-propan-2-ol (t_r=8.8 min).

3-[3-(2,2-Dimethyl-indan-1-yl)-3H-imidazol-4-yl]-pentan-3-ol

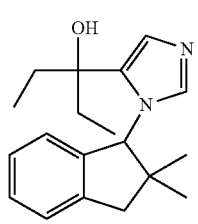 [SMILES: CCC(O)(CC)c1cncn1C1c2ccccc2CC1(C)C]

¹H NMR (400 MHz, CDCl₃) of the free base δ ppm 0.81-0.92 (m, 6 H), 1.01 (t, J=7.5 Hz, 3 H), 1.22 (s, 3 H), 1.85-2.14 (m, 4 H), 2.71-3.13 (m, 2 H), 5.95 (s, 1 H), 6.82 (s, 1 H), 6.92 (s, 1 H), 7.11-7.17 (m, 1 H), 7.18-7.25 (m, 1 H), 7.26-7.34 (m, 2 H); MS: (ESI) m/z 299.3 (M+H)⁺.

Examples for General Scheme 7

Example 23 a) [3-(2,2-Dimethyl-2,3-dihydro-benzofuran-3-yl)-3H-imidazol-4-yl]-methanol

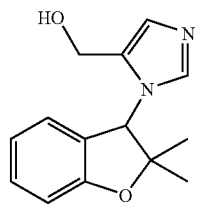 [SMILES: CC1(C)Oc2ccccc2C1n1cncc1CO]

To a solution of 3-(2,2-dimethyl-2,3-dihydro-benzofuran-3-yl)-3H-imidazole-4-carboxylic acid methyl ester (2.2 g, 8.1 mmol), which can be prepared as described in Example 11, in THF (80 mL) at 0° C. is added LiAlH₄ (310 mg, 8.1 mmol). After 30 minutes the reaction is quenched at 0° C. by the consecutive addition of 9:1 THF/H₂O (3.5 mL), 2M aqueous NaOH (1.4 mL), and H₂O (2.6 mL). The reaction is warmed to room temperature and diluted with THF (30 mL). After the addition of MgSO₄ (3.75 g), the heterogeneous mixture is stirred for 15 min and then filtered through a pad of Celite®. The pad of Celite® is washed with ethyl acetate and the combined filtrate is concentrated. The resulting residue is purified by silica gel flash chromatography (methanol-dichloromethane, 0:1 to 1:20) to afford 3-(2,2-dimethyl-2,3-dihydro-benzofuran-3-yl)-3H-imidazol-4-yl]-methanol; HRMS: (ESI) m/z 245.1296 [(M+H)+: Calcd for $C_{14}H_{17}N_2O_2$: 245.1290]; ¹H NMR (400 MHz, CDCl₃) δ ppm 1.10 (s, 3 H), 1.54 (s, 3 H), 4.57-4.87 (m, 2 H), 5.60 (s, 1 H), 6.81-7.06 (m, 4 H), 7.22 (d, J=7.45 Hz, 1 H), 7.34 (t, J=7.45 Hz, 1 H).

b) (R)- and (S)-[3-(2,2-Dimethyl-2,3-dihydro-benzofuran-3-yl)-3H-imidazol-4-yl]-methanol Resolution of the enantiomers of this compound is achieved by chiral HPLC using a ChiralPak AD-H column with 9:1 heptane:ethanol to give (R)- and (S)-[3-(2,2-Dimethyl-2,3-dihydro-benzofuran-3-yl)-3H-imidazol-4-yl]- methanol ($t_r$=3.2 min) and (R)- and (S)-[3-(2,2-Dimethyl-2, 3-dihydro-benzofuran-3-yl)-3H-imidazol-4-yl]-methanol ($t_r$=3.7 min).

The Following Compounds can be Prepared in a Similar Fashion as Example 23

[3-(2,2-Dimethyl-indan-1-yl)-3H-imidazol-4-yl]-methanol

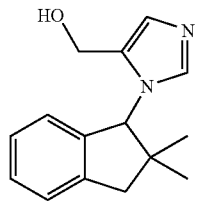 [SMILES: CC1(C)Cc2ccccc2C1n1cncc1CO]

$^1$H NMR (400 MHz, CDCl$_3$) of the free base δ ppm 0.83 (s, 3 H), 1.29 (s, 3 H), 2.76-3.07 (m, 2 H), 4.61-4.93 (m, 2 H), 5.44 (s, 1 H), 6.95-7.42 (m, 6 H); HRMS: (ESI) m/z 243.1496 [(M+H)$^+$: Calcd for C$_{15}$H$_{19}$N$_2$O: 243.1497].

Resolution of the enantiomers of this compound is achieved by chiral HPLC using a ChiralPak AS-H column with 9:1 hexanes:ethanol to give the two enantiomers with $t_r$=6.2 min and $t_r$=11.0 min.

[3-(2,2-Dimethyl-1,1-dioxo-2,3-dihydro-1H-1lambda*6*-benzo[b]thiophen-3-yl)-3H-imidazol-4-yl]-methanol

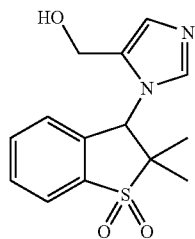 [SMILES: CC1(C)C(n2cncc2CO)c2ccccc2S1(=O)=O]

$^1$H NMR (400 MHz, CD$_3$OD) of the HCl salt: δ ppm 1.20 (s, 3 H), 1.57 (s, 3 H), 4.72-4.84 (m, 2 H), 5.95 (s, 1 H), 6.97 (s, 1 H), 7.21 (s, 1 H), 7.47-7.58 (m, 1 H), 7.72-7.82 (m, 2 H), 7.87-7.96 (m, 1 H); HRMS: (ESI) m/z 293.0961 [(M+H)$^+$: Calcd for C$_{14}$H$_{17}$N$_2$O$_3$S 293.0960].

The resolution of the enantiomers of the titled compound is achieved by chiral HPLC using a ChiralPak AS-H column with 65:35 heptane:ethanol to give LDF013 ($t_r$=9.9 min) and LDF014 ($t_r$=12.4 min)

[3-(4,4-Dimethyl-1,2,3,4-tetrahydro-naphthalen-1-yl)-3H-imidazol-4-yl]-methanol

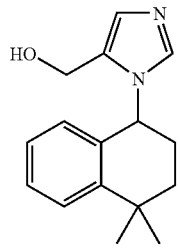

$^1$H NMR (400 MHz, CDCl$_3$) of the free base δ ppm 1.33 (s, 3 H), 1.40 (s, 3 H), 1.67-1.82 (m, 2 H), 2.12-2.31 (m, 2 H), 4.55-4.71 (m, 2 H), 5.53 (t, J=6.4 Hz, 1 H), 6.78 (d, J=7.8 Hz, 1 H), 6.89 (s, 1 H), 7.06 (t, J=7.45 Hz, 1 H), 7.11 (s, 1 H), 7.23-7.31 (m, 1 H), 7.41 (d, J=7.8 Hz, 1 H); MS: (ESI) m/z 257 (M+H)$^+$.

Example 24 a) (R)- and (S)-[3-(3,3-Difluoro-2,2-dimethyl-indan-1-yl)-3H-imidazol-4-yl]-methanol

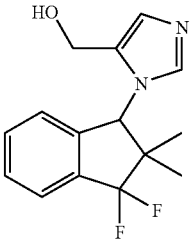 [SMILES: CC1(C)C(n2cncc2CO)c2ccccc2C1(F)F]

To a solution of 3-(3,3-difluoro-2,2-dimethyl-indan-1-yl) #H-imidazole-4-carboxylic acid methyl ester, which can be prepared as described in Example 18, (218 mg, 0.71 mmol) in THF (6 mL) at 0° C. is added LiAlH$_4$ (27 mg, 0.71 mmol). The reaction is placed at room temperature and after 15 minutes is quenched at 0° C. by the consecutive addition of 9:1 THF/H$_2$O (0.35 mL), 2M aqueous NaOH (0.14 mL), and H$_2$O (0.26 mL). The reaction is warmed to room temperature and diluted with THF (3.00 mL). After addition of MgSO$_4$ (375 mg), the heterogeneous mixture is stirred for 15 min and then filtered through a pad of Celite®. The pad of Celite® is washed with ethyl acetate and the combined filtrate is concentrated. The resulting residue is purified by silica gel flash chromatography (methanol-dichloromethane, 0:1 to 1:15) to afford [3-(3,3-Difluoro-2,2-dimethyl-indan-1-yl)-3H-imidazol-4-yl]-methanol; HRMS: (ESI) m/z 279.1312 [(M+H)$^+$: Calcd for C$_{15}$H$_{17}$F$_2$N$_2$O: 271.1309] The HCl salt of the title compound can be prepared by dissolution in diethyl ether, followed by treatment with an excess of 1N HCl in diethyl ether. The resulting heterogeneous solution is concentrated to furnish the HCl salt of [3-(3,3-Difluoro-2,2-dimethyl-indan-1-yl)-3H-imidazol-4-yl]-methanol; $^1$H NMR: (400 MHz, CD$_3$OD) δ ppm 0.99 (d, J=2.8 Hz, 3 H), 1.37 (d, J=3.0 Hz, 3 H), 4.85-4.96 (m, 2 H), 5.98 (d, J=2.5 Hz, 1 H), 7.46-7.55 (m, 1 H), 7.63 (s, 1 H), 7.68-7.74 (m, 2 H), 7.74-7.82 (m, 1 H), 8.32 (s, 1 H)

Resolution of the enantiomers of the free base of this compound is achieved by chiral HPLC using a ChiralPak AS-H column with 85:15 heptane:ethanol to give (R)-[3-(3,3-Difluoro-2,2-dimethyl-indan-1-yl)-3H-imidazol-4-yl]-methanol (t$_r$=13.5 min) and (S)-[3-(3,3-Difluoro-2,2-dimethyl-indan-1-yl)-3H-imidazol-4-yl]-methanol (t$_r$=20.9 min).

b) (R) and (S)-1-(3,3-Difluoro-2,2-dimethyl-indan-1-yl)-5-ethoxymethyl-1H-imidazole

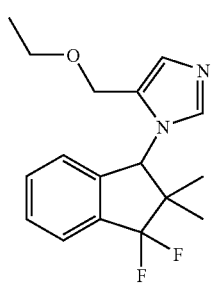 [SMILES: CCOCc1cncn1C1c2ccccc2C(F)(F)C1(C)C]

To a solution of [3-(3,3-difluoro-2,2-dimethyl-indan-1-yl)-3H-imidazol-4-yl]-methanol, (160 mg, 0.575 mmol) in DMF (5 mL) is added a 60% dispersion of NaH in oil (46 mg, 1.15 mmol). The reaction is permitted to stir for 30 minutes at room temperature, at which time iodoethane (0.05 mL, 0.63 mmol) is added. The reaction is permitted to stir for 2 hours at which time it is diluted with saturated aqueous NaHCO$_3$ and ethyl acetate. The layers are separated and the organic layer is dried with Na$_2$SO$_4$, filtered and concentrated. The resulting residue is purified by silica gel flash chromatography (ethyl acetate-dichloromethane, 0:1 to 1:6) to furnish 1-(3,3-difluoro-2,2-dimethyl-indan-1-yl)-5-ethoxymethyl-1H-imidazole; HRMS: (ESI) m/z 307.1634 [(M+H)$^+$: Calcd for C$_{17}$H$_{21}$N$_2$OF$_2$: 307.1622]; $^1$H NMR (400 MHz, CDCl$_3$) δ ppm 0.94 (d, J=2.5 Hz, 3 H), 1.28 (t, J=7.1 Hz, 3 H), 1.33 (d, J=3.3 Hz, 3 H), 3.51-3.68 (m, 2 H), 4.54-4.70 (m, 2 H), 5.58 (br. s., 1 H), 7.19 (s, 1 H), 7.23-7.26 (m, 1 H), 7.34 (s, 1 H), 7.55-7.63 (m, 2 H), 7.69-7.76 (m, 1 H).

Resolution of the enantiomers of the free base of this compound is achieved by chiral HPLC using a ChiralPak AS-H column with 9:1 heptane:ethanol to give (R)-1-(3,3-Difluoro-2,2-dimethyl-indan-1-yl)-5-ethoxymethyl-1H-imidazole (t$_r$=7.4 min) and (S)-1-(3,3-Difluoro-2,2-dimethyl-indan-1-yl)-5-ethoxymethyl-1H-imidazole (t$_r$=10.5 min).

The Following Compound can be Prepared in a Similar Fashion as Example 24

1-(3,3-Dimethyl-indan-1-yl)-5-ethoxymethyl-1H-imidazole

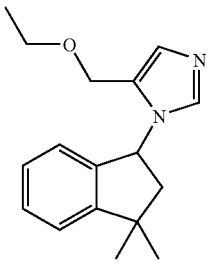 [SMILES: CCOCc1cncn1C1CC(C)(C)c2ccccc21]

$^1$H NMR (400 MHz, CDCl$_3$) of the free base: δ ppm 1.20 (t, J=6.9 Hz, 3 H), 1.28 (s, 3 H), 1.42 (s, 3 H), 2.10 (dd, J=13.0, 8.2 Hz, 1 H), 2.61 (dd, J=13.0, 7.7 Hz, 1 H), 3.45-3.53 (m, 2 H), 4.51 (dd, J=16.4, 12.9 Hz, 2 H), 5.82 (t, J=8.0 Hz, 1 H), 7.02-7.08 (m, 2 H), 7.20-7.30 (m, 2 H), 7.32-7.38 (m, 2 H); (ESI) m/z 271.1811 [(M+H)$^+$; calcd for C$_{17}$H$_{23}$N$_2$O: 271.1810].

Example 25 a)
1-Isothiochroman-4-yl-5-methoxymethyl-1H-imidazole

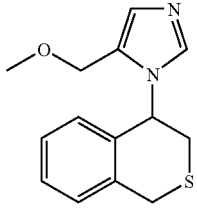 [SMILES: COCc1cncn1C1CSCc2ccccc21]

To a solution of LiAlH$_4$ (171 mg, 4.48 mmol) in THF (100 mL) at 0° C. is added a solution of 3-isothiochroman-4-yl-3H-imidazole-4-carboxylic acid methyl ester [which can be prepared from isothiochroman-4-ol (CAS#109819-33-2) as described in Example 2; MS: (ESI) m/z 275.2 (M+H)$^+$] (1.23 g, 4.48 mmol) in THF (50 mL). The reaction is permitted to stir for 4 hours, at which time it is quenched by the slow addition of water. The reaction mixture is then filtered, diluted with ethyl acetate and washed with saturated aqueous NaHCO$_3$. The organic layer is dried with Na$_2$SO$_4$, filtered, and concentrated. A portion of the resulting residue containing (3-isothiochroman-4-yl-3H-imidazol-4-yl)-methanol (240 mg, ca. 0.5 mmol) is then dissolved in THF (25 mL) and cooled to 48° C. The reaction mixture is then charged with a 1 M THF solution of potassium t-butoxide (0.75 mL, 0.75 mmol). The reaction is permitted to stir for 30 minutes and then charged with iodomethane (0.2 mL, 0.61 mmol). After 3.5 hours the reaction is quenched with saturated aqueous NaHCO$_3$ and further diluted with ethyl acetate. The organic layer is washed with saturated aqueous NaHCO$_3$, and then dried with Na$_2$SO$_4$, filtered, and concentrated. The resulting residue is purified by silica gel flash chromatography (methanol-dichloromethane, 0:1 to 1:19) to provide 1-isothiochroman-4-yl-5-methoxymethyl-1H-imidazole; MS: (ESI) m/z 261.1 (M+H); $^1$H NMR (400 MHz, CDCl$_3$) δ ppm 3.07-3.30 (m, 2 H), 3.33 (s, 3 H), 3.88 (br. s., 2 H), 4.35-4.57 (m, 2 H), 5.64 (t, J=5.2 Hz, 1 H), 6.93 (d, J=7.1 Hz, 1 H), 7.07 (s, 1 H), 7.15-7.28 (m, 3 H), 7.39 (s, 1 H). The HCl salt of the title compound can be prepared by dissolution in diethyl ether followed by treatment with an excess of 1N HCl in diethyl ether. The resulting heterogeneous solution is concentrated to furnish the HCl salt of 1-isothiochroman-4-yl-5-methoxymethyl-1H-imidazole.

The Following Compound can be Prepared in a Similar Fashion as Example 25

5-Benzyloxy-1-isothiochroman-4-yl-1H-imidazole

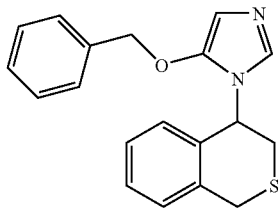 [SMILES: c1ccc(COc2cncn2C2CSCc3ccccc32)cc1]

$^1$H NMR of the free base (400 MHz, CDCl$_3$) δ ppm 3.00-3.30 (m, 2 H), 3.77-3.94 (m, 2 H), 4.43-4.67 (m, 4 H), 5.64 (t, J=5.18 Hz, 1 H), 6.92 (d, J=7.8 Hz, 1 H), 7.08 (s, 1 H), 7.12-7.44 (m, 9 H); MS: (ESI) m/z 337.2 (M+H)$^+$.

Examples for General Scheme 8

Example 26 a) 3-(2,2-Dimethyl-indan-1-yl)-3H-imidazole-4-carbaldehyde

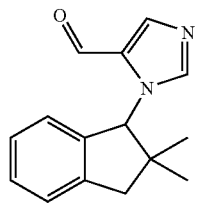 [SMILES: CC1(C)Cc2ccccc2C1n1cncc1C=O]

To a solution of [3-(2,2-dimethyl-indan-1-yl)-3H-imidazol-4-yl]-methanol (120 mg, 0.5 mmol), which can be prepared as described in Example 23, in 1,4-dioxane (5 mL) is added manganese (IV) oxide (434 mg, 5 mmol). The reaction is then heated at 90° C. for 1 hour, at which time the reaction is cooled to room temperature and filtered to furnish 3-(2,2-dimethyl-indan-1-yl)-3H-imidazole-4-carbaldehyde without the need for further purification; MS: (ESI) m/z 241.1 (M+H)$^+$.

b) cis- and trans-1-[3-(2,2-Dimethyl-indan-1-yl)-3H-imidazol-4-yl]-ethanol

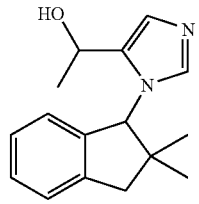 [SMILES: CC(O)c1cncn1C1c2ccccc2CC1(C)C]

To a solution of 3-(2,2-dimethyl-indan-1-yl)-3H-imidazole-4-carbaldehyde (120 mg, 0.5 mmol), in THF (5 mL) at 0° C. is added a 3.0 M diethyl ether solution of methylmagnesium bromide (0.25 mL, 0.75 mmol). The reaction is stirred for 15 minutes and then diluted with saturated aqueous NaHCO$_3$ and ethyl acetate. The layers are separated and the organic layer is dried with Na$_2$SO$_4$, filtered and concentrated to afford an approximately 1:1 diastereomeric mixture of cis- and trans-1-[3-(2,2-dimethyl-indan-1-yl)-3H-imidazol-4-yl]-ethanol without the need for further purification; HRMS: (ESI) m/z 257.1645 [(M+H)$^+$: Calcd for C$_{16}$H$_{21}$N$_2$O: 257.1654]; $^1$H NMR (400 MHz, CDCl$_3$) of diastereomer A: δ ppm 0.78 (s, 3 H), 1.27 (s, 3 H), 1.74 (d, J=6.57 Hz, 3 H), 2.70-3.06 (m, 2 H), 4.96 (q, J=6.48 Hz, 1 H), 5.61 (s, 1 H), 7.00 (s, 1 H), 7.05 (s, 1 H), 7.15-7.37 (m, 4 H). $^1$H NMR (400 MHz, CDCl$_3$) of Diastereomer B: δ ppm 0.88 (s, 3 H), 1.26 (s, 3 H), 1.69 (d, J=6.3 Hz, 3 H), 2.66-3.15 (m, 2 H), 5.02 (q, J=6.3 Hz, 1 H), 5.30 (s, 1 H), 6.94 (br. s., 1 H), 6.96 (br. s., 1 H), 7.10 (d, J=7.6 Hz, 1 H), 7.20 (t, J=6.2 Hz, 1 H), 7.27-7.35 (m, 2 H).

c) cis- AND trans-1-[3-((R)-2,2-dimethyl-indan-1-yl)-3H-imidazol-4-yl]-ethanol or cis- AND trans-1-[3-((S)-2,2-dimethyl-indan-1-yl)-3H-imidazol-4-yl]-ethanol Enantiomerically pure [3-(2,2-dimethyl-indan-1-yl)-3H-imidazol-4-yl]-methanol (LCX703), which can be prepared as described in Example 23, can be used to generate the requisite aldehyde starting material for this example. Upon Grignard addition the resulting diastereomeric mixture of enantiomerically pure cis- and trans-1-[3-(2,2-dimethyl-indan-1-yl)-3H-imidazol-4-yl]-ethanol can be separated to afford cis- AND trans-1-[3-((R)-2,2-dimethyl-indan-1-yl)-3H-imidazol-4-yl]-ethanol and cis- AND trans-1-[3-((S)-2,2-dimethyl-indan-1-yl)-3H-imidazol-4-yl]-ethanol via chiral HPLC using a ChiralPak AS-H column with 9:1 hexanes: isopropanol to give diastereomer LCY146 (t$_r$=7.3 min) and diastereomer LCY147 (t$_r$=9.2 min).

cis- AND trans-1-[3-((R)-2,2-dimethyl-indan-1-yl)-3H-imidazol-4-yl]-ethanol: HRMS: (ESI) m/z 257.1645 [(M+H)$^+$: Calcd for C$_{16}$H$_{21}$N$_2$O: 257.1654];

$^1$H NMR (400 MHz, CDCl$_3$) δ ppm 0.78 (s, 3 H), 1.27 (s, 3 H), 1.74 (d, J=6.6 Hz, 3 H), 2.70-3.06 (m, 2 H), 4.96 (q, J=6.5 Hz, 1 H), 5.61 (s, 1 H), 7.00 (s, 1 H), 7.05 (s, 1 H), 7.15-7.37 (m, 4 H).

cis- AND trans-1-[3-((S)-2,2-dimethyl-indan-1-yl)-3H-imidazol-4-yl]-ethanol HRMS: (ESI) m/z 257.1645 [(M+

H)⁺: Calcd for $C_{16}H_{21}N_2O$: 257.1654]; ¹H NMR (400 MHz, CDCl₃) δ ppm 0.88 (s, 3 H), 1.26 (s, 3 H), 1.69 (d, J=6.3 Hz, 3 H), 2.66-3.15 (m, 2 H), 5.02 (q, J=6.3 Hz, 1 H), 5.30 (s, 1 H), 6.94 (br. s., 1 H), 6.96 (br. s., 1 H), 7.10 (d, J=7.6 Hz, 1 H), 7.20 (t, J=6.2 Hz, 1 H), 7.27-7.35 (m, 2 H).

The Following Compound can be Prepared in a Similar Fashion as Example 26 cis- and trans-1-[3-(2,2-Dimethyl-2,3-dihydro-benzofuran-3-yl)-3H-imidazol-4-yl]-ethanol

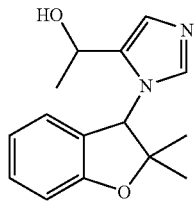 [SMILES: CC(O)c1cncn1C1c2ccccc2OC1(C)C]

~2.3:1 mixture of diastereomers: HRMS: (ESI) m/z 259.1441 [(M+H)⁺: Calcd for $C_{15}H_{18}N_2O_2$: 259.1447]; Major diastereomer: ¹H NMR (400 MHz, CDCl₃) of the free base: δ ppm 1.05 (s, 3 H), 1.53 (s, 3 H), 1.69-1.74 (m, 3 H), 4.82-4.92 (m, 1 H), 5.90 (s, 1 H), 6.82-7.43 (m, 6 H). Minor diastereomer: ¹H NMR (400 MHz, CDCl₃) of the free base: δ ppm 1.16 (s, 3 H), 1.53 (s, 3 H), 1.69-1.76 (m, 3 H), 5.00-5.08 (m, 1 H), 5.57 (s, 1 H), 6.82-7.43 (m, 6 H).

Examples for General Scheme 9

Example 27 a) [3-(3,3-Dimethyl-indan-1-yl)-3H-imidazol-4-yl]-methanol

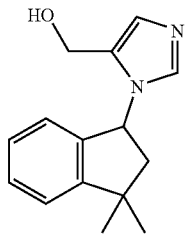

To a solution of 3-(3,3-dimethyl-indan-1-yl)-3H-imidazole-4-carboxylic acid methyl ester (1.31 g, 4.85 mmol), which can be prepared as described in Example 2, in THF (405 mL) at 0° C. is added LiAlH₄ (220 mg, 5.6 mmol). The reaction is permitted to stir at room temperature for 2 hours at which time the reaction is cooled to 0° C., charged with sodium fluoride (205 mg, 4.88 mmol), and diluted with water. The reaction is brought to room temperature and stirred overnight. The reaction is then filtered and the eluent is extracted three times with ethyl acetate. The combined organic extracts are dried with Na₂SO₄, filtered and concentrated. The resulting residue is purified by silica gel flash chromatography (methanol-dichloromethane, 0:1 to 1:10) to provide 3-(3,3-dimethyl-indan-1-yl)-3H-imidazol-4-yl]-methanol; MS: (ESI) m/z 243.1 (M+H)⁺.

b) 3-(3,3-Dimethyl-indan-1-yl)-3H-imidazole-4-carbaldehyde

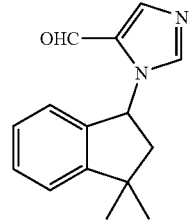 [SMILES: CC1(C)CC(n2cncc2C=O)c2ccccc21]

To a solution of 3-(3,3-dimethyl-indan-1-yl)-3H-imidazol-4-yl]-methanol (470 mg, 1.94 mmol) in 1,4-dioxane (20.0 mL) is added manganese (IV) oxide (1.7 g, 19.6 mmol) and the reaction is heated at reflux for 15 hours, at which time the reaction is filtered and concentrated. The resulting residue is purified by silica gel flash chromatography (ethyl acetate-dichloromethane, 0:1 to 1:19) to afford 3-(3,3-dimethyl-indan-1-yl)-3H-imidazole-4-carbaldehyde; MS: (ESI) m/z 241.0 (M+H)⁺.

c) 1-(3,3-Dimethyl-indan-1-yl)-5-vinyl-1H-imidazole

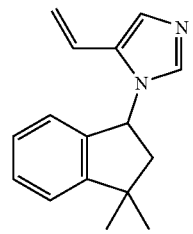 [SMILES: C=Cc1cncn1C1CC(C)(C)c2ccccc21]

To a solution of methyltriphenylphosphonium bromide/sodium amide [2.4 mmol/gram of salt (0.86 g, 2.06 mmol)] in THF (3.0 mL) is added a solution of 3-(3,3-dimethyl-indan-1-yl)-3H-imidazole-4-carbaldehyde (165 mg, 0.69 mmol) in THF (2 mL). The reaction is permitted to stir at room temperature for 30 minutes and is then quenched with saturated aqueous NH₄Cl. The reaction is diluted with ethyl acetate and the layers are separated. The aqueous layer is extracted with ethyl acetate and the organic layers are combined, dried with Na₂SO₄, filtered, and concentrated. The resulting residue is purified by silica gel flash chromatography (ethyl acetate-dichloromethane, 0:1 to 1:4) to furnish semi-pure 1-(3,3-dimethyl-indan-1-yl)-5-vinyl-1H-imidazole. Further purification via semi-preparative reverse phase HPLC (5 to 100% acetonitrile/water w/0.1% NH₄OH), affords 1-(3,3-dimethyl-indan-1-yl)-5-vinyl-1H-imidazole; MS: (ESI) m/z 239 (M+H)⁺; ¹H NMR (400 MHz, CDCl₃) δ ppm 1.29 (s, 3 H), 1.39 (s, 3 H), 2.11 (dd, J=13.0, 7.7 Hz, 1 H), 2.54 (dd, J=12.9, 7.8 Hz, 1 H), 5.20 (dd, J=11.4, 1.3 Hz, 1 H), 5.62 (dd, J=17.4, 1.3 Hz, 1 H), 5.72 (t, J=7.7 Hz, 1 H), 6.42 (dd, J=17.4, 11.1 Hz, 1 H), 7.09 (dd, J=7.6, 0.8 Hz, 1 H), 7.23-7.30 (m, 3 H), 7.32 (s, 1 H), 7.37 (t, J=7.5 Hz, 1 H). The HCl salt of the title compound can be prepared by dissolution in diethyl ether, followed by treatment with an excess of 1N HCl in diethyl ether. The resulting heterogeneous solution is concentrated to furnish the HCl salt of 1-(3,3-dimethyl-indan-1-yl)-5-vinyl-1H-imidazole.

The Following Compounds can be Prepared in a Similar Fashion as Example 27

1-(2,2-Dimethyl-indan-1-yl)-5-vinyl-1H-imidazole

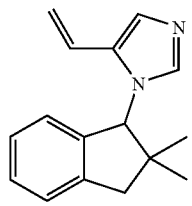 [SMILES: C=Cc1cncn1C1c2ccccc2CC1(C)C]

$^1$H NMR (400 MHz, CDCl$_3$) of the free base: δ ppm 0.80 (s, 3 H), 1.29 (s, 3 H), 2.70-3.06 (m, 2 H), 5.28 (s, 1 H), 5.53 (d, J=11.1 Hz, 1 H), 5.83 (d, J=17.4 Hz, 1 H), 6.63 (dd, J=17.3, 11.2 Hz, 1 H), 7.17-7.44 (m, 6 H); HRMS: (ESI) m/z 239.1552 [(M+H)$^+$: Calcd for C$_{16}$H$_{19}$N$_2$: 239.1548]

1-(4,4-Dimethyl-1,2,3,4-tetrahydro-naphthalen-1-yl)-5-vinyl-1H-imidazole

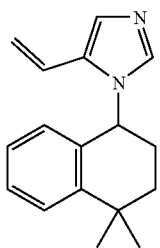 [SMILES: C=Cc1cncn1C1CCC(C)(C)c2ccccc21]

$^1$H NMR (400 MHz, CDCl$_3$) of the free base: δ ppm 1.34 (s, 3 H), 1.39 (s, 3 H), 1.66-1.80 (m, 2 H), 2.09-2.24 (m, 2 H), 5.20 (dd, J=11.2, 1.1 Hz, 1 H), 5.34 (t, J=6.1 Hz, 1 H), 5.62 (dd, J=17.7, 1.3 Hz, 1 H), 6.42 (dd, J=1.7.4, 11.1 Hz, 1 H), 6.87 (d, J=7.8 Hz, 1 H), 7.09-7.16 (m, 2 H), 7.25 (s, 1 H), 7.31 (t, J=7.2 Hz, 1 H), 7.43 (dd, J=8.0, 1.1 Hz, 1 H); MS: (ESI) m/z 253.1 (M+H)$^+$.

Example 28 a) 1-(3,3-Dimethyl-indan-1-yl)-5-ethyl-1H-imidazole

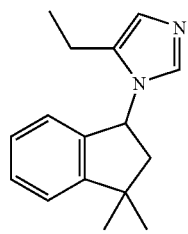 [SMILES: CCc1cncn1C1CC(C)(C)c2ccccc21]

To a solution of 1-(3,3-dimethyl-indan-1-yl)-5-vinyl-1H-imidazole (210 mg, 0.882 mmol), which can be prepared as described in Example 27, in methanol (10 mL) under a nitrogen atmosphere is added 5 wt % palladium on carbon (~200 mg, ~0.09 mmol). The atmosphere of the reaction vessel is evacuated of and backfilled with hydrogen gas (balloon pressure). The reaction is permitted to stir under a hydrogen atmosphere for 2 hours and is then diluted with ethyl acetate and filtered through a pad of Celite®. The reaction mixture is concentrated and the residue is purified by silica gel flash chromatography (ethyl acetate-dichloromethane, 1:19 to 1:4) to provide 1-(3,3-dimethyl-indan-1-yl)-5-ethyl-1H-imidazole; HRMS: (ESI) m/z 241.1716 [(M+H)$^+$; calcd for C$_{16}$H$_{21}$N$_2$: 241.1705]; $^1$H NMR (400 MHz, CDCl$_3$) δ ppm 1.29 (s, 3 H), 1.31 (t, J=7.6 Hz, 3 H), 1.42 (s, 3 H), 2.04 (dd, J=12.9, 8.3 Hz, 1 H), 2.51-2.68 (m, 3 H), 5.59 (t, J=8.0 Hz, 1 H), 6.85 (d, J=1.0 Hz, 1 H), 7.04 (d, J=6.8 Hz, 1 H), 7.21-7.29 (m, 3 H), 7.33-7.38 (m, 1 H); The HCl salt of the title compound can be prepared by dissolution in diethyl ether followed by treatment with an excess of 1N HCl in diethyl ether. The resulting heterogeneous solution is concentrated to furnish the HCl salt of 1-(3,3-dimethyl-indan-1-yl)-5-ethyl-1H-imidazole.

b) (R)- and (S)-1-(3,3-Dimethyl-indan-1-yl)-5-ethyl-1H-imidazole

The resolution of the enantiomers of the free base of the titled compound is achieved by chiral HPLC using a ChiralPak IA column with 9:1 heptane:ethanol to give (R)-1-(3,3-Dimethyl-indan-1-yl)-5-ethyl-1H-imidazole (t$_r$=13 min) and (S)-1-(3,3-Dimethyl-indan-1-yl)-5-ethyl-1H-imidazole (t$_r$=17 min).

The Following Compounds can be Prepared in a Similar Fashion as Example 28

1-(2,2-Dimethyl-indan-1-yl)-5-ethyl-1H-imidazole

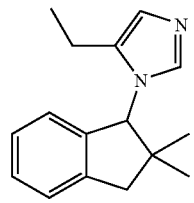 [SMILES: CCc1cncn1C1c2ccccc2CC1(C)C]

$^1$H NMR (400 MHz, CDCl$_3$) of the free base: δ ppm 0.78 (s, 3 H), 1.26 (s, 3 H), 1.38 (t, J=7.5 Hz, 3 H), 2.69 (q, J=7.6 Hz, 2 H), 2.76-3.03 (m, 2 H), 5.09 (s, 1 H), 6.87 (s, 1 H), 7.00 (s, 1 H), 7.15 (d, J=7.6 Hz, 1 H), 7.20-7.36 (m, 3 H); HRMS: (ESI) m/z 241.1701 [(M+H)$^+$: Calcd for C$_{16}$H$_{21}$N$_2$: 241.1705]

1-(3,3-Dimethyl-indan-1-yl)-5-propyl-1H-imidazole

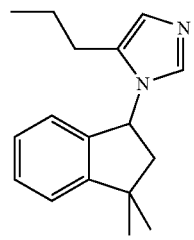 [SMILES: CCCc1cncn1C1CC(C)(C)c2ccccc21]

¹H NMR (400 MHz, CDCl₃) of the free base: δ ppm 1.03 (t, J=7.4 Hz, 3 H), 1.29 (s, 3 H), 1.42 (s, 3 H), 1.67-1.78 (m, 2 H), 2.04 (dd, J=12.9, 8.3 Hz, 1 H), 2.49-2.64 (m, 3 H), 5.59 (t, J=8.0 Hz, 1 H), 6.85 (s, 1 H), 7.03 (d, J=7.6 Hz, 1 H), 7.20-7.29 (m, 3 H), 7.35 (t, J=7.4 Hz, 1 H); (ESI) m/z 255.1854 [(M+H)⁺; calcd for C₁₇H₂₃N₂: 255.1861].

1-(3,3-Dimethyl-indan-1-yl)-5-(2-ethoxy-ethyl)-1H-imidazole

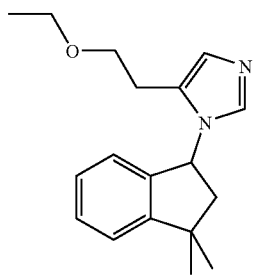 [SMILES: CCOCCc1cncn1C1CC(C)(C)c2ccccc21]

¹H NMR (400 MHz, CDCl₃) of the free base: δ ppm 1.19 (t, J=6.9 Hz, 3 H), 1.28 (s, 3 H), 1.42 (s, 3 H), 1.98-2.06 (m, 1 H), 2.55 (dd, J=12.9, 7.6 Hz, 1 H), 2.83-2.97 (m, 2 H), 3.51 (q, J=6.9 Hz, 2 H), 3.69 (t, J=6.8 Hz, 2 H), 5.73 (t, J=8.0 Hz, 1 H), 6.89 (s, 1 H), 7.03 (d, J=7.6 Hz, 1 H), 7.23 (t, J=7.3 Hz, 1 H), 7.27 (d, J=7.6 Hz, 2 H), 7.34 (t, J=7.3 Hz, 1 H); (ESI) m/z 285.1975 [(M+H)⁺; calcd for C₁₈H₂₅N₂O: 285.1967].

5-Butyl-1-(3,3-dimethyl-indan-1-yl)-1H-imidazole

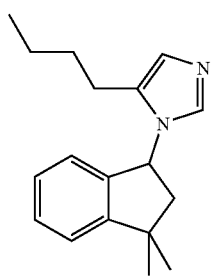 [SMILES: CCCCc1cncn1C1CC(C)(C)c2ccccc21]

¹H NMR (400 MHz, CDCl₃) of the free base: δ ppm 0.95 (t, J=7.5 Hz, 3 H), 1.29 (s, 3 H), 1.38-1.48 (m, 5 H), 1.63-1.72 (m, 2 H), 1.98-2.08 (m, 1 H), 2.50-2.66 (m, 3 H), 5.59 (t, J=8.0 Hz, 1 H), 6.84 (s, 1 H), 7.03 (d, J=7.6 Hz, 1 H), 7.20-7.29 (m, 3 H), 7.35 (t, J=7.3 Hz, 1 H); (ESI) m/z 269.2017 [(M+H)⁺; calcd for C₁₈H₂₅N₂: 269.2018].

1-(4,4-Dimethyl-1,2,3,4-tetrahydro-naphthalen-1-yl)-5-ethyl-1H-imidazole

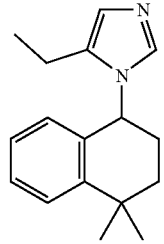 [SMILES: CCc1cncn1C1CCC(C)(C)c2ccccc21]

¹H NMR (400 MHz, CDCl₃) of the free base: δ ppm 1.32 (t, J=7.5 Hz, 3 H), 1.36 (s, 3 H), 1.39 (s, 3 H), 1.67-1.88 (m, 2 H), 2.05-2.27 (m, 2 H), 2.47-2.70 (m, 2 H), 5.21 (dd, J=7.8, 5.6 Hz, 1 H), 6.75 (d, J=7.8 Hz, 1 H), 6.85 (s, 1 H), 7.05-7.12 (m, 1 H), 7.13 (s, 1 H), 7.24-7.31 (m, 1 H), 7.38-7.43 (m, 1 H); MS: (ESI) m/z 255.2 (M+H)⁺. T The resolution of the enantiomers of the free base of the titled compound is achieved by chiral HPLC using a ChiralPak IA column with 90:10 heptane:isopropanol to give the two enantiomers with t_r=16.0 min and t_r=18.5 min.

Examples for General Scheme 10

Example 29 a) (R)- and (S)-5-Difluoromethyl-1-(2,2-dimethyl-2,3-dihydro-benzofuran-3-yl)-1H-imidazole

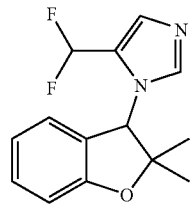 [SMILES: CC1(C)Oc2ccccc2C1n1cncc1C(F)F]

To a solution of 3-(2,2-dimethyl-2,3-dihydro-benzofuran-3-yl)-3H-imidazol-4-yl]-methanol (1.94 g, 7.94 mmol), which can be prepared as described in Example 23 in 1,4-dioxane (40 mL) is added manganese(IV) oxide (6.9 g, 79 mmol) in two portions. The reaction is heated at reflux until LC-MS analysis indicates complete consumption of the alcohol starting material. The reaction is cooled to room temperature, filtered, and concentrated. The resulting aldehyde is taken directly into the next reaction.

To a solution of the aldehyde prepared above (224 mg, 0.926 mmol) in 1,2-dichloroethane (5 mL) is added (diethylamino)sulfur trifluoride (DAST) (0.360 mL, 2.8 mmol). The reaction is heated at 90° C. for 6 hours. The solution is cooled to room temperature, quenched with saturated aqueous NaHCO₃, and diluted with dichloromethane. The layers are separated and the organic layer is washed twice with saturated aqueous NaHCO₃, dried with Na₂SO₄, filtered, and concentrated. The resulting residue is purified by silica gel flash chromatography (ethyl acetate-heptane, 1:10) to afford 5-difluoromethyl-1-(2,2-dimethyl-2,3-dihydro-benzofuran-3-yl)-1H-imidazole; MS: (ESI) m/z 265 (M+H).+ The HCl salt of the title compound can be prepared by dissolution in diethyl ether, followed by treatment with an excess of 1N HCl in diethyl ether. The resulting heterogeneous solution is concentrated to furnish the HCl salt of 5-difluoromethyl-1-(2,2-dimethyl-2,3-dihydro-benzofuran-3-yl)-1H-imidazole; $^1$H NMR (400 MHz, CD$_3$OD) δ ppm 1.09 (s, 3 H), 1.50 (s, 3 H), 5.69 (s, 1 H), 6.70 (t, J=54.69 Hz, 1 H), 6.93 (d, J=8.1 Hz, 1 H), 7.01 (t, J=7.5 Hz, 1 H), 7.12 (br. s., 1 H), 7.33 (d, J=7.3 Hz, 1 H), 7.39 (t, J=7.7 Hz, 1 H), 7.87 (br. s., 1 H).

Resolution of the enantiomers of the free base of this compound is achieved by chiral HPLC using a ChiralPak IA column with 9:1 heptane:ethanol to give (R)-5-Difluoromethyl-1-(2,2-dimethyl-2,3-dihydro-benzofuran-3-yl)-1H-imidazole (t$_r$=1.3.5 min) and (S)-5-Difluoromethyl-1-(2,2-dimethyl-2,3-dihydro-benzofuran-3-yl)-1H-imidazole (t$_r$=20.9 min)

The Following Compounds can be Prepared in a Similar Fashion as Example 29

(R)- and (S)-1-(3,3-Difluoro-2,2-dimethyl-indan-1-yl)-5-difluoromethyl-1H-imidazole

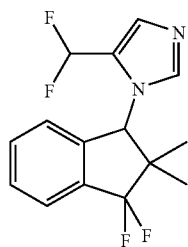 [SMILES: CC1(C)C(n2cncc2C(F)F)c2ccccc2C1(F)F]

$^1$H NMR (400 MHz, CDCl$_3$) of the free base: δ ppm 0.95 (d, J=2.8 Hz, 3 H), 1.31 (d, J=3.3 Hz, 3 H), 5.58 (d, J=3.3 Hz, 1 H), 6.86 (t, J=52.7 Hz, 1 H), 7.23 (s, 1 H), 7.30-7.35 (m, 1 H), 7.39 (br. s., 1 H), 7.54-7.63 (m, 2 H), 7.67-7.76 (m, 1 H); MS: (ESI) m/z 299.0 (M+H)+.

Resolution of the enantiomers of the free base of this compound is achieved by chiral HPLC using a ChiralPak AS-H column with 9:1 heptane:ethanol to give LDE270 (t$_r$=10.0 min) and LDE272 (t$_r$=14.5 min)

3-(5-Difluoromethyl-imidazol-1-yl)-2,2-dimethyl-indan-1-one

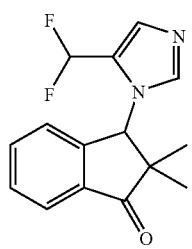 [SMILES: CC1(C)C(=O)c2ccccc2C1n1cncc1C(F)F]

$^1$H NMR (400 MHz, CDCl$_3$) of the free base: δ ppm 0.89 (s, 3 H), 1.41 (s, 3 H), 5.83 (s, 1 H), 6.93 (t, J=52.6 Hz, 1 H), 7.17 (s, 1 H), 7.50 (d, J=7.8 Hz, 2 H), 7.52 (br. s., 1 H), 7.67 (t, J=7.5 Hz, 1 H), 7.79 (t, J=8.1 Hz, 1 H), 7.94 (d, J=7.6 Hz, 1 H); HRMS: (ESI) m/z 277.1149 [(M+H)+: Calcd for C$_{15}$H$_{15}$N$_2$OF$_2$: 277.1152]

Examples for Compounds not Covered by General Schemes

Example 30 a) 3-Imidazol-1-yl-2,2-dimethyl-indan-1-one

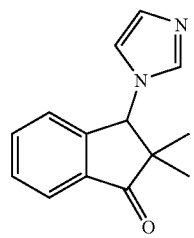 [SMILES: CC1(C)C(=O)c2ccccc2C1n1ccnc1]

To a solution of trifluoromethansulfonic anhydride (1.13 mL, 6.75 mmol) in dichloromethane (10 mL) at −78° C. is added, via cannula, a solution of diisopropylethylamine (1.8 mL, 10.1 mmol) and 3-hydroxy-2,2-dimethyl-indan-1-one, prepared as described in Example 20, (400 mg, 2.25 mmol) in dichloromethane (5 mL). The reaction is stirred at −78° C. for 10 minutes and then is placed at −10° C. for 10 minutes. The reaction is then re-cooled to −78° C. and a solution of imidazole (920 mg, 13.5 mmol) in dichloromethane (12 mL) is added via cannula. The reaction is then placed at room temperature for 1 hour, at which time it is diluted with saturated aqueous NaHCO$_3$ and ethyl acetate. The layers are separated and the aqueous layer is extracted two times with ethyl acetate. The combined organic layers are dried with MgSO$_4$, filtered, and concentrated. The resulting residue is purified by silica gel flash chromatography (ethyl acetate-dichloromethane, 1:3 to 1:0), to afford 3-imidazol-1-yl-2,2-dimethyl-indan-1-one; MS: (ESI) m/z 227 (M+H)+; $^1$H NMR: (400 MHz, CDCl$_3$) δ ppm 0.80 (s, 3 H), 1.41 (s, 3 H), 5.52 (s, 1 H), 6.73 (s, 1 H), 7.12 (s, 1 H), 7.51 (d, J=7.6 Hz, 1 H), 7.56 (s, 1 H), 7.62 (t, J=7.5 Hz, 1 H), 7.70-7.80 (m, 1 H), 7.91 (d, J=7.6 Hz, 1 H).

b) (R)- and (S)-3-Imidazol-1-yl-2,2-dimethyl-indan-1-one

The resolution of the enantiomers of the this compound is achieved by chiral HPLC using a ChiralPak IA column with 4:1 heptane-ethanol to give (R)-3-Imidazol-1-yl-2,2-dimethyl-indan-1-one (t$_r$=5.8 min) and (S)-3-Imidazol-1-yl-2,2-dimethyl-indan-1-one (t$_r$=7.7 min)

Example 31 a) 5-Trifluoromethyl-1H-imidazole

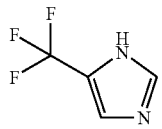

To a solution of 3,3-dibromo-1,1,1-trifluoro-propan-2-one (CAS#431-67-4, 10 g, 37.1 mmol) in water (40 mL) is added sodium acetate (6.1 g, 74.2 mmol). The reaction is heated at reflux for 1 hour and then cooled to room temperature, at which time a 37 wt % aqueous solution of formaldehyde (2.8 mL, 37.1 mmol) is added followed by a 28% aqueous ammonium hydroxide solution (50 mL), which leads to the formation of a white precipitate. The reaction is permitted to stir for 6 hours, at which time the crystalline precipitate is filtered and washed with water. The resulting crystals are dried in vacuo to provide 5-trifluoromethyl-1H-imidazole; $^1$H NMR: (400 MHz, CDCl$_3$) δ ppm 7.42 (s, 1 H), 7.73 (s, 1 H), 9.49 (br. s., 1 H).

b) (R)- and (S)-1-(2,2-Dimethyl-indan-1-yl)-5-trifluoromethyl-1H-imidazole

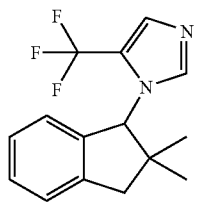 [SMILES: CC1(C)Cc2ccccc2C1n1cncc1C(F)(F)F]

To a solution of 2,2-dimethyl-indan-1-ol, prepared as described in Example 10, (400 mg, 2.47 mmol) in THF (30 mL) at 0° C. is added 5-trifluoromethyl-1H-imidazole (510 mg, 3.75 mmol), triphenylphosphine (982 mg, 3.75 mmol) and a 40 wt % solution of dimethyl azodicarboxylate in toluene (1.4 mL, 3.75 mmol). The reaction is then placed at room temperature and permitted to stir for 1 hour, at which time it is diluted with diethyl ether and water, and is then charged with Na$_2$CO$_3$ (1.9 g, 17.9 mmol). The reaction is permitted to stir for 10 minutes and the layers are separated. The organic layer is washed with brine and the aqueous layers are combined and back-extracted with diethyl ether. The organic layers are combined, dried with MgSO$_4$, filtered, and concentrated. The resulting residue is purified by silica gel flash chromatography (ethyl acetate-hexanes, 15:85 to 1:1) to afford 1-(2,2-dimethyl-indan-1-yl)-5-trifluoromethyl-1H-imidazole; HRMS: (ESI) m/z 281.1266 [(M+H)$^+$; calcd for C$_{15}$H$_{15}$F$_3$N$_3$: 281.1276]. The HCl salt of the title compound can be prepared by dissolution in diethyl ether, followed by treatment with an excess of 1N HCl in diethyl ether. The resulting heterogeneous solution is concentrated to furnish the HCl salt of 1-(2,2-dimethyl-indan-1-yl)-5-trifluoromethyl-1H-imidazole; $^1$H NMR (400 MHz, CD$_3$OD) δ ppm 0.91 (s, 3 H), 1.29 (s, 3 H), 2.83-3.24 (m, 2 H), 5.46 (s, 1 H), 7.25-7.50 (m, 4 H), 8.12 (s, 1 H), 8.18 (s, 1 H).

The resolution of the enantiomers of the free base of this compound is achieved by chiral HPLC using a ChiralPak IA column with 95:5 heptane:ethanol to give LCX758 (t$_r$=11 min) and LCX759 (t$_r$=13 min).

Example 32 a) (3H-Imidazol-4-yl)-pyrrolidin-1-yl-methanone

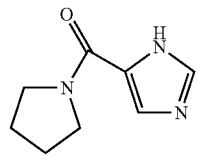 [SMILES: O=C(c1cnc[nH]1)N1CCCC1]

A solution of methyl 4-imidazolecarboxylate (CAS#17325-26-7, 460 mg, 3.6 mmol), and pyrrolidine (7 mL) is heated by microwave irradiation at 110° C. for 3.5 hours in a sealed vessel. The reaction is then concentrated to dryness. The resulting residue is purified by silica gel flash chromatography (methanol-dichloromethane, 0:1 to 1:10) to furnish (3H-imidazol-4-yl)-pyrrolidin-1-yl-methanone; MS: (ESI) m/z 166.2 (M+H)$^+$.

b) 4-[5-(Pyrrolidine-1-carbonyl)-imidazol-1-yl]-isothiochroman-7-carbonitrile

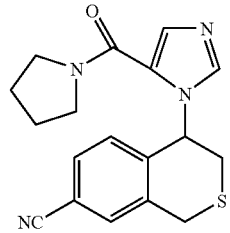

To a solution of 4-hydroxy-isothiochroman-7-carbonitrile, which can be prepared as described in Example 12, (300 mg, 1.6 mmol) in THF (20 mL) is added (3H-imidazol-4-yl)-pyrrolidin-1-yl-methanone (200 mg, 1.2 mmol), and triphenylphosphine (420 mg, 1.6 mmol). The reaction is cooled to 0° C. and diisopropyl azodicarboxylate (310 μL, 1.6 mmol) is added. The reaction is permitted to warm to room temperature and stirred until LC-MS analysis indicates complete consumption of 4-hydroxy-isothiochroman-7-carbonitrile. The reaction mixture is diluted with saturated aqueous NaHCO$_3$ and ethyl acetate. The layers are separated and the organic layer is dried with Na$_2$SO$_4$, filtered, and concentrated. The resulting residue is purified by silica gel flash chromatography (ethyl acetate-dichloromethane, 0:1 to 1:1) to afford 4-[5-(Pyrrolidine-1-carbonyl)-imidazol-1-yl]-isothiochroman-7-carbonitrile; MS: (ESI) m/z 339.2 (M+H)$^+$; $^1$H NMR (400 MHz, CDCl$_3$) δ ppm 1.88-2.08 (m, 4 H), 3.17-3.37 (m, 2 H), 3.53-3.68 (m, 2 H), 3.69-3.77 (m, 2 H), 3.79-3.98 (m, 2 H), 6.55 (t, J=4.6 Hz, 1 H), 7.19 (d, J=8.1 Hz, 1 H), 7.39 (s, 1 H), 7.43-7.48 (m, 2 H), 7.50 (s, 1 H). The HCl salt of the title compound can be prepared by dissolution in diethyl ether followed by treatment with an excess of 1N HCl in diethyl ether. The resulting heterogeneous solution is concentrated to furnish the HCl salt of 4-[5-(Pyrrolidine-1-carbonyl)-imidazol-1-yl]-isothiochroman-7-carbonitrile.

The Following Compounds can be Prepared in a Similar Fashion as Example 32

3-(2,2-Dimethyl-indan-1-yl)-3H-imidazole-4-carboxylic acid benzylamide

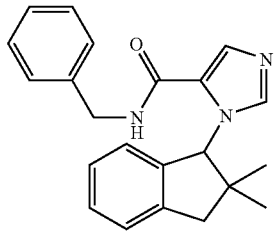 [SMILES: CC1(C)Cc2ccccc2C1n1cncc1C(=O)NCc1ccccc1]

¹H NMR (400 MHz, CDCl₃) of the free base: δ ppm 0.76 (s, 3 H), 1.26 (s, 3 H), 2.69-3.01 (m, 2 H), 4.63-4.67 (m, 2 H), 6.35 (br. s., 1 H), 6.42 (s, 1 H), 7.00 (s, 1 H), 7.22-7.42 (m, 9 H), 7.47 (s, 1 H); MS: (ESI) m/z 346.2 (M+H)⁺.

3-(2,2-Dimethyl-indan-1-yl)-3H-imidazole-4-carboxylic acid 4-chloro-benzylamide

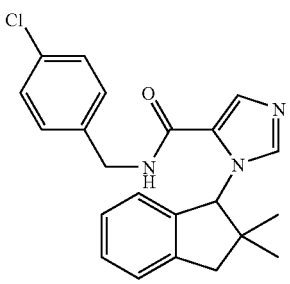 [SMILES: CC1(C)Cc2ccccc2C1n1cncc1C(=O)NCc1ccc(Cl)cc1]

¹H NMR (400 MHz, CDCl₃) of the free base: δ ppm 0.80 (s, 3 H), 1.26 (s, 3 H), 2.66-3.06 (m, 2 H), 6.35 (s, 1 H), 7.05 (s, 1 H), 7.25-7.40 (m, 6 H), 7.55-7.62 (m, 2 H), 7.67 (s, 1 H), 7.77 (br. s., 1 H); MS: (ESI) m/z 366.13, 368.02 (M+H)⁺.

Example 33 a) Acetic acid [(2-bromo-benzyl)-methyl-carbamoyl]-methyl ester

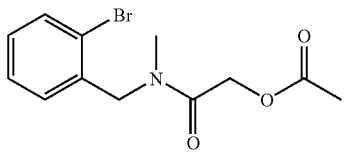 [SMILES: CC(=O)OCC(=O)N(C)Cc1ccccc1Br]

To a solution of 2-bromo-N-methyl benzylamine (CAS#698-19-1, 0.57 mL, 3.89 mmol) in THF (10 mL) at 0° C. is added triethylamine (0.98 mL, 1.03 mmol) followed by acetoxyacetylchloride (0.63 mL, 5.86 mmol). The reaction is permitted to warm to room temperature and after two hours the reaction is quenched with saturated aqueous NaHCO₃ and diluted with ethyl acetate. The layers are separated and the organic layer is dried with Na₂SO₄, filtered, and concentrated. The resulting residue is purified by silica gel flash chromatography (ethyl acetate-hexanes, 1:4 to 3:2) to provide acetic acid [(2-bromo-benzyl)-methyl-carbamoyl]-methyl ester; MS: (ESI) m/z 300.1, 302.1 (M+H)⁺.

b) N-(2-Bromo-benzyl)-2-hydroxy-N-methyl-acetamide

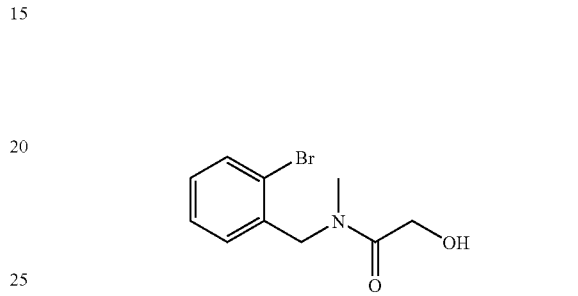

To a solution of acetic acid [(2-bromo-benzyl)-methyl-carbamoyl]-methyl ester (11.0 g, 36.8 mmol) in methanol (250 mL) is added a solution of potassium carbonate (7.63 g, 55.2 mmol) in water (45 mL). After stirring for 90 minutes the reaction is concentrated to near dryness and then dissolved in dichloromethane. The resulting solution is washed with brine, dried with Na₂SO₄, filtered, and concentrated. The resulting residue is purified by silica gel flash chromatography (methanol-dichloromethane, 1:99 to 3:47) to furnish N-(2-bromo-benzyl)-2-hydroxy-N-methyl-acetamide; MS: (ESI) m/z 258.1, 260.1 (M+H)⁺.

c) 3-{[(2-Bromo-benzyl)-methyl-carbamoyl]-methyl}-3H-imidazole-4-carboxylic acid methyl ester

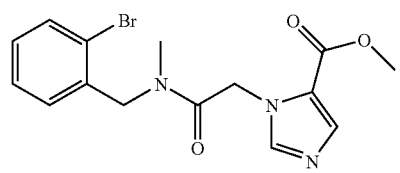 [SMILES: COC(=O)c1cncn1CC(=O)N(C)Cc1ccccc1Br]

To a solution of N-(2-bromo-benzyl)-2-hydroxy-N-methyl-acetamide (1.02 g, 3.95 mmol) in THF (40 mL) at 0° C. is added triphenylphosphine (1.15 g, 4.36 mmol), methyl 4-imidazolecarboxylate (CAS#17325-26-7, 0.50 g, 3.96 mmol) and diisopropyl azodicarboxylate (0.85 mL, 4.36 mmol). The reaction is permitted to warm to room temperature and allowed to stir 18 hours. The reaction is then adsorbed directly onto silica gel and submitted to silica gel flash chromatography (diethylamine-methanol-dichloromethane, 1:3:96) to provide 3-{[(2-bomo-benzyl)-methylcarbamoyl]-methyl}-3H-imidazole-4-carboxylic acid methyl ester; MS: (ESI) m/z 366.2, 368.2 (M+H)⁺.

d) 3-(2-Methyl-3-oxo-1,2,3,4-tetrahydro-isoquinolin-4-yl)-3H-imidazole-4-carboxylic acid methyl ester

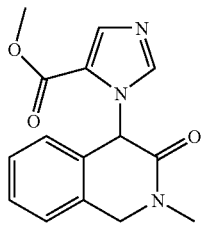

To a solution of 3-{[(2-bomo-benzyl)-methyl-carbamoyl]-methyl}-3H-imidazole-4-carboxylic acid methyl ester (542 mg, 1.43 mmol) in DMF (10 mL) is added CsCO₃ (1.39 g, 4.3 mmol) and a catalytic amount of bis(triphenylphosphine)palladium(II) dichloride. The reaction is heated at reflux for 2 hours and then concentrated to dryness. The resulting residue is purified by silica gel flash chromatography (diethylamine-methanol-dichloromethane, 1:2:97) to provide 3-(2-methyl-3-oxo-1,2,3,4-tetrahydro-isoquinolin-4-yl)-3H-imidazole-4-carboxylic acid methyl ester; MS: (ESI) m/z 286.2 (M+H)⁺.

e) 3-(2-Methyl-1,2,3,4-tetrahydro-isoquinolin-4-yl)-3H-imidazole-4-carboxylic acid methyl ester

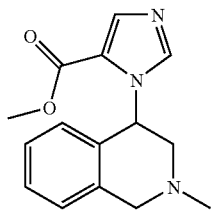

To a solution of 3-(2-methyl-3-oxo-1,2,3,4-tetrahydro-isoquinolin-4-yl)-3H-imidazole-4-carboxylic acid methyl ester (90 mg, 0.316 mmol) in THF (2 mL) is added a 1 M solution of borane in THF (1.6 mL, 1.6 mmol). The reaction is permitted to stir for 1 hour, at which time it is quenched with 1 M aqueous HCl. The acidified reaction is permitted to stir for one hour and then is treated with 1 N aqueous NaOH until the pH is >7. The mixture is then extracted with dichloromethane. The organic extract is dried over Na₂SO₄, filtered, and concentrated. The resulting residue is purified by semi-preparative reverse phase HPLC (5 to 100% acetonitrile/water w/0.1% NH₄OH) to furnish 3-(2-methyl-1,2,3,4-tetrahydro-isoquinolin-4-yl)-3H-imidazole-4-carboxylic acid methyl ester; MS: (ESI) m/z 272.2 (M+H)⁺. The HCl salt of the title compound can be prepared by dissolution in diethyl ether followed by treatment with an excess of 1N HCl in diethyl ether. The resulting heterogeneous solution is concentrated to furnish the HCl salt of 3-(2-methyl-1,2,3,4-tetrahydro-isoquinolin-4-yl)-3H-imidazole-4-carboxylic acid methyl ester; ¹H NMR (400 MHz, CDCl₃) δ ppm 2.39 (s, 3 H), 2.80 (dd, J=12.4, 3.8 Hz, 1 H), 2.94-3.02 (m, 1 H), 3.40 (d, J=15.2 Hz, 1 H), 3.91 (s, 3 H), 3.90-3.96 (m, 1 H), 6.35 (m, 1 H), 7.11-7.23 (m, 3 H), 7.24-7.32 (m, 1 H), 7.50 (s, 1 H), 7.77 (s, 1 H).

Example 34 a) (R)- and (S)-3-{4-[(E)-Methoxyimino]-2,2-dimethyl-1,2,3,4-tetrahydro-naphthalen-1-yl}-3H-imidazole-4-carboxylic acid methyl ester

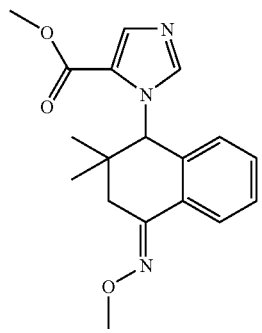 [SMILES: CO/N=C1\CC(C)(C)C(n2cncc2C(=O)OC)c2ccccc21]

To a solution of (R)- or (S)-3-(2,2-dimethyl-4-oxo-1,2,3,4-tetrahydro-naphthalen-1-yl)-3H-imidazole-4-carboxylic acid methyl ester (0.091 g, 0.299 mmol), which can be prepared as described in Example 13, and methoxyamine hydrochloride (0.076 g, 0.897 mmol) in methanol (2 mL) is added pyridine (0.24 g, 2.99 mmol) and the mixture is heated to 50° C. After 1.5 hours, the mixture is diluted with ethyl acetate and washed twice with aqueous copper sulfate, twice with 1:9 v/v aqueous ammonium hydroxide-saturated aqueous ammonium chloride, water, and brine. The organic layer is dried over MgSO₄, filtered, and concentrated to furnish (R)- or (S)-3-{4-[(E)-methoxyimino]-2,2-dimethyl-1,2,3,4-tetrahydro-naphthalen-1-yl}-3H-imidazole-4-carboxylic acid methyl ester as a 19:1 ratio of geometric isomer without the need for further purification. ¹H NMR (400 MHz, MeOD) δ ppm 0.94 (s, 3 H), 1.10 (s, 3 H), 2.52 (d, J=17.9 Hz, 1 H), 2.99 (d, J=17.9 Hz, 1 H), 4.03 (s, 3 H), 4.06 (s, 3 H), 6.65 (s, 1 H), 7.17-7.26 (m, 1 H), 7.41-7.49 (m, 2 H), 8.18-8.22 (m, 2 H), 8.27 (br. s., 1 H).

The title compounds can also be obtained from the racemic material by HPLC resolution using the ChiralPak AS-H column with a heptane/reagent alcohol, 19:1 mobile phase to give (R)-3-{4-[(E)-Methoxyimino]-2,2-dimethyl-1,2,3,4-tetrahydro-naphthalen-1-yl}-3H-imidazole-4-carboxylic acid methyl ester (t,=10.6 min) and (S)-3-{4-[(E)-Methoxyimino]-2,2-dimethyl-1,2,3,4-tetrahydro-naphthalen-1-yl}-3H-imidazole-4-carboxylic acid methyl ester (t,=12.3 min).

Example 35 a) (R)- or (S)-4-(5-Hydroxymethyl-imidazol-1-yl)-3,3-dimethyl-3,4-dihydro-2H-naphthalen-1-one O-methyl-oxime

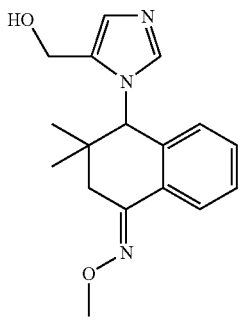 [SMILES: CO/N=C1\CC(C)(C)C(n2cncc2CO)c2ccccc21]

To a solution of (R)- or (S)-3-{4-[(E)-methoxyimino]-2,2-dimethyl-1,2,3,4-tetrahydro-naphthalen-1-yl}-3H-imidazole-4-carboxylic acid methyl ester (ca. 100 mg, ca. 0.299 mmol), which can be prepared as described in Example 34, in dichloromethane (2 mL) at −78° C. is added DIBAL-H (1.0M in hexane, 0.91 mL, 0.91 mmol) portion wise over 45 minutes. Methanol (0.1 mL) is then added and the cooling bath is removed. The mixture is diluted with dichloromethane and an aqueous solution of Rochelle's salt is added. The mixture is vigorously stirred for 1 hour, further diluted with aqueous Rochelle's salt, then extracted with dichloromethane. The organic extract is dried over MgSO$_4$, filtered, and concentrated to give a residue, which is purified by silica gel flash chromatography (dichloromethane-methanol, 97:3 to 19:1) to give (R)- or (S)-4-(5-hydroxymethyl-imidazol-1-yl)-3,3-dimethyl-3,4-dihydro-2H-naphthalen-1-one O-methyl-oxime as a 19:1 mixture of geometric isomers; MS: (ESI) m/z 300.0 (M+H)$^+$; $^1$H NMR (400 MHz, MeOD) of Major Isomer: δ ppm 0.96 (s, 3 H), 1.09 (s, 3 H), 2.71 (d, J=17.9 Hz, 1 H), 2.86 (d, J=17.9 Hz, 1 H), 4.06 (s, 3 H), 4.74 (d, J=13.9 Hz, 1 H), 4.78 (d, J=13.9 Hz, 1 H), 5.46 (s, 1 H), 6.99 (s, 1 H), 7.14-7.16 (m, 1 H), 7.22 (s, 1 H), 7.34-7.40 (m, 2 H), 8.11-8.15 (m, 1 H).

Example 36 a) 3-{7-Methoxy-4-[(E)-methoxyimino]-2,2-dimethyl-1,2,3,4-tetrahydro-naphthalen-1-yl}-3H-imidazole-4-carboxylic acid isopropyl ester

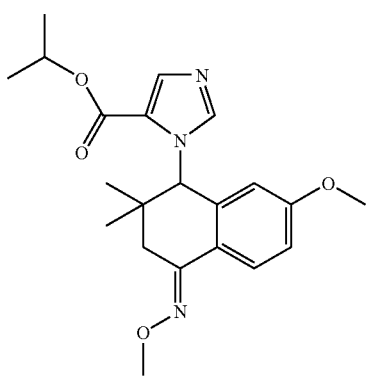 [SMILES: CO/N=C1\CC(C)(C)C(n2cncc2C(=O)OC(C)C)c2cc(OC)ccc21]

To a solution of 3-(7-methoxy-2,2-dimethyl-4-oxo-1,2,3,4-tetrahydro-naphthalen-1-yl)-3H-imidazole-4-carboxylic acid isopropyl ester, which can be prepared as described in Example 14, (0.053 g, 0.147 mmol) and methoxyamine hydrochloride (0.038 g, 0.442 mmol) in isopropanol (1 mL) is added pyridine (0.118 g, 1.472 mmol). The mixture is heated to 50° C. and after 2 hours, is diluted with ethyl acetate, and washed twice with 1M aqueous sodium bisulfate, water, and brine. The organic phase is dried over MgSO$_4$, filtered and concentrated. The resulting residue is purified by silica gel flash chromatography (elution with heptane-ethyl acetate, 4:1 to 7:3) to give 3-{7-methoxy-4-[(E)-methoxyimino]-2,2-dimethyl-1,2,3,4-tetrahydro-naphthalen-1-yl}-3H-imidazole-4-carboxylic acid isopropyl ester; MS: (ESI) m/z 386.0 (M+H)$^+$. The HCl salt of the title compound can be prepared by dissolution in diethyl ether followed by treatment with an excess of 1N HCl in diethyl ether. The resulting heterogeneous solution is concentrated to furnish the HCl salt of 3-{7-Methoxy-4-[(E)-methoxyimino]-2,2-dimethyl-1,2,3,4-tetrahydro-naphthalen-1-yl}-3H-imidazole-4-carboxylic acid isopropyl ester; $^1$H NMR (400 MHz, MeOD) δ ppm 0.96 (s, 3 H), 1.12 (s, 3 H), 1.47 (d, J=6.1 Hz, 3 H), 1.49 (d, J=6.3 Hz, 3 H), 2.43 (d, J=17.9 Hz, 1 H), 3.01 (d, J=17.9 Hz, 1 H), 3.82 (s, 3 H), 4.04 (s, 3 H), 5.40 (sept, J=6.3 Hz, 1 H), 6.65 (s, 1 H), 6.79 (d, J=2.5 Hz, 1 H), 7.09 (dd, J=9.1, 2.5 Hz, 1 H), 8.16 (d, J=9.1 Hz, 1 H), 8.30 (s, 1 H), 8.53 (s, 1 H).

b) (R)- and (S)-3-{7-Methoxy-4-[(E)-methoxyimino]-2,2-dimethyl-1,2,3,4-tetrahydro-naphthalen-1-yl}-3H-imidazole-4-carboxylic acid isopropyl ester Resolution of the enantiomers of the title compound is achieved by chiral HPLC using the ChiralPak IA column with an heptane-ethanol 9:1 mobile phase to give (R)-3-{7-Methoxy-4-[(E)-methoxyimino]-2,2-dimethyl-1,2,3,4-tetrahydro-naphthalen-1-yl}-3H-imidazole-4-carboxylic acid isopropyl ester (t$_r$=6.9 min) and (S)-3-{7-Methoxy-4-[(E)-methoxyimino]-2,2-dimethyl-1,2,3,4-tetrahydro-naphthalen-1-yl}-3H-imidazole-4-carboxylic acid isopropyl ester (t$_r$=8.7 min).

Example 37 a) (1R)— or (1S)-3-(trans-4-Hydroxy-2,2-dimethyl-1,2,3,4-tetrahydro-naphthalen-r-1-yl)-3H-imidazole-4-carboxylic acid methyl ester and

(1R)— or (1S)-3-(cis-4-Hydroxy-2,2-dimethyl-1,2,3,4-tetrahydro-naphthalen-r-1-yl)-3H-imidazole-4-carboxylic acid methyl ester

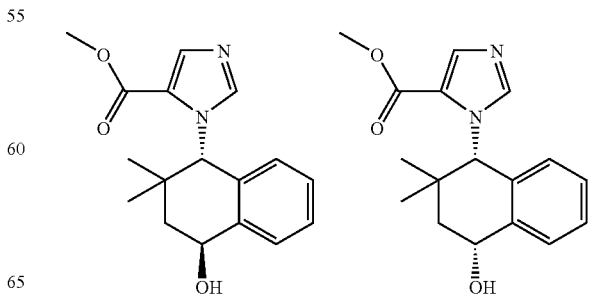

Both cis- and trans-(1R)— or (1S)-3-(4-hydroxy-2,2-dimethyl-1,2,3,4-tetrahydro-naphthalen-r-1-yl)-3H-imidazole-4-carboxylic acid methyl ester can be isolated from the mixture resulting from using the following procedure. To a solution of (R)-3-(2,2-dimethyl-4-oxo-1,2,3,4-tetrahydro-naphthalen-1-yl)-3H-imidazole-4-carboxylic acid methyl ester (0.130 g, 0.431 mmol), which can be prepared as described in Example 13, in methanol (4 mL) at 0° C. is added $NaBH_4$ (0.025 g, 0.647 mmol). After 10 min, aqueous buffer pH 7 is added and the mixture is extracted with dichloromethane. The organic phase is dried over magnesium sulfate and filtered through a cotton plug to give a residue, which is purified by silica gel flash chromatography (dichloromethane-methanol, 99:1 to 49:1) to give (1R)-3-(t-4-hydroxy-2,2-dimethyl-1,2,3,4-tetrahydro-naphthalen-r-1-yl)-3H-imidazole-4-carboxylic acid methyl ester; MS: (ESI) m/z 301.0 (M+H)$^+$; $^1$H NMR (400 MHz, MeOD) δ ppm 0.95 (s, 3 H), 1.09 (s, 3 H), 1.87 (dd, J=13.5, 8.7 Hz, 1 H), 2.19 (dd, J=13.5, 5.9 Hz, 1 H), 3.94 (s, 3 H), 5.01 (dd, J=8.7, 5.9 Hz, 1 H), 6.63 (s, 1 H), 6.70 (d, J=7.6 Hz, 1 H), 7.26 (t, J=7.6 Hz, 1 H), 7.39 (t, J=7.6 Hz, 1 H), 7.55 (s, 1 H), 7.69 (d, J=7.6 Hz, 1 H), 7.83 (d, J=1.0 Hz, 1 H); and (1R)-3-(c-4-hydroxy-2,2-dimethyl-1,2,3,4-tetrahydro-naphthalen-r-1-yl)-3H-imidazole-4-carboxylic acid methyl ester; MS: (ESI) m/z 301.0 (M+H)$^+$; $^1$H NMR (400 MHz, MeOD) δ ppm 0.77 (s, 3 H), 1.18 (s, 3 H), 1.82 (dd, J=13.9, 10.4 Hz, 1 H), 1.95 (dd, J=13.9, 6.8 Hz, 1 H), 3.97 (s, 3 H), 6.32 (s, 1 H), 7.08 (d, J=7.6 Hz, 1 H), 7.30 (t, J=7.6 Hz, 1 H), 7.44 (t, J=7.6 Hz, 1 H), 7.49 (s, 1 H), 7.75 (s, 1 H), 7.78 (d, J=7.6 Hz, 1 H). The respective enantiomers (1S)-3-(t-4-hydroxy-2,2-dimethyl-1,2,3,4-tetrahydro-naphthalen-r-1-yl)-3H-imidazole-4-carboxylic acid methyl ester and (1S)-3-(c-4-hydroxy-2,2-dimethyl-1,2,3,4-tetrahydro-naphthalen-r-1-yl)-3H-imidazole-4-carboxylic acid methyl ester can be obtained from (S)-3-(2,2-dimethyl-4-oxo-1,2,3,4-tetrahydro-naphthalen-1-yl)-3H-imidazole-4-carboxylic acid methyl ester.

The Following Compounds can be Prepared in a Similar Fashion as Example 37 cis- and trans-3-(3-Ethoxy-2,2-dimethyl-indan-1-yl)-3H-imidazole-4-carboxylic acid methyl ester

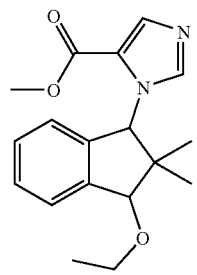

This compound can be prepared in a similar fashion to Example 37, when 3-(2,2-dimethyl-3-oxo-indan-1-yl)-3H-imidazole-4-carboxylic acid methyl ester, which can be prepared as described in Example 20, is employed in place of 3-(2,2-dimethyl-4-oxo-1,2,3,4-tetrahydro-naphthalen-1-yl)-3H-imidazole-4-carboxylic acid methyl ester. In addition the resulting secondary hydroxyl can be alkylated via deprotonation with NaH and treatment with iodoethane to furnish an isomeric mixture of cis- and trans-3-(3-ethoxy-2,2-dimethyl-indan-1-yl)-3H-imidazole-4-carboxylic acid methyl ester.

~4.5:1 isomeric mixture. MS: (ESI) m/z 315.12 (M+H)$^+$. Major diastereomer: $^1$H NMR (400 MHz, CDCl$_3$) of the free base: δ ppm 0.80 (s, 3 H), 1.16-1.24 (m, 6 H), 3.58-3.67 (m, 1 H), 3.71-3.81 (m, 1 H), 3.91 (s, 3 H), 4.24 (s, 1 H), 6.20 (s, 1 H), 7.18-7.52 (m, 5 H), 7.77 (d, J=1.0 Hz, 1 H); Minor diastereomer: $^1$H NMR (400 MHz, CDCl$_3$) of the free base: δ ppm 0.81 (s, 3 H), 1.16-1.23 (m, 6 H), 3.58-3.67 (m, 1 H), 3.72-3.80 (m, 1 H), 3.92 (s, 3 H), 4.58 (s, 1 H), 6.38 (s, 1 H), 7.04 (s, 1 H), 7.19-7.51 (m, 4 H), 7.80 (d, J=1.0 Hz, 1 H).

Example 38 a) 3-((1S,4R)-4-Hydroxy-2,2,4-trimethyl-1,2,3,4-tetrahydro-naphthalen-1-yl)-3H-imidazole-4-carboxylic acid methyl ester AND 3-((1R,4R)-4-Hydroxy-2,2,4-trimethyl-1,2,3,4-tetrahydro-naphthalen-1-yl)-3H-imidazole-4-carboxylic acid methyl ester

OR 3-((1S,4S)-4-Hydroxy-2,2,4-trimethyl-1,2,3,4-tetrahydro-naphthalen-1-yl)-3H-imidazole-4-carboxylic acid methyl ester AND 3-((1R,4S)-4-Hydroxy-2,2,4-trimethyl-1,2,3,4-tetrahydro-naphthalen-1-yl)-3H-imidazole-4-carboxylic acid methyl ester

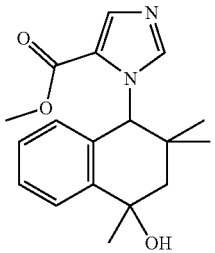

To a solution of 3-(2,2-dimethyl-4-oxo-1,2,3,4-tetrahydro-naphthalen-1-yl)-3H-imidazole-4-carboxylic acid methyl ester, which can be prepared as described in Example 13, (985 mg, 3.31 mmol) in toluene (35 mL) at −78° C. is added a 2.0 M solution of trimethyl aluminum in toluene (3.3 mL, 6.6 mmol) followed by a 1.0 M solution of dimethyl zinc in heptane (6.6 mL, 6.6 mmol). The reaction is allowed to warm to room temperature and stirred for approximately 48 hours. The reaction is then quenched with saturated aqueous NH$_4$Cl, and diluted with saturated aqueous NaHCO$_3$. The reaction mixture is then extracted with dichloromethane. The organic extract is dried with Na$_2$SO$_4$, filtered, and concentrated. The resulting residue is purified by silica gel flash chromatography (diethylamine-methanol-dichloromethane, 1:2:97) to furnish 3-(4-hydroxy-2,2,4-trimethyl-1,2,3,4-tetrahydro-naphthalen-1-yl)-3H-imidazole-4-carboxylic acid methyl ester as a single diastereomer; MS: (ESI) m/z 315 (M+H)$^+$; $^1$H NMR (400 MHz, CDCl$_3$) δ ppm 0.97 (s, 3 H), 1.04 (s, 3 H), 1.59 (br. s., 1 H), 1.65 (s, 3 H), 1.95-2.18 (m, 2 H), 3.90 (s, 3 H), 6.44 (s, 1 H), 6.76 (d, J=7.8 Hz, 1 H), 7.16-7.25 (m, 1 H), 7.37 (t, J=7.6 Hz, 1 H), 7.46 (s, 1 H), 7.66 (d, J=7.8 Hz, 1 H), 7.83 (s, 1 H);

Example 39 a) cis- AND trans-3-(4-Benzylamino-2,2-dimethyl-1,2,3,4-tetrahydro-naphthalen-1-yl)-3H-imidazole-4-carboxylic acid methyl ester The resolution of the enantiomers of the title compound is achieved by chiral HPLC using a ChiralPak IA column with 1:1 hexanes:ethanol to give $t_r$=14.3 min and $t_r$=17.9 min.

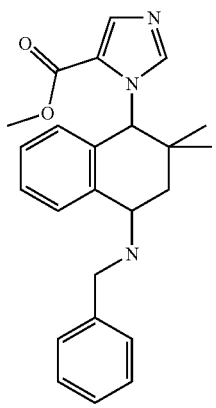

To a solution of 3-(2,2-dimethyl-4-oxo-1,2,3,4-tetrahydro-naphthalen-1-yl)-3H-imidazole-4-carboxylic acid methyl ester, which can be prepared as described in Example 13, (400 mg, 1.34 mmol) in ethanol (10 mL) at 0° C. is added benzylamine (0.22 mL, 2.01 mmol) followed by titanium (IV) isopropoxide (0.70 mL, 2.38 mmol). The reaction mixture is permitted to warm to room temperature and stirred for 15 hours. The reaction mixture is then heated to 60° C. for 1.5 hours, cooled to room temperature and charged with sodium triacetoxyborohydride (500 mg, 2.36 mmol). The reaction is permitted to stir for approximately 48 hours, at which time sodium borohydride (200 mg, 5.28 mmol) is added in two portions and the reaction is heated at 60° C. for 3 hours. The reaction is cooled to room temperature and quenched with saturated aqueous NaHCO$_3$, diluted with methanol, filtered, and concentrated to remove the organic solvents. The resulting mixture is then extracted with ethyl acetate. The organic extract is dried with Na$_2$SO$_4$, filtered, and concentrated. The resulting residue is purified by silica gel flash chromatography (methanol-dichloromethane, 0:1 to 1:9) and further purified by semi-preparative reverse phase HPLC (30 to 100% acetonitrile/water w/0.1% NH$_4$OH) to furnish cis-3-(2,2-dimethyl-4-phenylamino-1,2,3,4-tetrahydro-naphthalen-1-yl)-3H-imidazole-4-carboxylic acid methyl ester; HRMS: (ESI) m/z 390.2191 [(M+H)$^+$; calcd for C$_{24}$H$_{28}$N$_3$O$_2$: 390.2182]; $^1$H NMR (400 MHz, CDCl$_3$) δ ppm 0.79 (s, 3 H), 1.08 (s, 3 H), 1.77-2.01 (m, 2 H), 3.87-4.11 (m, 3 H), 3.92 (s, 3 H), 6.23 (s, 1 H), 7.08 (d, J=7.07 Hz, 1 H), 7.20 (t, J=7.45 Hz, 1 H), 7.25-7.42 (m, 6 H), 7.45-7.55 (m, 2 H), 7.77 (d, J=1.0 Hz, 1 H), 7.81-7.89 (m, 1 H); and trans-3-(2,2-dimethyl-4-phenylamino-1,2,3,4-tetrahydro-naphthalen-1-yl)-3H-imidazole-4-carboxylic acid methyl ester; HRMS: (ESI) m/z 390.2191 [(M+H)$^+$; calcd for C$_{24}$H$_{28}$N$_3$O$_2$: 390.2182]; $^1$H NMR (400 MHz, CDCl$_3$) δ ppm 0.93 (s, 3 H), 1.06 (s, 3 H), 1.86 (dd, J=13.3, 10.2 Hz, 1 H), 2.20 (dd, J=13.4, 5.8 Hz, 1 H), 3.82-3.99 (m, 2 H), 3.89 (s, 3 H), 4.09-4.18 (m, 1 H), 6.56-6.65 (m, 2 H), 7.15 (t, J=7.5 Hz, 1 H), 7.23-7.40 (m, 6 H), 7.41-7.48 (m, 2 H), 7.79 (d, J=7.6 Hz, 1 H), 7.85 (s, 1 H). The HCl salt of the title compounds are prepared by dissolving the compounds separately in diethyl ether followed by treatment with an excess of 1N HCl in diethyl ether. The resulting heterogeneous solutions are concentrated to furnish the HCl salts of cis- and trans-3-(2,2-dimethyl-4-phenylamino-1,2,3,4-tetrahydro-naphthalen-1-yl)-3H-imidazole-4-carboxylic acid methyl ester.

b) 3-((1S,4S)-4-Benzylamino-2,2-dimethyl-1,2,3,4-tetrahydro-naphthalen-1-yl)-3H-imidazole-4-carboxylic acid methyl ester and 3-((1R,4R)-4-Benzylamino-2,2-dimethyl-1,2,3,4-tetrahydro-naphthalen-1-yl)-3H-imidazole-4-carboxylic acid methyl ester The resolution of the enantiomers the trans isomer (LDA268) of the title compound is achieved by chiral HPLC using a ChiralPak IA column with 9:1 heptane:ethanol to give $t_r$=18 min and $t_r$=28 min.

The Following Compounds can be Prepared in a Similar Fashion as Example 39 cis- OR trans-3-(2,2-Dimethyl-4-propylamino-1,2,3,4-tetrahydro-naphthalen-1-yl)-3H-imidazole-4-carboxylic acid methyl ester

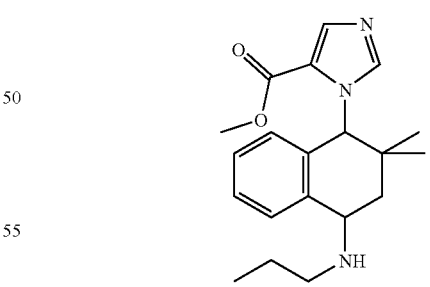

$^1$H NMR (400 MHz, CDCl$_3$) of the free base: δ ppm 0.95 (s, 3 H), 0.98 (t, J=7.5 Hz, 3 H), 1.03 (s, 3 H), 1.47-1.67 (m, 2 H), 1.79 (dd, J=13.4, 10.4 Hz, 1 H), 2.14 (dd, J=13.5, 5.68 Hz, 1 H), 2.57-2.75 (m, 2 H), 3.88 (s, 3 H), 4.04-4.15 (m, 1 H), 6.54-6.63 (m, 2 H), 7.13 (t, J=7.5 Hz, 1 H), 7.25-7.33 (m, 1 H), 7.39 (br. s., 1 H), 7.71 (d, J=7.8 Hz, 1 H), 7.86 (br. s., 1 H); HRMS: (ESI) m/z 342.2184 [(M+H)⁺; calcd for $C_{24}H_{28}N_3O_2$: 342.2182].

cis- OR trans-3-(4-Cyclohexylamino-2,2-dimethyl-1,2,3,4-tetrahydro-naphthalen-1-yl)-3H-imidazole-4-carboxylic acid methyl ester (Major Isomer)

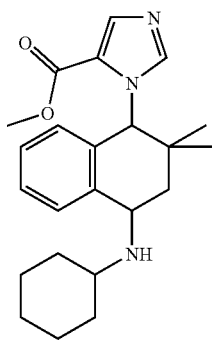

¹H NMR (400 MHz, CDCl₃) of the free base: δ ppm 0.93 (s, 3 H), 1.02 (s, 3 H), 1.15-1.42 (m, 5 H), 1.60-1.71 (m, 2 H), 1.74-1.86 (m, 3 H), 2.00-2.08 (m, 1 H), 2.16 (dd, J=13.4, 5.8 Hz, 1 H), 2.69-2.84 (m, 1 H), 3.87 (s, 3 H), 4.00-4.14 (m, 1 H), 6.51-6.64 (m, 2 H), 7.11 (t, J=7.5 Hz, 1 H), 7.22-7.32 (m, 1 H), 7.37 (br. s., 1 H), 7.73 (d, J=7.6 Hz, 1 H), 7.85 (br. s., 1 H); HRMS: (ESI) m/z 382.2476 [(M+H)⁺; calcd for $C_{23}H_{32}N_3O_2$: 382.2495].

cis- OR trans-3-(4-Cyclohexylamino-2,2-dimethyl-1,2,3,4-tetrahydro-naphthalen-1-yl)-)-3H-imidazole-4-carboxylic acid methyl ester (Minor Isomer)

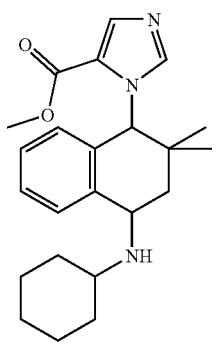

¹H NMR (400 MHz, CDCl₃) of the free base: δ ppm 0.76 (s, 3 H), 1.11 (s, 3 H), 1.21-1.42 (m, 5 H), 1.57-1.72 (m, 2 H), 1.74-2.00 (m, 4 H), 2.02-2.12 (m, 1 H), 2.72-2.87 (m, 1 H), 3.91 (s, 3 H), 3.99-4.07 (m, 1 H), 6.21 (s, 1 H), 7.04 (d, J=7.6 Hz, 1 H), 7.17 (t, J=7.5 Hz, 1 H), 7.30-7.41 (m, 2 H), 7.69-7.91 (m, 2 H); HRMS: (ESI) m/z 382.2503 [(M+H)⁺; calcd for $C_{23}H_{32}N_3O_2$: 382.2495].

Example 40 a) 3-(2,2,4-Trimethyl-1,2-dihydro-naphthalen-1-yl)-3H-imidazole-4-carboxylic acid methyl ester

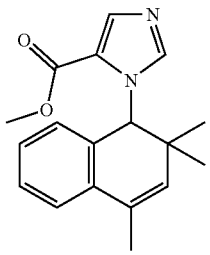

To a 1.25 M anhydrous methanol solution of HCl (3 mL) is added 3-(4-hydroxy-2,2,4-trimethyl-1,2,3,4-tetrahydro-naphthalen-1-yl)-3H-imidazole-4-carboxylic acid methyl ester, which can be prepared as described in Example 38, (85 mg, 0.27 mmol). The reaction is then heated to 50° C., and is then concentrated to dryness. The resulting residue is purified by silica gel flash chromatography (diethylamine-methanol-dichloromethane, 0.5:1:98.5) to provide 3-(2,2,4-trimethyl-1,2-dihydro-naphthalen-1-yl)-3H-imidazole-4-carboxylic acid methyl ester; MS: (ESI) m/z 297.0 (M+H)⁺; ¹H NMR (400 MHz, CDCl₃) δ ppm 0.86 (s, 3 H), 1.13 (s, 3 H), 2.15 (d, J=1.3 Hz, 3 H), 3.91 (s, 3 H), 5.56 (s, 1 H), 6.31 (s, 1 H), 7.16-7.26 (m, 2 H), 7.31-7.41 (m, 2 H), 7.43 (s, 1 H), 7.70 (s, 1 H). The HCl salt of the title compound can be prepared by dissolution in diethyl ether followed by treatment with an excess of 1N HCl in diethyl ether. The resulting heterogeneous solution is concentrated to afford the HCl salt of 3-(2, 2,4-trimethyl-1,2-dihydro-naphthalen-1-yl)-3H-imidazole-4-carboxylic acid methyl ester.

Example 41 a) (1R)- or (1S)-3-(c-4-Fluoro-2,2-dimethyl-1,2,3,4-tetrahydro-naphthalen-r-1-yl)-3H-imidazole-4-carboxylic acid methyl ester AND (1R)- or (1S)-3-(t-4-Fluoro-2,2-dimethyl-1,2,3,4-tetrahydro-naphthalen-r-1-yl)-3H-imidazole-4-carboxylic acid methyl ester AND (R)- or (S)-3-(2,2-Dimethyl-1,2-dihydro-naphthalen-1-yl)-3H-imidazole-4-carboxylic acid methyl ester

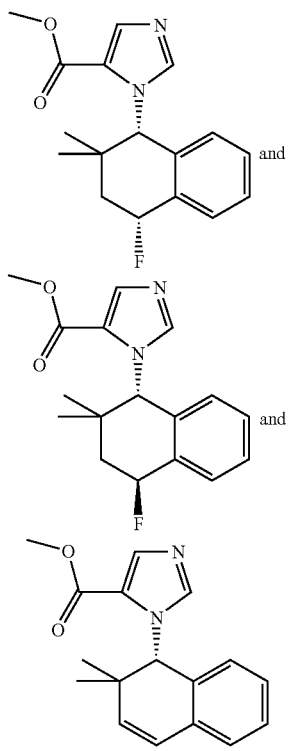

The above structured compounds can be isolated from the mixture resulting from using the following procedure. To a solution of (1R)— or (1S)-3-(t-4-hydroxy-2,2-dimethyl-1,2,3,4-tetrahydro-naphthalen-r-1-yl)-3H-imidazole-4-carboxylic acid methyl ester (0.610 g, 1.990 mmol), which can be prepared as described in Example 37, in dichloromethane (30 mL) at 0° C. under nitrogen is added DAST (1.013 g, 5.971 mmol) dropwise. After 10 minutes, the mixture is diluted with dichloromethane and washed twice with saturated aqueous sodium bicarbonate, followed by water and brine. The combined aqueous phases are back-extracted once with dichloromethane. The combined organic phases are dried over magnesium sulfate and filtered through a plug of silica gel in a sintered funnel (elution with dichloromethane then dichloromethane-methanol, 49:1). After concentration of the filtrate, the residue is purified by HPLC on a Chiralpak IA eluting with heptane-reagent alcohol 9:1, to afford. All three products can be converted to the hydrochloric salt by dissolution in diethyl ether followed by treatment with an excess of 1N HCl in diethyl ether. The resulting heterogeneous solution is concentrated to afford the respective HCl salts:

(R)- or (S)-3-(2,2-dimethyl-1,2-dihydro-naphthalen-1-yl)-3H-imidazole-4-carboxylic acid methyl ester; MS: (ESI) m/z 283.0 (M+H)$^+$; $^1$H NMR (400 MHz, MeOD) of the HCl salt: δ ppm 0.97 (s, 3 H), 1.24 (s, 3 H), 4.05 (s, 3 H), 5.88 (d, J=9.7 Hz, 1 H), 6.59 (s, 1 H), 6.75 (d, J=9.6 Hz, 1 H), 7.31-7.39 (m, 3 H), 7.44-7.49 (m, 1 H), 8.14 (s, 1 H), 8.34 (s, 1 H).

(1R)- or (1S)-3-(c-4-fluoro-2,2-dimethyl-1,2,3,4-tetrahydro-naphthalen-r-1-yl)-3H-imidazole-4-carboxylic acid methyl ester; MS: (ESI) m/z 303.0 (M+H)$^+$; $^1$H NMR (400 MHz, MeOD) of the HCl salt: δ ppm 0.97 (s, 3 H), 1.20 (s, 3 H), 2.07-2.17 (m, 1 H), 2.21-2.30 (m, 1 H), 4.05 (s, 3 H), 5.81 (dt, J=50.8, 7.1 Hz, 1 H), 6.66 (s, 1 H), 7.13 (d, J=7.6 Hz, 1 H), 7.44 (t, J=7.6 Hz, 1 H), 7.55 (t, J=7.6 Hz, 1 H), 7.72 (d, J=7.6 Hz, 1 H), 8.34 (s, 1 H), 8.57 (s, 1 H);

(1R)- or (1S)-3-(t-4-fluoro-2,2-dimethyl-1,2,3,4-tetrahydro-naphthalen-r-1-yl)-3H-imidazole-4-carboxylic acid methyl ester; MS: (ESI) m/z 303.0 (M+H)$^+$; $^1$H NMR (400 MHz, MeOD) of the HCl salt: δ ppm 0.89 (s, 3 H), 1.23 (s, 3 H), 2.05-2.31 (m, 2 H), 4.02 (s, 3 H), 5.84 (dt, J=51.0, 4.5 Hz, 1 H), 6.65 (s, 1 H), 7.13 (d, J=7.6 Hz, 1 H), 7.44 (t, J=7.6 Hz, 1 H), 7.52 (t, J=7.6 Hz, 1 H), 7.66 (d, J=7.6 Hz, 1 H), 8.11 (s, 2 H).

Example 42 a) 1-(3,3-Dimethyl-indan-1-yl)-1H-imidazole

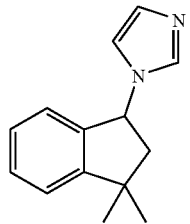 [SMILES: CC1(C)CC(n2ccnc2)c2ccccc21]

To a solution of 3,3-dimethyl-indan-1-ol (CAS#38393-92-9, 1.62 g, 1.0 mmol)] in toluene (30 mL) is added imidazole (1.36 g, 20.0 mmol) followed by tri-t-butylphosphine (2.5 mL, 10.1 mmol). The reaction is put at 0° C. and N,N,N',N'-tetramethylazodicarboxamide (1.72 g, 10 mol) is then added. The reaction is permitted to stir for 10 minutes at 0° C. and then is heated at 60° C. over night. The next morning the reaction is diluted with heptane (30 mL) and filtered. The filtrate is extracted twice with 1 N aqueous HCl. The aqueous extracts are combined, washed with ethyl acetate and then basified (pH>10) by the careful addition of 5 N aqueous NaOH. The aqueous solution is then extracted three times with dichloromethane. The combined organic extracts are dried with Na$_2$SO$_4$, filtered and concentrated. The resulting residue is purified by semi-preparative reverse phase HPLC (15 to 85% acetonitrile/water w/0.1% NH$_4$OH) to afford 1-(3, 3-dimethyl-indan-1-yl)-1H-imidazole; HRMS: (ESI) m/z 213.1397 [(M+H)+; calcd for $C_{14}H_{17}N_2$: 213.1392]; $^1$H NMR (400 MHz, CDCl$_3$) δ ppm 1.28 (s, 3 H), 1.42 (s, 3 H), 2.11 (dd, J=12.9, 8.3 Hz, 1 H), 2.57 (dd, J=12.9, 7.6 Hz, 1 H), 5.72 (t, J=8.1 Hz, 1 H), 6.86 (s, 1 H), 7.01 (d, J=8.3 Hz, 1 H), 7.09 (s, 1 H), 7.19-7.29 (m, 2 H), 7.35 (t, J=7.5 Hz, 1 H), 7.62 (s, 1 H). The HCl salt of the title compound can be prepared by dissolution in diethyl ether followed by treatment with an excess of 1N HCl in diethyl ether. The resulting heterogeneous solution is concentrated to furnish the HCl salt of 1-(3,3-dimethyl-indan-1-yl)-1H-imidazole.

Example 43 a) 3-(7-Thiophen-2-yl-1,2,3,4-tetrahydro-naphthalen-1-yl)-3H-imidazole-4-carboxylic acid isopropyl ester

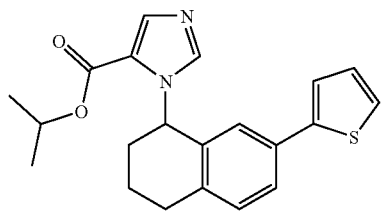 [SMILES: CC(C)OC(=O)c1cncn1C1CCCc2ccc(-c3cccs3)cc21]

A flask is charged with 3-(7-bromo-1,2,3,4-tetrahydro-naphthalen-1-yl)-3H-imidazole-4-carboxylic acid isopropyl ester (0.225 g, 0.520 mmol), which can be prepared as described in Example 5, 2-thienylboronic acid (0.145 g, 1.041 mmol), aqueous sodium carbonate (2M, 1.30 mL, 2.60 mmol) and DMF (35 mL). Tetrakis(triphenylphosphine) palladium (0.060 g, 0.052 mmol) is added and the mixture is heated to 150° C. in a sealed tube under microwave irradiation conditions for 12 minutes. The reaction is then cooled to room temperature, diluted with water and extracted with dichloromethane. The organic phase is dried over sodium sulfate, filtered, and concentrated to give a residue, which is purified by silica gel chromatography (hexanes-ethyl acetate mixtures) to give 3-[7-thiophen-2-yl-1,2,3,4-tetrahydro-naphthalen-1-yl]-3H-imidazole-4-carboxylic acid isopropyl ester. MS: (ESI) m/z 367.2 (M+H)+. The HCl salt of the title compound can be prepared by dissolution in diethyl ether followed by treatment with an excess of 1N HCl in diethyl ether. The resulting heterogeneous solution is concentrated to furnish the HCl salt of 3-[7-thiophen-2-yl-1,2,3,4-tetrahydro-naphthalen-1-yl]-3H-imidazole-4-carboxylic acid isopropyl ester; $^1$H NMR (400 MHz, MeOD) δ ppm 1.38 (d, J=6.3 Hz, 3 H), 1.41 (d, J=6.3 Hz, 3 H), 1.80-1.97 (m, 2 H), 2.22-2.34 (m, 2 H), 2.86-2.94 (m, 1 H), 3.04 (dt, J=17.2, 6.0 Hz, 1 H), 5.26 (d, J=6.3 Hz, 1 H), 6.36 (t, J=5.6 Hz, 1 H), 7.06 (dd, J=5.2, 3.7 Hz, 1 H), 7.18 (br. s, 1 H), 7.28 (dd, J=3.7, 1.1 Hz, 1 H), 7.30 (d, J=8.1 Hz, 1 H), 7.34 (dd, J=5.2, 1.1 Hz, 1 H), 7.48 (s, 1 H), 7.58 (dd, J=8.1, 2.0 Hz, 1 H), 7.77 (d, J=1.0 Hz, 1 H).

Example 44 a) 3-[7-(Pyrrolidine-1-carbonyl)-1,2,3,4-tetrahydro-naphthalen-1-yl]-3H-imidazole-4-carboxylic acid isopropyl ester AND 3-[7-(dimethylcarbamoyl)-1,2,3,4-tetrahydro-naphthalen-1-yl]-3H-imidazole-4-carboxylic acid isopropyl ester

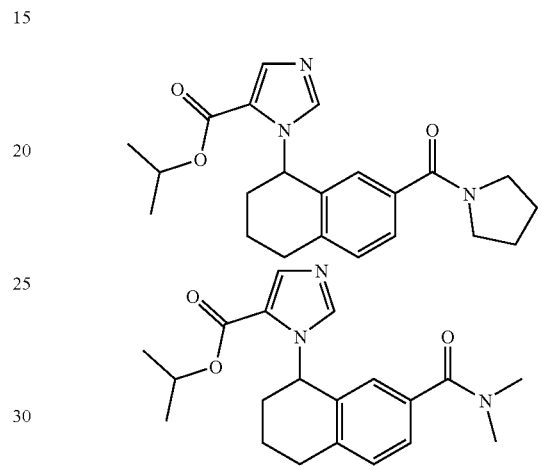

3-[7-(Pyrrolidine-1-carbonyl)-1,2,3,4-tetrahydro-naphthalen-1-yl]-3H-imidazole-4-carboxylic acid isopropyl ester and 3-[7-(dimethylcarbamoyl)-1,2,3,4-tetrahydro-naphthalen-1-yl]-3H-imidazole-4-carboxylic acid isopropyl ester can be obtained from the reaction mixture resulting from this procedure. A pressure tube fitted with a septum is charged with 3-(7-bromo-1,2,3,4-tetrahydro-naphthalen-1-yl)-3H-imidazole-4-carboxylic acid isopropyl ester, which can be prepared as described in Example 5, (0.304 g, 0.836 mmol), pyrrolidine (0.298 g, 4.184 mmol), (bis-triphenylphosphine) palladium dichloride (0.029 g, 0.418 mmol), and DMF (4 mL). Carbon monoxide is bubbled through the solution for 15 min, and then the septum is replaced with a screw cap and the mixture is heated to 100° C. overnight. The reaction is cooled to room temperature, diluted with water, and extracted with ethyl acetate. The organic phase is dried over sodium sulfate, filtered, and concentrated. The resulting residue is purified by silica gel chromatography (dichloromethane-methanol mixtures) to give 3-[7-(pyrrolidine-1-carbonyl)-1,2,3,4-tetrahydro-naphthalen-1-yl]-3H-imidazole-4-carboxylic acid isopropyl ester; MS: (ESI) m/z 382.2 (M+H)+; $^1$H NMR (400 MHz, MeOD) δ ppm 1.37 (d, J=6.3 Hz, 3 H), 1.39 (d, J=6.3 Hz, 3 H), 1.85-2.01 (m, 6 H), 2.28-2.33 (m, 2 H), 2.90-2.98 (m, 1 H), 3.09 (dt, J=17.4, 6.3 Hz, 1 H), 3.27-3.33 (m, 1 H), 3.38-3.42 (m, 1 H), 3.56 (t, J=6.9 Hz, 2 H), 5.21 (sept, J=6.3 Hz, 1 H), 6.37 (t, J=5.9 Hz, 1 H), 7.05 (br. s, 1 H), 7.36 (d, J=7.8 Hz, 1 H), 7.45 (dd, J=7.8, 1.5 Hz, 1 H), 7.56 (s, 1 H), 7.76 (s, 1 H); and 3-[7-(dimethylcarbamoyl)-1,2,3,4-tetrahydro-naphthalen-1-yl]-3H-imidazole-4-carboxylic acid isopropyl ester; MS: (ESI) m/z 356.2 (M+H)+; $^1$H NMR (400 MHz, MeOD) δ ppm 1.37 (d, J=6.3 Hz, 3 H), 1.39 (d, J=6.3 Hz, 3 H), 1.88-1.96 (m, 2 H), 2.27-2.32 (m, 2 H), 2.90-2.98 (m, 1 H), 2.94 (s, 3 H), 3.04-3.14 (m, 1 H), 3.06 (s, 3 H), 5.22 (sept, J=6.3 Hz, 1 H), 6.36 (t, J=6.1 Hz, 1 H), 6.96 (br. s., 1 H), 7.34-7.40 (m, 2 H), 7.55 (br. s., 1 H), 7.76 (br. s., 1 H).

b) (R)- and (S)-3-[7-(Pyrrolidine-1-carbonyl)-1,2,3,4-tetrahydro-naphthalen-1-yl]-3H-imidazole-4-carboxylic acid isopropyl ester Resolution of the enantiomers of the title compound is achieved by chiral HPLC using a ChiralPak IA column with 100% acetonitrile to give two isomers with $t_r$=17.0 min and $t_r$=22.5 min.

Example 45 a) 3-(7-Amino-1,2,3,4-tetrahydro-naphthalen-1-yl)-3H-imidazole-4-carboxylic acid isopropyl ester

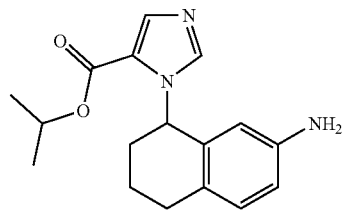 [SMILES: CC(C)OC(=O)c1cncn1C1CCCc2ccc(N)cc21]

To a solution of 3-(7-nitro-1,2,3,4-tetrahydro-naphthalen-1-yl)-3H-imidazole-4-carboxylic acid isopropyl ester, which can be prepared as described in Example 5, (3.24 g, 9.84 mmol) in ethanol (125 mL) is added palladium on carbon (10% wt., 0.65 g, 0.61 mmol). The flask is flushed with hydrogen and stirred under balloon pressure at room temperature overnight. The catalyst is then filtered through Celite®. The Celite® cake is washed with methanol and the combined filtrate is concentrated to afford 3-(7-acetylamino-1,2,3,4-tetrahydro-naphthalen-1-yl)-3H-imidazole-4-carboxylic acid isopropyl ester; $^1$H NMR (400 MHz, CDCl$_3$) δ ppm 1.37 (d, J=6.3 Hz, 3 H), 1.38 (d, J=6.3 Hz, 3 H), 1.62-1.83 (m, 2 H), 2.01-2.08 (m, 1 H), 2.13-2.21 (m, 1 H), 2.67-2.84 (m, 2 H), 5.22 (sept, J=6.3 Hz, 1 H), 6.17 (t, J=5.1 Hz, 1 H), 6.31 (d, J=2.5 Hz, 1 H), 6.62 (dd, J=8.2, 2.5 Hz, 1 H), 6.98 (d, J=8.2 Hz, 1 H), 7.21 (s, 1 H), 7.77 (s, 1 H).

b) 3-(7-Acetylamino-1,2,3,4-tetrahydro-naphthalen-1-yl)-3H-imidazole-4-carboxylic acid isopropyl ester

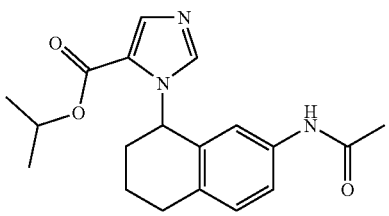 [SMILES: CC(=O)Nc1ccc2c(c1)C(n1cncc1C(=O)OC(C)C)CCC2]

To a solution of 3-(7-amino-1,2,3,4-tetrahydro-naphthalen-1-yl)-3H-imidazole-4-carboxylic acid isopropyl ester (0.180 g, 0.602 mmol) and pyridine (0.052 g, 0.662 mmol) in dichloromethane (2 mL) is added acetyl chloride (0.052 g, 0.662 mmol) at 0° C. and the reaction is stirred for 2.5 hours. The solution is then washed with 10% aqueous HCl and water and the combined aqueous phases are extracted with ethyl acetate. The combined organic phases are dried over sodium sulfate, filtered, and concentrated to give a residue, which is purified by silica gel chromatography (dichloromethane-methanol mixtures) to give 3-(7-acetylamino-1,2,3,4-tetrahydro-naphthalen-1-yl)-3H-imidazole-4-carboxylic acid isopropyl ester; MS: (ESI) m/z 342.2 (M+H)$^+$; $^1$H NMR (400 MHz, MeOD) δ ppm 1.39 (d, J=6.3 Hz, 3 H), 1.40 (d, J=6.3 Hz, 3 H), 1.78-1.92 (m, 2 H), 2.08 (s, 3 H), 2.16-2.31 (m, 2 H), 2.81-2.89 (m, 1 H), 2.98 (dt, J=16.9, 6.1 Hz, 1 H), 5.25 (sept, J=6.3 Hz, 1 H), 6.32 (t, J=5.4 Hz, 1 H), 7.17 (br. s, 1 H), 7.22 (d, J=8.3 Hz, 1 H), 7.43 (s, 1 H), 7.50 (dd, J=8.3, 2.1 Hz, 1 H), 7.74 (d, J=1.0 Hz, 1 H).

Example 46 a) 3-(7-Methanesulfonylamino-1,2,3,4-tetrahydro-naphthalen-1-yl)-3H-imidazole-4-carboxylic acid isopropyl ester

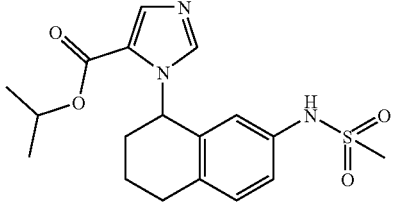 [SMILES: CC(C)OC(=O)c1cncn1C1CCCc2ccc(NS(C)(=O)=O)cc21]

To a solution of 3-(7-amino-1,2,3,4-tetrahydro-naphthalen-1-yl)-3H-imidazole-4-carboxylic acid isopropyl ester, which can be prepared as described as in Example 45, (0.408 g, 1.36 mmol) and pyridine (0.162 g, 2.04 mmol) in dichloromethane (4 mL) at 0° C. is added methanesulfonyl chloride (0.168 g, 1.47 mmol) and the reaction is stirred for 2.5 hours. The solution is then washed with 10% aqueous HCl and water and the combined aqueous phases are extracted with ethyl acetate. The combined organic phases are dried over sodium sulfate, filtered and concentrated to give a residue, which is purified by silica gel chromatography (dichloromethane-methanol mixtures) to give 3-(7-methanesulfonylamino-1,2,3,4-tetrahydro-naphthalen-1-yl)-3H-imidazole-4-carboxylic acid isopropyl ester; MS: (ESI) m/z 378.2 (M+H)$^+$; $^1$H NMR (400 MHz, MeOD) δ ppm 1.38 (d, J=6.3 Hz, 3 H), 1.40 (d, J=6.3 Hz, 3 H), 1.84-1.93 (m, 2 H), 2.19-2.33 (m, 2 H), 2.87 (dt, J=16.9, 6.6 Hz, 1 H), 2.88 (s, 3 H), 3.01 (dt, J=16.9, 6.3 Hz, 1 H), 5.24 (sept, J=6.3 Hz, 1 H), 6.32 (t, J=6.1 Hz, 1 H), 6.81 (d, J=2.0 Hz, 1 H), 7.21 (dd, J=8.3, 2.0 Hz, 1 H), 7.26 (d, J=8.3 Hz, 1 H), 7.51 (s, 1 H), 7.75 (d, J=1.0 Hz, 1 H).

Example 47 a) 3-(7-Methanesulfonyl-methyl-amino-1,2,3,4-tetrahydro-naphthalen-1-yl)-3H-imidazole-4-carboxylic acid isopropyl ester

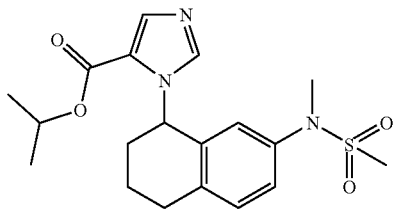 [SMILES: CC(C)OC(=O)c1cncn1C1CCCc2ccc(N(C)S(C)(=O)=O)cc21]

To a suspension of 3-(7-methanesulfonylamino-1,2,3,4-tetrahydro-naphthalen-1-yl)-3H-imidazole-4-carboxylic acid isopropyl ester, which can be prepared as described in Example 46, (0.145 g, 0.384 mmol) and potassium carbonate (0.106 g, 0.769 mmol) in DMF (5 mL) at 0° C. is added methyl iodide (0.082 g, 0.576 mmol) and the reaction is stirred for 2 hours. After dilution, the solution is washed with 10% aqueous HCl and water and the combined aqueous phases are extracted with ethyl acetate. The combined organic phases are dried over sodium sulfate, filtered, and concentrated to give a residue, which is purified by silica gel chromatography (dichloromethane-methanol mixtures) to give 3-(7-methanesulfonyl-methyl-amino-1,2,3,4-tetrahydro-naphthalen-1-yl)-3H-imidazole-4-carboxylic acid isopropyl ester; MS: (ESI) m/z 392.2 (M+H)$^+$; $^1$H NMR (400 MHz, MeOD) δ ppm 1.38 (d, J=6.3 Hz, 3 H), 1.39 (d, J=6.3 Hz, 3 H), 1.79-1.96 (m, 2 H), 2.20-2.33 (m, 2 H), 2.83 (s, 3 H), 2.86-2.94 (m, 1 H), 3.00-3.08 (m, 1 H), 3.24 (s, 3 H), 5.22 (sept, J=6.3 Hz, 1 H), 6.33 (t, J=5.9 Hz, 1 H), 7.00 (d, J=2.3 Hz, 1 H), 7.32 (d, J=8.3 Hz, 1 H), 7.37 (dd, J=8.3, 2.3 Hz, 1 H), 7.47 (s, 1 H), 7.75 (d, J=1.3 Hz, 1 H).

Example 48 a) Trifluoro-methanesulfonic acid 5-oxo-5,6,7,8-tetrahydro-naphthalen-2-yl ester

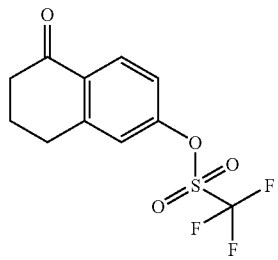 [SMILES: O=C1CCCc2cc(OS(=O)(=O)C(F)(F)F)ccc21]

To a solution of 6-hydroxy-3,4-dihydro-2H-naphthalen-1-one (CAS#3470-50-6, 0.10 g, 0.62 mmol) in pyridine (3 mL) is added trifluoromethane sulfonic anhydride (0.26 g, 0.92 mmol) and the solution is stirred for 1 hour. After dilution with dichloromethane, the solution is washed with water and 1M aqueous HCl, dried and concentrated to give trifluoro-methanesulfonic acid 5-oxo-5,6,7,8-tetrahydro-naphthalen-2-yl ester; $^1$H NMR (400 MHz, CDCl$_3$) δ ppm 2.15-2.24 (m, 2 H), 2.67-2.73 (m, 2 H), 3.03 (t, J=6.1 Hz, 2 H), 7.20-7.23 (m, 2 H), 8.14 (d, J=8.3 Hz, 1 H).

b) 3-(6-Trifluoromethanesulfonyloxy-1,2,3,4-tetrahydro-naphthalen-1-yl)-3H-imidazole-4-carboxylic acid isopropyl ester

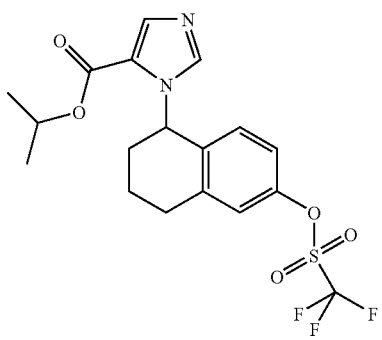 [SMILES: CC(C)OC(=O)c1cncn1C1CCCc2cc(OS(=O)(=O)C(F)(F)F)ccc21]

To a solution of trifluoro-methanesulfonic acid 5-oxo-5,6,7,8-tetrahydro-naphthalen-2-yl ester (8.63 g, 0.027 mol) in methanol (75 mL) at 0° C. is added sodium borohydride (2.84 g, 0.075 mol) in one portion. The cooling bath is removed and after 1.5 hours and the mixture is poured into water (75 mL). The volatile organics are then removed in vacuo. The resulting mixture is extracted with dichloromethane, dried over magnesium sulfate, filtered, and concentrated to afford trifluoro-methanesulfonic acid 5-oxo-5,6,7,8-tetrahydro-naphthalen-2-yl ester, which is used in the next step without further purification.

To a suspension of trifluoro-methanesulfonic acid 5-oxo-5,6,7,8-tetrahydro-naphthalen-2-yl ester (5.0 g, 0.016 mol) and isopropyl 4-imidazolecarboxylate, which can be prepared as described in Example 1 (1.72 g, 0.011 mol) in THF (100 mL) at 0° C. is added triphenylphosphine (4.20 g, 0.016 mol) and dimethyl azodicarboxylate (40% wt. in, toluene, 5.85 g, 0.016 mol). After 1 hour, the mixture is diluted with ethyl acetate and washed with water. The organic phase is dried with Na$_2$SO$_4$, filtered, and concentrated to give a residue, which is purified by silica gel chromatography (elution with hexanes-ethyl acetate mixtures) to give 3-(6-trifluoromethanesulfonyloxy-1,2,3,4-tetrahydro-naphthalen-1-yl)-3H-imidazole-4-carboxylic acid isopropyl ester; $^1$H NMR (400 MHz, MeOD) δ ppm 1.37 (t, J=6.8 Hz, 6 H), 1.88-1.97 (m, 2 H), 2.27-2.34 (m, 2 H), 2.96 (dd, J=17.4, 6.3 Hz, 1 H), 3.11 (dd, J=17.4, 6.6 Hz, 1 H), 5.22 (t, J=6.8 Hz, 1 H), 6.36 (t, J=6.2 Hz, 1 H), 7.06 (d, J=8.8 Hz, 1 H), 7.19 (dd, J=8.8, 2.5 Hz, 1 H), 7.29 (d, J=2.5 Hz, 1 H), 7.58 (s, 1 H), 7.76 (d, J=1.0 Hz, 1 H).

c) 3-[6-(4-Fluoro-phenyl)-1,2,3,4-tetrahydro-naphthalen-1-yl]-3H-imidazole-4-carboxylic acid isopropyl ester

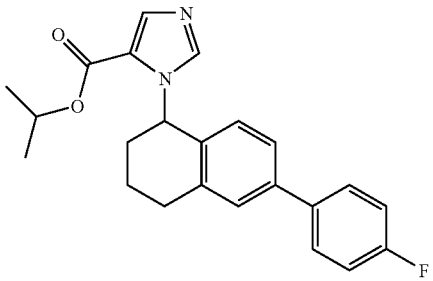 [SMILES: CC(C)OC(=O)c1cncn1C1CCCc2cc(-c3ccc(F)cc3)ccc21]

A flask is charged with 3-(6-trifluoromethanesulfonyloxy-1,2,3,4-tetrahydro-naphthalen-1-yl)-3H-imidazole-4-carboxylic acid isopropyl ester (0.225 g, 0.520 mmol), 4-fluorophenylboronic acid (0.145 g, 1.041 mmol), aqueous sodium carbonate (2M, 1.30 mL, 2.60 mmol) and DMF (35 mL). Tetrakis(triphenylphosphine) palladium (0.060 g, 0.052 mmol) is added and the mixture is heated to 150° C. in a sealed tube under microwave irradiation conditions for 12 minutes. The reaction is cooled to room temperature, diluted with water and extracted with dichloromethane. The organic phase is dried with Na$_2$SO$_4$, filtered, and concentrated to give a residue, which is purified by silica gel chromatography (hexanes-ethyl acetate mixtures) to give 3-[6-(4-fluoro-phenyl)-1,2,3,4-tetrahydro-naphthalen-1-yl]-3H-imidazole-4-carboxylic acid isopropyl ester. MS: (ESI) m/z 379.2 (M+H)$^+$. The HCl salt of the title compound can be prepared by dissolution in diethyl ether followed by treatment with an excess of 1N HCl in diethyl ether. The resulting heterogeneous solution is concentrated to furnish the HCl salt of 3-[6-(4-fluoro-phenyl)-1,2,3,4-tetrahydro-naphthalen-1-yl]-3H-imidazole-4-carboxylic acid isopropyl ester; $^1$H NMR (400 MHz, MeOD) δ ppm 1.45 (d, J=6.3 Hz, 3 H), 1.47 (d, J=6.3 Hz, 3 H), 1.75-1.86 (m, 1 H), 1.93-2.02 (m, 1 H), 2.31-2.47 (m, 2 H), 2.99 (ddd, J=17.0, 9.3, 5.6 Hz, 1 H), 3.13 (dt, J=17.0, 5.3 Hz, 1 H), 5.36 (sept, J=6.3 Hz, 1 H), 6.61 (t, J=5.1 Hz, 1 H), 7.19-7.25 (m, 3 H), 7.51 (dd, J=8.1, 2.0 Hz, 1 H), 7.57 (s, 1 H), 7.66-7.72 (m, 2 H), 8.34 (d, J=1.5 Hz, 1 H), 8.65 (d, J=1.3 Hz, 1 H).

The Following Compound can be Prepared in a Similar Fashion as Example 48

3-(6-Thiophen-2-yl-1,2,3,4-tetrahydro-naphthalen-1-yl)-3H-imidazole-4-carboxylic acid isopropyl ester

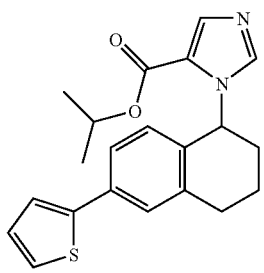 [SMILES: CC(C)OC(=O)c1cncn1C1CCCc2cc(-c3cccs3)ccc21]

$^1$H NMR (400 MHz, MeOD) of the HCl salt: δ ppm 1.44 (d, J=6.3 Hz, 3 H), 1.46 (d, J=6.3 Hz, 3 H), 1.72-1.80 (m, 1 H), 1.92-2.00 (m, 1 H), 2.28-2.41 (m, 2 H), 2.96 (ddd, J=17.3, 9.1, 5.3 Hz, 1 H), 3.09 (dt, J=17.3, 5.3 Hz, 1 H), 5.35 (sept, J=6.3 Hz, 1 H), 6.57 (t, J=5.1 Hz, 1 H), 7.15 (dd, J=5.2, 3.7 Hz, 1 H), 7.18 (d, J=8.2 Hz, 1 H), 7.18 (dd, J=5.2, 1.1 Hz, 1 H), 7.48 (dd, J=3.7, 1.1 Hz, 1 H), 7.56 (dd, J=8.2, 2.0 Hz, 1 H), 7.62 (br. s, 1 H), 8.33 (d, J=1.5 Hz, 1 H), 8.64 (d, J=1.3 Hz, 1 H); MS: (ESI) m/z 367.2 (M+H)$^+$.

Example 49 a) 3-(6-Cyclopropyl-1,2,3,4-tetrahydro-naphthalen-1-yl)-3H-imidazole-4-carboxylic acid isopropyl ester

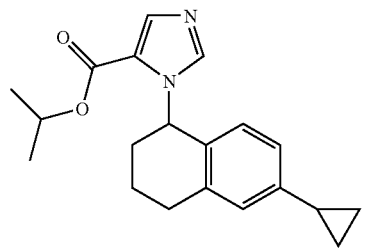 [SMILES: CC(C)OC(=O)c1cncn1C1CCCc2cc(C3CC3)ccc21]

A flask is charged with 3-(6-trifluoromethanesulfonyloxy-1,2,3,4-tetrahydro-naphthalen-1-yl)-3H-imidazole-4-carboxylic acid isopropyl ester (0.183 g, 0.426 mmol), which can be prepared as described in Example 48, cyclopropylboronic acid (0.091 g, 1.059 mmol), potassium fluoride (0.081 g, 1.39 mmol), sodium bromide (0.043 g, 0.423 mmol) and toluene (5 mL). Tetrakis(triphenylphosphine) palladium (0.015 g, 0.013 mmol) is added and the mixture is heated to 90° C. overnight. The reaction is cooled to room temperature, diluted with water and extracted with dichloromethane. The organic phase is dried over Na$_2$SO$_4$, filtered, and concentrated to give a residue, which is purified by silica gel chromatography (elution with hexanes-ethyl acetate mixtures) to give 3-(6-cyclopropyl-1,2,3,4-tetrahydro-naphthalen-1-yl)-3H-imidazole-4-carboxylic acid isopropyl ester; MS: (ESI) m/z 325.2 (M+H)$^+$. The HCl salt of the title compound can be prepared by dissolution in diethyl ether followed by treatment with an excess of 1N HCl in diethyl ether. The resulting heterogeneous solution is concentrated to furnish the HCl salt of 3-(6-cyclopropyl-1,2,3,4-tetrahydro-naphthalen-1-yl)-3H-imidazole-4-carboxylic acid isopropyl ester; $^1$H NMR (400 MHz, MeOD) δ ppm 0.71-0.75 (m, 2 H), 1.00-1.05 (m, 2 H), 1.43 (d, J=6.3 Hz, 3 H), 1.46 (d, J=6.3 Hz, 3 H), 1.65-1.76 (m, 1 H), 1.87-1.98 (m, 2 H), 2.24-2.39 (m, 2 H), 2.87 (ddd, J=16.9, 9.3, 5.3 Hz, 1 H), 3.00 (dt, J=16.9, 5.0 Hz, 1 H), 5.34 (sept, J=6.3 Hz, 1 H), 6.51 (t, J=4.8 Hz, 1 H), 6.98

(dd, J=9.3, 1.2 Hz, 1 H), 7.03 (d, J=9.3 Hz, 2 H), 8.32 (d, J=1.5 Hz, 1 H), 8.51 (d, J=1.0 Hz, 1 H).

Example 50 a) 3-(1,2,3,4-Tetrahydro-naphthalen-1-yl)-3H-imidazole-4-carboxylic acid

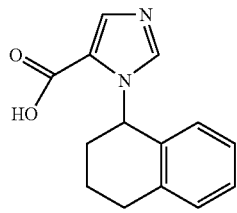 [SMILES: O=C(O)c1cncn1C1CCCc2ccccc21]

To a solution of 3-(1,2,3,4-tetrahydro-naphthalen-1-yl)-3H-imidazole-4-carboxylic acid methyl ester, which can be prepared as described in Example 2, (0.510 g, 1.990 mmol) in ethanol (20 mL) is added aqueous 4M LiOH (5 mL, 20 mmol) causing an immediate precipitate to form. After 3 hours, the mixture is evaporated to dryness, re-dissolved in a minimum amount of water, and the pH is adjusted to 6 with aqueous 2M HCl, causing a precipitate to form. The reaction is cooled to 0° C. and allowed to stand for 30 minutes. The precipitate is then filtered off and washed with cold phosphate buffer (pH 6). Upon standing, a solid precipitates out of the phosphate buffer which is filtered and combined with the initial precipitate to yield, upon drying under high vacuum, 3-(1,2,3,4-tetrahydro-naphthalen-1-yl)-3H-imidazole-4-carboxylic acid; MS: (ESI) m/z 243.2 (M+H)$^+$; $^1$H NMR (400 MHz, MeOD) δ ppm 1.77-1.96 (m, 2 H), 2.21-2.36 (m, 2 H), 2.87-2.95 (m, 1 H), 3.05 (dt, J=16.9, 5.8 Hz, 1 H), 6.57 (t, J=5.6 Hz, 1 H), 7.01 (d, J=7.8 Hz, 1 H), 7.18-7.26 (m, 1 H), 7.26-7.36 (m, 2 H), 7.55 (s, 1 H), 7.79 (d, J=1.0 Hz, 1 H).

Example 51 a) 3-(5-Hydroxymethyl-imidazol-1-yl)-2,2-dimethyl-indan-1-one O-ethyl-oxime

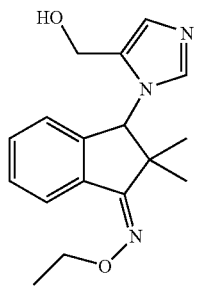 [SMILES: CCO/N=C1\c2ccccc2C(n2cncc2CO)C1(C)C]

To a solution of 3-[5-(tert-butyl-dimethyl-silanyloxymethyl)-imidazol-1-yl]-2,2-dimethyl-indan-1-one (1.07 g, 2.9 mmol), which can be prepared as described in Example 21, in ethanol (30 mL) is added pyridine (4.7 mL, 58 mmol) followed by the HCl salt of O-ethyl-hydroxylamine (850 mg, 8.7 mmol). The reaction is then heated at reflux for 1 hour, at which time it is cooled to room temperature and concentrated to near dryness. The resulting residue is diluted with ethyl acetate and washed with saturated aqueous NaHCO$_3$. The organic layer is dried with Na$_2$SO$_4$, filtered, and concentrated. The resulting residue is taken directly to the next step, wherein it is dissolved in THF (30 mL) and then treated with a 1N solution of tetrabutylammonium fluoride in THF (5.0 mL, 5.0 mmol). The reaction is permitted to stir for 1 hour, at which time it is diluted with saturated aqueous NH$_4$Cl and ethyl acetate. The layers are separated and the aqueous layer is extracted an additional two times with ethyl acetate. The combined organic layers are dried with Na$_2$SO$_4$, filtered and concentrated. The resulting residue is purified by silica gel flash chromatography (methanol-dichloromethane, 0:1 to 1:20) to furnish 3-(5-hydroxymethyl-imidazol-1-yl)-2,2-dimethyl-indan-1-one O-ethyl-oxime as a mixture of geometric isomers; HRMS: (ESI) m/z 300.1710 [(M+H)$^+$: Calcd for C$_{17}$H$_{21}$N$_3$O$_2$: 300.1712]; ~1:1.25 isomeric mixture. Major: $^1$H NMR (400 MHz, CDCl$_3$) δ ppm 1.08 (s, 3 H), 1.32 (t, J=7.1 Hz, 3 H), 1.58 (s, 3 H), 4.20 (q, J=7.0 Hz, 2 H), 4.68-4.82 (m, 2 H), 5.59 (s, 1 H), 6.87-7.00 (m, 2 H), 7.17 (d, J=7.3 Hz, 1 H), 7.34-7.52 (m, 2 H), 7.71-7.79 (m, 1 H), Minor: $^1$H NMR (400 MHz, CDCl$_3$) δ ppm 0.92 (s, 3 H), 1.38 (t, J=7.1 Hz, 3 H), 1.44 (s, 3 H), 4.27 (q, J=7.1 Hz, 2 H), 4.69-4.82 (m, 2 H), 5.60 (s, 1 H), 6.88-7.01 (m, 2 H), 7.28-7.30 (m, 1 H), 7.34-7.50 (m, 2 H), 8.37-8.45 (m, 1 H).

Example 52 a) 5-[3-(2,2-Dimethyl-indan-1-yl)-3H-imidazol-4-yl]-3-methyl-[1,2,4]oxadiazole

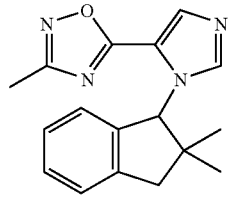

To a solution N-hydroxy-acetamidine (137 mg, 1.85 mmol) in THF (5 mL) is added 4 angstrom molecular sieves (500 mg) followed by a 60% oil dispersion of NaH (80 mg, 2.0 mmol). The heterogeneous mixture is heated at 60° C. for 1 hour at which time a solution of 3-(2,2-dimethyl-indan-1-yl)-3H-imidazole-4-carboxylic acid methyl ester, which can be prepared as described in Example 10, (200 mg, 0.74 mmol) in THF (5 mL) is added. The reaction is heated at reflux for 1.5 hours, at which time the reaction is cooled to 0° C. and quenched with water. The reaction is diluted with dichloromethane and filtered. The layers are separated and the aqueous layer is extracted three times with dichloromethane. The organic layers are combined, dried with Na$_2$SO$_4$, filtered, and concentrated. The resulting residue is purified by silica gel flash chromatography (ethyl acetate-dichloromethane, 0:1 to 1:9) to afford 5-[3-(2,2-Dimethyl-indan-1-yl)-3H-imidazol-4-yl]-3-methyl-[1,2,4]oxadiazole; HRMS: (ESI) m/z 259.1566 [(M+H)$^+$: Calcd for C$_{17}$H$_{19}$N$_4$O: 295.1559]; $^1$H NMR (400 MHz, CDCl$_3$) δ ppm 0.75 (s, 3 H), 1.27 (s, 3 H), 2.50 (s, 3 H), 2.71-3.10 (m, 2 H), 6.37 (s, 1 H), 7.17 (s, 1 H), 7.23-7.43 (m, 4 H), 7.98 (s, 1 H).

b) (R)- and (S)-5-[3-(2,2-Dimethyl-indan-1-yl)-3H-imidazol-4-yl]-3-methyl-[1,2,4]oxadiazole Resolution of the enantiomers of the title compound is achieved by chiral HPLC using a ChiralPak AS-H column with 7:3 heptane:ethanol to give two isomers with $t_r$=4.8 min and $t_r$=6.5 min.

Example 53 a) 3-(2-Oxo-2lambda*4*-isothiochroman-4-yl)-3H-imidazole-4-carboxylic acid isopropyl ester

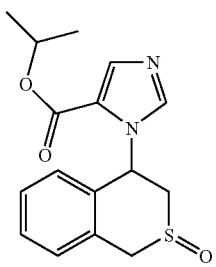 [SMILES: CC(C)OC(=O)c1cncn1C1CS(=O)Cc2ccccc21]

To a solution of 3-isothiochroman-4-yl-3H-imidazole-4-carboxylic acid isopropyl ester, which can be prepared as described in Example 1, (100 mg, 0.33 mmol) in acetic acid (3 mL), is added a 50% wt solution of aqueous hydrogen peroxide (62 □L, 0.92 mmol). The reaction is then heated to 50° C. for 1 hour. The reaction mixture is cooled to room temperature and diluted with ethyl acetate and saturated aqueous NaHCO$_3$. The layers are separated, and the organic layer is dried over Na$_2$SO$_4$, filtered, and concentrated. The resulting residue is purified by silica gel flash chromatography (ethyl acetate-dichloromethane, 0:1 to 4:1) to afford a diastereomeric mixture of 3-(2-oxo-2lambda*4*-isothiochroman-4-yl)-3H-imidazole-4-carboxylic acid isopropyl ester; MS: (ESI) m/z 319 (M+H)$^+$; Major: $^1$H NMR (400 MHz, CDCl$_3$) δ ppm 1.21 (d, J=6.3 Hz, 3 H), 1.28 (d, J=6.3 Hz, 3 H), 3.45-3.54 (m, 1 H), 3.65-3.77 (m, 1 H), 4.06 (d, J=15.2 Hz, 1 H), 4.38 (d, J=15.7 Hz, 1 H), 4.99-5.10 (m, 1 H), 6.58-6.66 (m, 1 H), 6.73 (d, J=7.6 Hz, 1 H), 7.19-7.40 (m, 3 H), 7.56 (s, 1 H), 7.81 (s, 1 H), Minor: $^1$H NMR (400 MHz, CDCl$_3$) δ ppm 1.30-1.37 (m, 6 H), 3.36-3.44 (m, 1 H), 3.66-3.76 (m, 1 H), 4.01-4.06 (m, 1 H), 4.31 (d, J=14.9 Hz, 1 H), 5.12-5.21 (m, 1 H), 6.56-6.66 (m, 1 H), 6.85 (d, J=7.8 Hz, 1 H), 7.20-7.40 (m, 3 H), 7.66 (s, 1 H), 7.79 (s, 1 H). The HCl salt of the title compound can be prepared by dissolution in diethyl ether followed by treatment with an excess of 1N HCl in diethyl ether. The resulting heterogeneous solution is concentrated to furnish the HCl salt of 3-(2-oxo-2lambda*4*-isothiochroman-4-yl)-3H-imidazole-4-carboxylic acid isopropyl ester.

Example 54 a) 1-(1,1-Dioxo-thiochroman-4-yl)-1H-imidazole

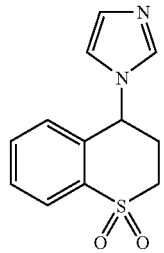 [SMILES: O=S1(=O)CCC(n2ccnc2)c2ccccc21]

To a solution of 1-thiochroman-4-yl-1H-imidazole, which can be prepared as described in Example 16, (130 mg, 0.60 mmol) in methanol (3 mL) at 0° C. is added dropwise a solution of Oxone® (excess) in water (3 mL). The reaction mixture is stirred overnight at room temperature. The reaction is then concentrated an the resulting residue is purified by silica gel flash chromatography (0:1 to 1:19 methanol-dichloromethane), to afford 1-(1,1-dioxo-thiochroman-4-yl)-1H-imidazole; MS: (ESI) m/z 249.1 (M+H); $^1$H NMR (400 MHz, MeOD) δ ppm 2.83-3.13 (m, 2 H), 3.42-3.65 (m, 1 H), 3.64-3.82 (m, 1 H), 6.18 (t, J=7.1 Hz, 1 H), 7.14 (d, J=7.6 Hz, 1 H), 7.49-7.78 (m, 4 H), 8.02 (d, J=8.0 Hz, 1 H), 9.06 (s, 1 H).

Example 55 a) 1-(2,2-Dimethyl-indan-1-yl)-5-isopropyl-1H-imidazole

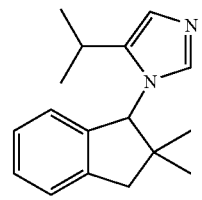 [SMILES: CC(C)c1cncn1C1c2ccccc2CC1(C)C]

To a solution of 2-[3-(2,2-dimethyl-indan-1-yl)-3H-imidazol-4-yl]-propan-2-ol, which can be prepared as described in Example 22, (180 mg, 0.665 mmol) in pyridine (3 mL) is added 4-dimethylaminopyridine (50 mg, 0.4 mmol) and methanesulfonyl chloride (0.52 mL, 0.665 mmol). The reaction is permitted to stir for 90 minutes, at which time it is diluted with ethyl acetate and saturated aqueous NaHCO$_3$. The layers are separated and the organic layer is dried with Na$_2$SO$_4$, filtered, and concentrated. The resulting residue is dissolved in ethanol (3 mL) and charged with 5% palladium on carbon (283 mg, 0.135 mmol). The reaction is placed under a hydrogen atmosphere (balloon pressure) for 1.5 hours, at which time it is filtered and the eluent concentrated. The resulting residue is purified by silica gel flash chromatography (ethyl acetate-dichloromethane, 0:1 to 1:9) to provide 1-(2,2-dimethyl-indan-1-yl)-5-isopropyl-1H-imidazole. HRMS: (ESI) m/z 255.1870 [(M+H)$^+$: Calcd for C$_{17}$H$_{23}$N$_2$: 255.1861]; The HCl salt of the title compound can be prepared by dissolution in diethyl ether followed by treatment with an excess of 1N HCl in diethyl ether. The resulting heterogeneous solution is concentrated to furnish the HCl salt of 1-(2,2-dimethyl-indan-1-yl)-5-isopropyl-1H-imidazole; $^1$H NMR (400 MHz, CD$_3$OD) δ ppm 0.84 (s, 3 H), 1.33 (s, 3 H), 1.42 (d, J=6.6 Hz, 3 H), 1.49 (d, J=6.8 Hz, 3 H), 2.84-3.18 (m, 2 H), 3.23-3.32 (m, 1 H), 5.58 (s, 1 H), 7.24-7.48 (m, 4 H), 7.51 (s, 1 H), 8.19 (d, J=1.3 Hz, 1 H).

Example 56 a) 1-Cyclopropyl-3-[3-(1,2,3,4-tetrahydro-naphthalen-1-yl)-3H-imidazol-4-yl]-urea

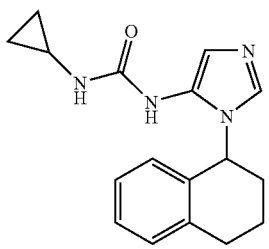 [SMILES: O=C(Nc1cncn1C1CCCc2ccccc21)NC1CC1]

The title compound can be prepared in 3 steps from 1,2,3,4-tetrahydro-naphthalen-1-ol (CAS #529-33-9) as depicted in the scheme below:

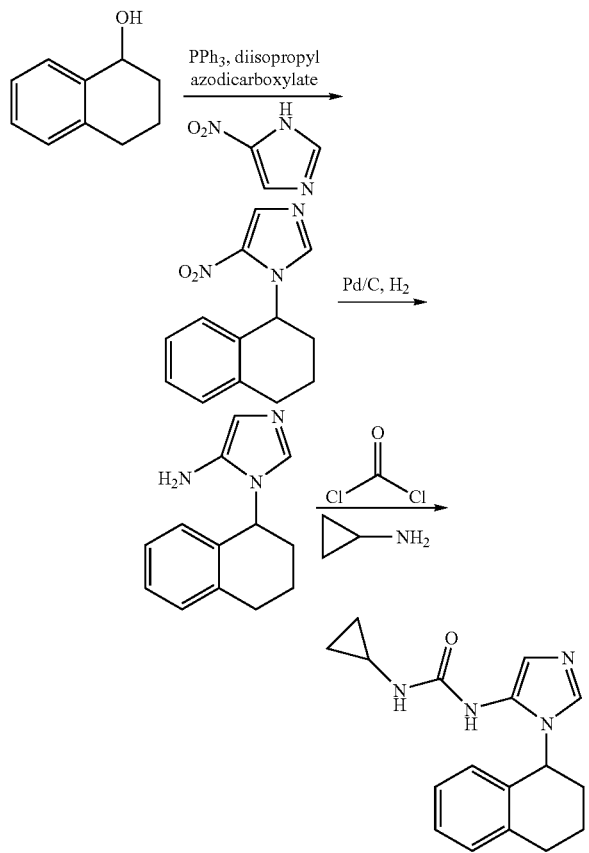

In the first step a modified Mitsunobu reaction employing 5-nitro-1H-imidazole (CAS #3034-38-6) can be preformed as described in Example 1. The resulting 5-nitro-1(1,2,3,4-tetrahydro-naphthalen-1-yl)-1H-imidazole, can then be reduced via the employment of palladium on carbon under a hydrogen atmosphere. The resulting amine can undergo treatment with phosgene followed by the addition of cyclopropylamine to afford 1-cyclopropyl-3-[3-(1,2,3,4-tetrahydro-naphthalen-1-yl)-3H-imidazol-4-yl]-urea; MS: (ESI) m/z 297.1 (M+H)$^+$; $^1$H NMR (400 MHz, CDCl$_3$) δ ppm 0.46-0.57 (m, 2 H), 0.68-0.77 (m, 2 H), 1.78-2.29 (m, 4 H), 2.49-2.60 (m, 1 H), 2.79-3.01 (m, 2 H), 5.17-5.31 (m, 1 H), 5.34-5.43 (m, 1 H), 6.33-6.43 (m, 1 H), 6.85 (d, J=7.6 Hz, 1 H), 7.01 (s, 1 H), 7.13 (t, J=7.5 Hz, 1 H), 7.17-7.26 (m, 3 H).

The Following Compounds can be Prepared in a Similar Fashion as Example 56

Morpholine-4-carboxylic acid [3-(1,2,3,4-tetrahydro-naphthalen-1-yl)-3H-imidazol-4-yl]-amide

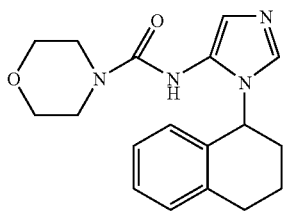 [SMILES: O=C(Nc1cncn1C1CCCc2ccccc21)N1CCOCC1]

1H NMR (400 MHz, CDCl$_3$) of the free base: δ ppm 1.72-2.15 (m, 5 H), 2.19-2.32 (m, 1 H), 2.77-2.99 (m, 2 H), 3.25-3.42 (m, 4 H), 3.63-3.72 (m, 4 H), 5.31-5.42 (m, 1 H), 6.28 (br. s., 1 H), 6.93 (d, J=1.01 Hz, 1 H), 6.99-7.05 (m, 1 H), 7.10-7.26 (m, 4 H); MS: (ESI) m/z 327.1 (M+H)$^+$.

Example 57 a) 3-[5-(tert-Butyl-dimethyl-silanyloxymethyl)-imidazol-1-yl]-6-chloro-2,2-dimethyl-indan-1-ol

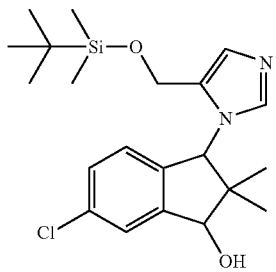 [SMILES: CC1(C)C(O)c2cc(Cl)ccc2C1n1cncc1CO[Si](C)(C)C(C)(C)C]

To a solution of 3-(5-chloro-2,2-dimethyl-3-oxo-indan-1-yl)-3H-imidazole-4-carboxylic acid methyl ester [MS: (ESI) m/z 319.1 (M+H)$^+$], which can be prepared starting from 5-chloro-indan-one (CAS#42348-86-7) in a fashion analogous to Example 13, (740 mg, 2.3 mmol) in THF (25 mL) at 0° C. is added lithium aluminum hydride (140 mg, 3.68 mmol) in three portions. The reaction is permitted to stir for 30 minutes, at which time it is quenched at 0° C. by the consecutive addition of 9:1 THF/H$_2$O (2.0 mL), 2M aqueous NaOH (2.3 mL), and H$_2$O (1.5 mL). The reaction is warmed to room temperature and diluted with THF (15 mL). After addition of MgSO$_4$ (2.2 g), the heterogeneous mixture is stirred for 15 min and then filtered through a pad of Celite®. The pad of Celite® is washed with ethyl acetate and the combined filtrate is concentrated. The resulting residue is dissolved in DMF (25 mL) and cooled to 0° C. To the resulting solution is added imidazole (290 mg, 4.26 mmol) followed by TBSCI (425 mg, 2.8 mmol). The reaction is placed at room temperature and permitted to stir for 2.5 hours. The reaction is quenched with ethanol, concentrated to near dryness and diluted with saturated aqueous $NaHCO_3$ and ethyl acetate. The layers are separated and the aqueous layer is extracted with ethyl acetate. The organic layers are combined, dried with $Na_2SO_4$, filtered, and concentrated. The resulting residue is purified by silica gel flash chromatography (ethyl acetate-heptane, 1:4 to 1:0) to provide 3-[5-(tert-butyl-dimethyl-silanyloxymethyl)-imidazol-1-yl]-6-chloro-2,2-dimethyl-indan-1-ol as a diastereomeric mixture; MS: (ESI) m/z 407.2 $(M+H)^+$.

b) (R) and (S)-6-Chloro-3-(5-hydroxymethyl-imidazol-1-yl)-2,2-dimethyl-indan-1-one

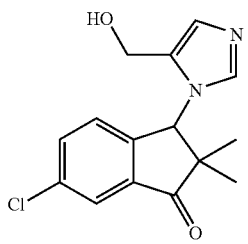 [SMILES: CC1(C)C(=O)c2cc(Cl)ccc2C1n1cncc1CO]

To a solution of 3-[5-(tert-butyl-dimethyl-silanyloxymethyl)-imidazol-1-yl]-6-chloro-2,2-dimethyl-indan-1-ol (400 mg, 0.98 mmol) in 1,4-dioxane (15 mL) is added manganese(IV) oxide (2.0 g, 20 mmol). The resulting heterogeneous solution is heated at 80° C. for 60 minutes, cooled to room temperature, filtered and concentrated. The resulting residue is then dissolved in methanol, cooled to 0° C. and treated with 4 N hydrochloric acid in 1,4-dioxane (1 mL, 4.0 mmol). The reaction is placed at room temperature and permitted to stir for 3 hours, at which time the reaction is cooled to 0° C. and diluted with saturated aqueous $NaHCO_3$. The reaction mixture is then concentrated in vacuo to ca. one fourth of the original volume and diluted with ethyl acetate. The layers are separated and the aqueous layer is extracted two times with ethyl acetate. The combined organic extracts are dried over $Na_2SO_4$, filtered and concentrated. The resulting residue is purified by silica gel flash chromatography (ethanol-ethyl acetate, 0:1 to 1:10) to furnish 6-chloro-3-(5-hydroxymethyl-imidazol-1-yl)-2,2-dimethyl-indan-1-one; HRMS: (ESI) m/z 291.0891 [$(M+H)^+$: Calcd for $C_{15}H_{16}N_2O_2Cl$: 291.0900]; $^1$H NMR (400 MHz, $CDCl_3$) δ ppm 0.87 (s, 3 H), 1.44 (s, 3 H), 1.89 (br. s., 1 H), 4.70-4.92 (m, 2 H), 5.75 (s, 1 H), 6.92 (s, 1 H), 7.07 (s, 1 H), 7.41 (d, J=8.1 Hz, 1 H), 7.69 (dd, J=8.3, 2.0 Hz, 1 H), 7.87 (d, J=2.0 Hz, 1 H).

Resolution of the enantiomers of the title compound is achieved by chiral HPLC using a ChiralPak IA column with 85:15 heptane:ethanol to give two isomers with $t_r$=8.4 min and $t_r$=13.0 min.

The Following Compounds can be Prepared in a Similar Fashion as Example 57

(R)- and (S)-5-Fluoro-3-(5-hydroxymethyl-imidazol-1-yl)-2,2-dimethyl-indan-1-one

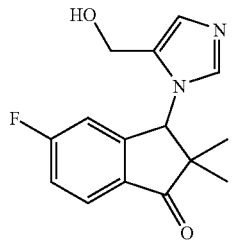 [SMILES: CC1(C)C(=O)c2ccc(F)cc2C1n1cncc1CO]

$^1$H NMR (400 MHz, $CDCl_3$) δ ppm 0.86 (s, 3 H), 1.44 (s, 3 H), 4.81 (m, 2 H), 5.87 (s, 1 H), 7.07 (s, 1 H), 7.10 (s, 1 H), 7.18 (d, J=9.1 Hz, 1 H), 7.28-7.36 (m, 1 H), 7.93 (dd, J=8.5, 5.2 Hz, 1 H); HRMS: (ESI) m/z 275.1184 [$(M+H)^+$: Calcd for $C_{15}H_{16}N_2O_2F$: 275.1196].

The resolution of the enantiomers of titled compound is achieved by chiral HPLC using a ChiralPak OD-H column with 90:10 heptane:ethanol to give the two isomers $t_r$=8.4 min and $t_r$=10.5 min.

Example 58 a) 4-Chloro-2,2-dimethyl-indan-1,3-dione

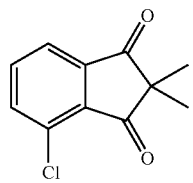

Potassium fluoride on Celite® [loading wt: 50% purchased from Sigma-Aldrich Co.] (17.4 g, ~150 mmol) is heated at 135° C. for 2 hours under vacuum (<20 torr). The solid is then permitted to cool to room temperature and placed under a nitrogen atmosphere, at which time a solution of 4-chloro-indan-1,3-dione (CAS#20926-88-9, 5.6 g, 31.0 mmol), which can be prepared as described by Smith, H.; et al. Journal of Medicinal Chemistry, 1973, 16, 1334-1339, in acetonitrile (45 mL) is added. Iodomethane (5.4 mL, 90 mmol) is then added to the mixture. The reaction is heated in a sealed vessel at 70° C. overnight. The reaction mixture is cooled to room temperature and filtered through a pad of Celite®. The eluent is concentrated and the reaction mixture is cooled to room temperature and filtered through a pad of Celite®. The resulting residue is purified by silica gel flash chromatography (ethyl acetate-heptane, 0:1 to 1:9) to furnish 4-chloro-2,2-dimethyl-indan-1,3-dione; $^1$H NMR (400 MHz, CDCl$_3$) δ ppm 1.32 (s, 6 H), 7.74-7.82 (m, 2 H), 7.91 (dd, J=7.1, 1.5 Hz, 1 H).

b) 7-Chloro-3-hydroxy-2,2-dimethyl-indan-1-one

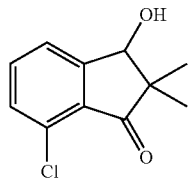

To a solution of chloro-2,2-dimethyl-indan-1,3-dione (1.82 g, 8.7 mmol) in ethanol (100 mL) at −40° C. is added NaBH$_4$ (100 mg, 2.6 mmol). The reaction is warmed to −20° C. and stirred for 1 hour. The reaction is diluted with saturated aqueous NH$_4$Cl and concentrated in vacuo to remove the volatile organics. The mixture is then diluted with ethyl acetate and the layers are separated. The aqueous layer is extracted an additional time with ethyl acetate and the organic layers are combined, dried over Na$_2$SO$_4$, filtered and concentrated to afford 7-chloro-3-hydroxy-2,2-dimethyl-indan-1-one without the need for further purification; MS: (ESI) m/z 211.15 (M+H)$^+$ c) 3-(4-Chloro-2,2-dimethyl-3-oxo-indan-1-yl)-3H-imidazole-4-carboxylic acid methyl ester

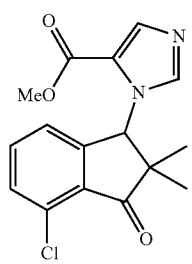 [SMILES: COC(=O)c1cncn1C1c2cccc(Cl)c2C(=O)C1(C)C]

To a solution of 7-chloro-3-hydroxy-2,2-dimethyl-indan-1-one (1.10 g, 5.24 mmol) in THF (50 mL) is added methyl 4-imidazolecarboxylate (CAS#17325-26-7, 1.0 g, 7.85 mmol), followed by triphenylphosphine (2.1 g, 7.85 mmol). The reaction is cooled to 0° C. and di-t-butyl azodicarboxylate (1.8 g, 7.85 mmol) is added. The reaction is permitted to warm to room temperature and stirred for 2 hours. The reaction mixture is then cooled to 0° C., quenched with 4 N HCl in dioxane (5 mL, 20 mmol) and stirred for 30 minutes. The reaction is concentrated to near dryness and diluted with ethyl acetate. The organic layer is extracted three times with 1 N aqueous HCl. The aqueous extracts are combined, neutralized with Na$_2$CO$_3$, and extracted three times with ethyl acetate. The organic layers are combined, dried over Na$_2$SO$_4$, filtered concentrated. The resulting residue is purified by silica gel flash chromatography (ethyl acetate-heptane, 0:1 to 1:1) to furnish 3-(4-chloro-2,2-dimethyl-3-oxo-indan-1-yl)-3H-imidazole-4-carboxylic acid methyl ester; MS: (ESI) m/z 319.0 (M+H)$^+$ d) 3-[5-(tert-Butyl-dimethyl-silanyloxymethyl)-imidazol-1-yl]-7-chloro-2,2-dimethyl-indan-1-one

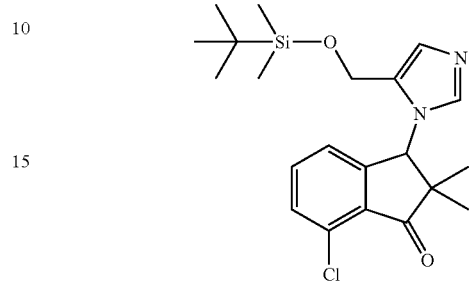

A solution of 3-(4-chloro-2,2-dimethyl-3-oxo-indan-1-yl)-3H-imidazole-4-carboxylic acid methyl ester (1.67 g, 5.24 mmol) in THF (25 mL) is added to a solution of lithium aluminum hydride (300 mg, 7.86 mmol) in THF (200 mL) at 0° C. via cannula. The reaction is permitted to stir for 60 minutes, at which time it is quenched at 0° C. by the consecutive addition of 9:1 THF/H$_2$O (4.0 mL), 2M aqueous NaOH (4.6 mL), and H$_2$O (3.0 mL). The reaction is warmed to room temperature and diluted with THF (30 mL). MgSO$_4$ (4.4 g) is then added. The resulting heterogeneous mixture is stirred for 15 min and then filtered through a pad of Celite®. The pad of Celite® is washed with ethyl acetate and the combined filtrate is concentrated. The resulting residue is dissolved in DMF (100 mL) and cooled to 0° C. To the resulting solution is added imidazole (390 mg, 5.76 mmol) followed by TBSCI (789 mg, 5.24 mmol). The reaction is placed at room temperature and permitted to stir for 2.5 hours. The reaction is quenched with ethanol, concentrated to near dryness, and diluted with saturated aqueous NaHCO$_3$ and ethyl acetate. The layers are separated and the aqueous layer is extracted with ethyl acetate. The organic layers are combined, dried with Na$_2$SO$_4$, filtered, and concentrated. The resulting residue is dissolved in 1,4-doxane (80 mL), charged with manganese(IV) oxide (9.1 g, 91 mmol), and heated to 110° C. for two hours. The reaction is then cooled to room temperature, filtered and concentrated. The resulting residue is purified by silica gel flash chromatography (ethyl acetate-dichloromethane, 0:1 to 1:2) to afford 3-[5-(tert-butyl-dimethyl-silanyloxymethyl)-imidazol-1-yl]-7-chloro-2,2-dimethyl-indan-1-one; MS: (ESI) m/z 405.1 (M+H)$^+$.

e) (R)- and (S)-7-Chloro-3-(5-hydroxymethyl-imidazol-1-yl)-2,2-dimethyl-indan-1-one

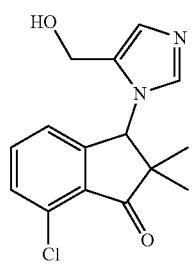 [SMILES: CC1(C)C(=O)c2c(Cl)cccc2C1n1cncc1CO]

To a solution of 3-[5-(tert-butyl-dimethyl-silanyloxymethyl)-imidazol-1-yl]-7-chloro-2,2-dimethyl-indan-1-one (650 mg, 1.6 mmol) in methanol (20 mL) is added a 1N solution of HCl in diethyl ether (15 mL, 15 mmol). The reaction is permitted to stir for 30 minutes, at which time the reaction is cooled to 0° C. and diluted with saturated aqueous NaHCO$_3$. The reaction mixture is then concentrated in vacuo to ca. one fourth of the original volume and diluted with ethyl acetate. The layers are separated and the aqueous layer is extracted two times with ethyl acetate. The combined organic extracts are dried over Na$_2$SO$_4$, filtered and concentrated. The resulting residue is purified by silica gel flash chromatography (methanol-dichloromethane, 0:1 to 1:19) to furnish 7-chloro-3-(5-hydroxymethyl-imidazol-1-yl)-2,2-dimethyl-indan-1-one; $^1$H NMR (400 MHz, CD$_3$OD) δ ppm 0.86 (s, 3 H), 1.41 (s, 3 H), 4.77 (dd, 2 H); 5.88 (s, 1 H), 7.01 (s, 1 H), 7.09 (s, 1 H), 7.45 (d, J=7.58 Hz, 1 H), 7.62 (d, J=7.83 Hz, 1 H), 7.74 (t, J=7.71 Hz, 1 H); HRMS: (ESI) m/z 291.0898 [(M+H)$^+$: Calcd for C$_{15}$H$_{16}$N$_2$O$_2$Cl: 291.0900].

The resolution of the enantiomers of titled compound is achieved by chiral HPLC using a ChiralPak OD-H column with 80:20 heptane:ethanol to give the two isomers with t$_r$=9.7 min and t$_r$=11.5 min.

Example 59 a) Acetic acid 4-chloro-3-hydroxy-2,2-dimethyl-indan-1-yl ester

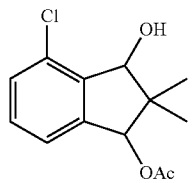 [SMILES: CC(=O)OC1c2cccc(Cl)c2C(O)C1(C)C]

To a solution of 7-chloro-3-hydroxy-2,2-dimethyl-indan-1-one, which can be prepared as described in Example 58, (287 mg, 1.36 mmol) in dichloromethane (15 mL) is added pyridine (1.1 mL, 13.6 mmol), and acetic anhydride (0.26 mL, 2.72 mmol). The reaction is permitted to stir for 1 hour and is then diluted with water and extracted twice with dichloromethane. The combined organic extracts are washed successively with 4N aqueous HCl and saturated aqueous NaHCO$_3$, dried over Na$_2$SO$_4$, filtered and concentrated. The resulting residue is then diluted with ethanol (10.0 mL) and cooled to −10° C. The solution is then charged with a solution of NaBH$_4$ (100 mg, 2.63 mmol) in ethanol (6 mL). The reaction is permitted to warm to room temperature over 1 hour, at which time additional NaBH$_4$ (50 mg, 1.31 mmol) is added. The reaction is permitted to stir for another 1.5 hours and then diluted with saturated aqueous NH$_4$Cl. The reaction mixture is concentrated to remove the organic volatiles and then extracted three times with ethyl acetate. The organic extracts are combined, dried over Na$_2$SO$_4$, filtered, and concentrated. The resulting residue is purified by silica gel flash chromatography (ethyl acetate-heptane, 0:1 to 1:2) to furnish acetic acid 4-chloro-3-hydroxy-2,2-dimethyl-indan-1-yl ester; MS: (ESI) m/z 237.17 (M−OH)$^+$ b) 3-(3-Acetoxy-7-chloro-2,2-dimethyl-indan-1-yl)-3H-imidazole-4-carboxylic acid methyl ester

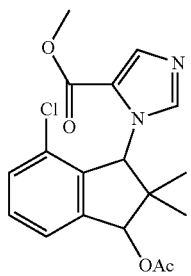 [SMILES: COC(=O)c1cncn1C1c2c(Cl)cccc2C(OC(C)=O)C1(C)C]

To a solution of acetic acid 4-chloro-3-hydroxy-2,2-dimethyl-indan-1-yl ester (1.55 g, 6.1 mmol) in THF (30 mL) is added methyl 4-imidazolecarboxylate (CAS#17325-26-7, 1.53 g, 12.2 mmol), and triphenylphosphine (3.2 g, 12.2 mmol). The reaction is cooled to 0° C. and di-t-butyl azodicarboxylate (2.81 g, 12.2 mmol) is added. The reaction is placed at room temperature and permitted to stir for ca. 12 hours and then is heated to 40° C. for 1.5 hours. The reaction mixture is cooled to 0° C., quenched with 4 N HCl in dioxane (20 mL, 80 mmol), and stirred for 30 minutes. The reaction is concentrated to near dryness and diluted with ethyl acetate. The organic layer is extracted three times with 1 N aqueous HCl. The aqueous extracts are combined, neutralized with Na$_2$CO$_3$, and extracted three times with ethyl acetate. The combined organic layers are dried with Na$_2$SO$_4$, filtered, and concentrated. The resulting residue is purified by silica gel flash chromatography (ethyl acetate-dichloromethane, 0:1 to 1:3) to furnish 3-(3-acetoxy-7-chloro-2,2-dimethyl-indan-1-yl)-3H-imidazole-4-carboxylic acid methyl ester; MS: (ESI) m/z 332.04 (M+H)$^+$.

c) 3-[5-(tert-Butyl-dimethyl-silanyloxymethyl)-imidazol-1-yl]-4-chloro-2,2-dimethyl-indan-1-one

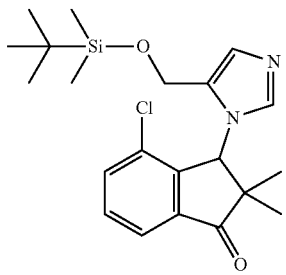 [SMILES: CC1(C)C(=O)c2cccc(Cl)c2C1n1cncc1CO[Si](C)(C)C(C)(C)C]

To a solution of 3-(3-acetoxy-7-chloro-2,2-dimethyl-indan-1-yl)-3H-imidazole-4-carboxylic acid methyl ester (1.4 g, 3.86 mol) in THF (30 mL) at 0° C. is added lithium aluminum hydride (290 mg, 7.71 mmol) in three portions. The reaction is permitted to stir for 30 minutes, at which time it is quenched at 0° C. by the consecutive addition of 9:1 THF/H$_2$O (4.0 mL), 2M aqueous NaOH (4.5 mL), and H$_2$O (3.0 mL). The reaction is warmed to room temperature and diluted with THF (30 mL). MgSO$_4$ (4.5 g) is then added and the resulting heterogeneous mixture is stirred for 15 min and then filtered through a pad of Celite®. The pad of Celite® is washed with ethyl acetate and the combined filtrate is concentrated. The resulting residue is dissolved in DMF (30 mL) and cooled to 0° C. To the resulting solution is added imidazole (350 mg, 5.1 mmol) followed by TBSCI (640 mg, 4.24 mmol). The reaction is placed at room temperature and permitted to stir for ca. 15 hours. The reaction is then quenched with ethanol, concentrated to near dryness, and diluted with saturated aqueous NaHCO$_3$ and ethyl acetate. The layers are separated and the aqueous layer is extracted with ethyl acetate. The organic layers are combined, dried with Na$_2$SO$_4$, filtered, and concentrated. The resulting residue is dissolved in 1,4-dioxane (30 mL) and manganese(IV) oxide (7.5 g, 75 mmol) is added. The resulting heterogeneous solution is heated at 110° C. for 90 minutes, cooled to room temperature, filtered and concentrated. The resulting residue is purified by silica gel flash chromatography (ethyl acetate-heptane, 0:1 to 1:4) to afford 3-[5-(tert-butyl-dimethyl-silanyloxymethyl)-imidazol-1-yl]-4-chloro-2,2-dimethyl-indan-1-one; MS: (ESI) m/z 405.11 (M+H)$^+$.

d) (R)- and (S)-4-Chloro-3-(5-hydroxymethyl-imidazol-1-yl)-2,2-dimethyl-indan-1-one

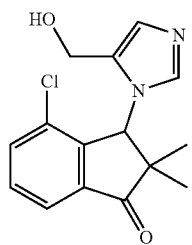 [SMILES: CC1(C)C(=O)c2cccc(Cl)c2C1n1cncc1CO]

To a solution of 3-[5-(tert-butyl-dimethyl-silanyloxymethyl)-imidazol-1-yl]-4-chloro-2,2-dimethyl-indan-1-one (2.4 g, 5.9 mmol) in methanol (40 mL) is added a 4N solution of HCl in 1,4-dioxane (9 mL, 36 mmol). The reaction is permitted to stir for 30 minutes, at which time the reaction is cooled to 0° C. and diluted with saturated aqueous NaHCO$_3$. The reaction mixture is then concentrated in vacuo to ca. one fourth of the original volume and diluted with ethyl acetate. The layers are separated and the aqueous layer is extracted two times with ethyl acetate. The combined organic extracts are dried over Na$_2$SO$_4$, filtered and concentrated. The resulting residue is purified by silica gel flash chromatography (methanol-dichloromethane, 0:1 to 1:19) to furnish 4-chloro-3-(5-hydroxymethyl-imidazol-1-yl)-2,2-dimethyl-indan-1-one; HRMS: (ESI) m/z 291.0909 [(M+H)$^+$: Calcd for C$_{15}$H$_{16}$N$_2$O$_2$Cl: 291.0909]; $^1$H NMR (400 MHz, CD$_3$OD) δ ppm 0.91 (s, 3 H), 1.40 (s, 3 H), 4.80 (d, J=4.29 Hz, 2 H), 5.88 (s, 1 H), 6.89 (s, 1 H), 6.97 (s, 1 H), 7.69 (t, J=7.71 Hz, 1 H), 7.79-7.87 (m, 2 H).

Resolution of the enantiomers of the title compound is achieved by chiral HPLC using a ChiralPak IA column with 90:10 heptane:ethanol to give the two isomers with t$_r$=12.0 min and t$_r$=18.2 min.

The compounds listed in Tables 2-8 have been described and characterized in the corresponding references, but the biological properties as aldosterone synthase inhibitors are novel.

TABLE 2

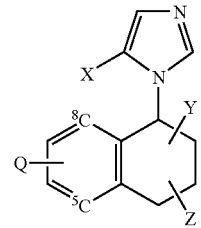

| # | X | Y | Z | Q | Exemplified |
|---|---|---|---|---|---|
| 1 | COOCH3 | 2-CH2CH3 | H | H | U.S. Pat. No. 5246915 |
| 2 | COOCH3 | 2-(CH2)4-2 | | H | U.S. Pat. No. 5246915 |
| 3 | COOCH3 | 2-CH2CH3 | 2-CH2CH3 | H | U.S. Pat. No. 5246915 |
| 4 | COO—CH2CH3 | 2-CH3 | 2-CH3 | H | U.S. Pat. No. 5246915 |
| 5 | CHF2 | 2-CH3 | 2-CH3 | H | U.S. Pat. No. 4994103 |
| 6 | COOCH3 | 2-CH3 | 2-CH3 | 7-OCH3 | EP0287512 |
| 7 | COOCH3 | H | H | 5-NO2 | U.S. Pat. No. 5246915 |

TABLE 3

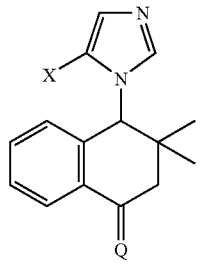

| # | X | Q | Exemplified |
|---|---|---|---|
| 1 | COOCH3 | O | U.S. Pat. No. 4898607 EP0305330 |
| 2 | COOCH3 | N—OCH3 | EP0305330 |
| 3 | COOCH3 | N—O-Benzyl | EP0305330 |

TABLE 4

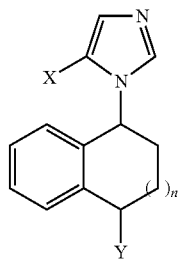

| # | X | Y | n | Exemplified |
|---|---|---|---|---|
| 1 | COOCH3 | OH | 1 | U.S. Pat. No. 4898607 EP0305330 |
| 2 | COOCH3 | H | 2 | U.S. Pat. No. 5246915 |

TABLE 5

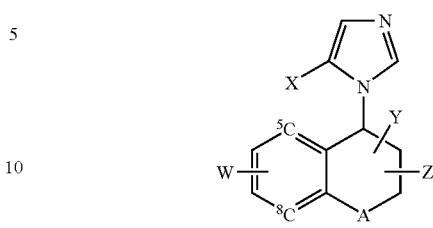

| # | A | X | Y | Z | W | Exemplified |
|---|---|---|---|---|---|---|
| 1 | O | COOCH3 | 2-CH3 | 2-CH3 | H | EP0234656 |
| 2 | O | COOCH3 | 2-CH3 | H | H | EP0234656 |
| 3 | O | COOCH3 | 3-(CH2)4-3 |  | 6-OCH3 | EP0234656 |
| 4 | O | COOCH3 | 3-(CH2)4-3 |  | 7-CH3 | EP0234656 |

TABLE 6

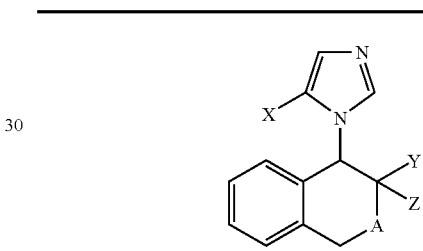

| # | A | X | Y | Z | Exemplified |
|---|---|---|---|---|---|
| 1 | S | COOCH3 | CH3 | CH3 | U.S. Pat. No. 4904300 |

TABLE 7

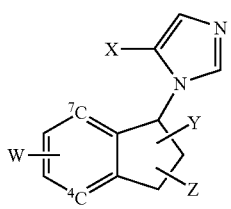

| # | X | Y | Z | W | Exemplified |
|---|---|---|---|---|---|
| 1 | COOCH2CH3 | 2-CH3 | 2-CH3 | H | U.S. Pat. No. 5246915 |
| 2 | COO-Ph | 2-CH3 | 2-CH3 | H | EP0277384 |
| 3 | COOCH3 | 2-CH2CH3 | 2-CH2CH3 | H | U.S. Pat. No. 5246915 |
| 4 | COOCH3 | 2-Benzyl | 2-Benzyl | H | U.S. Pat. No. 5246915 |
| 5 | COOCH3 | 2-CH3 | H | H | U.S. Pat. No. 5246915 |
| 6 | COOCH3 | 2-CH3 | H | 7-F | U.S. Pat. No. 5246915 |
| 7 | COOCH3 | 2-CH3 | 2-CH3 | 4-F | U.S. Pat. No. 5246915 |
| 8 | COOCH3 | 2-CH3 | 2-CH3 | 5-F | U.S. Pat. No. 5246915 |
| 9 | COOCH3 | 2-CH3 | 2-CH3 | 6-OCH3 | U.S. Pat. No. 5246915 |
| 10 | CO—NH—CH3 | 2-(CH2)4-2 |  | H | EP0277384 |
| 11 | CO—NH—CH2CH2OH | 2-CH3 | 2-CH3 | H | EP0277384 |

TABLE 7-continued

|  | | | | | |
|---|---|---|---|---|---|
| # | X | Y | Z | W | Exemplified |
| 12 | (morpholinyl carbonyl structure) | 2-CH3 | 2-CH3 | H | EP0277384 |
| 13 | CN | 2-CH3 | 2-CH3 | H | U.S. Pat. No. 4921955 |
| 14 | (oxadiazole-CF3 structure) | 2-CH3 | 2-CH3 | H | EP0277384 |
| 15 | CHF2 | 2-CH3 | 2-CH3 | H | EP0289066 |

TABLE 8

| # | X | Y | Z | W | Exemplified |
|---|---|---|---|---|---|
| 1 | CO—NH—CH3 | CH3 | CH3 | O | U.S. Pat. No. 4898607 |
| 2 | COOCH3 | CH3 | CH3 | N—OCH3 | U.S. Pat. No. 4898607 |

We claim:

1. A compound of formula (I):

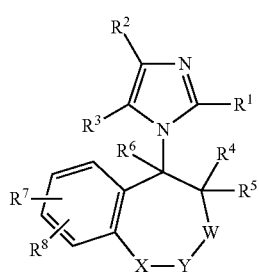

wherein
$R^1$, $R^2$ and $R^6$ are hydrogen;
$R^3$ ($C_1$-$C_7$) alkyl that is optionally substituted by one to four substituents selected from hydroxy, halogen, ($C_1$-$C_7$) alkyl, ($C_1$-$C_7$) alkoxy, ($C_6$-$C_{10}$) aryloxy, 5-7 membered heterocycle, or 5-7 membered heteroaryl;
$R^4$ and $R^5$ are independently hydrogen, ($C_1$-$C_7$) alkyl, ($C_6$-$C_{10}$) aryl, ($C_6$-$C_{10}$) aryl-($C_1$-$C_7$) alkyl; or
$R^4$ and $R^5$ taken together with the carbon atom to which they attach, form a 3-9 membered ring;
$R^7$ and $R^8$ are independently hydrogen, ($C_1$-$C_7$) alkoxy, ($C_1$-$C_7$) alkyl, nitro, cyano, halogen, 5-7 membered heteroaryl, 5-7 membered heterocyclyl, ($C_3$-$C_7$) cycloalkyl, 5-7 membered heterocyclyl-C(O)—, ($C_5$-$C_{10}$) aryl optionally substituted by one to three substituents selected from halogen, or (Ra')(Rb')N—, wherein Ra' is hydrogen, or ($C_1$-$C_7$) alkyl, Rb' is ($C_1$-$C_7$) alkanoyl, or ($C_1$-$C_7$) alkyl-SO$_2$—; or Ra' and Rb' taken together with the attached nitrogen form a 5-7 membered ring;
X is —C(O)—, and Y and W are each a bond; or a pharmaceutically acceptable salt thereof; or an optical isomer thereof; or a mixture of optical isomers.

2. The compound of formula (I) according to claim 1, wherein $R^1$, $R^2$, $R^6$, $R^7$ and $R^8$ are hydrogen; $R^3$ is hydroxymethyl or difluoromethyl; R4 and R5 are methyl; X is —C(O)—; Y and W are a bond; or a pharmaceutically acceptable salt thereof; or an optical isomer thereof; or a mixture of optical isomers.

3. The compound of formula (I) according to claim 1, which is 3-(5-Difluoromethyl-imidazol-1-yl)-2,2-dimethyl-indan-1-one.

4. The compound of formula (I) according to claim 1, which is 3-(5-Hydroxymethyl-imidazol-1-yl)-2,2-dimethyl-indan-1-one.

5. The compound of formula I according to claim 1, which is (R)-3-(5-Hydroxymethyl-imidazol-1-yl)-2,2-dimethyl-indan-1-one; or a pharmaceutically acceptable salt thereof.

6. The compound of formula I according to claim 1, which is (S)-3-(5-Hydroxymethyl-imidazol-1-yl)-2,2-dimethyl-indan-1-one; or a pharmaceutically acceptable salt thereof.

7. A pharmaceutical composition comprising a therapeutically effective amount of a compound of formula (I) according to claim 1, and one or more pharmaceutically acceptable carriers.

8. A pharmaceutical composition comprising: a therapeutically effective amount of the compound of formula (I) according to claim 1 and one or more pharmaceutically acceptable carriers.

9. A pharmaceutical composition, comprising: a therapeutically effective amount of the compound according to claim 1 and one or more therapeutically active agents selected from angiotensin II receptor antagonist or a pharmaceutically acceptable salt thereof, HMG-Co-A reductase inhibitor or a pharmaceutically acceptable salt thereof; angiotensin converting enzyme (ACE) Inhibitor or a pharmaceutically acceptable salt thereof; calcium channel blocker (CCB) or a pharmaceutically acceptable salt thereof; dual angiotensin converting enzyme/neutral endopeptidase (ACE/NEP) inhibitor or a pharmaceutically acceptable salt thereof; endothelin antagonist or a pharmaceutically acceptable salt thereof; renin inhibitor or a pharmaceutically acceptable salt thereof; diuretic or a pharmaceutically acceptable salt thereof; an ApoA-I mimic; an anti-diabetic agent; an obesity-reducing agent; an aldosterone receptor blocker; an endothelin receptor blocker; a CETP inhibitor; an inhibitor of Na-K-ATPase membrane pump; a beta-adrenergic receptor blocker or an alpha-adrenergic receptor blocker; a neutral endopeptidase (NEP) inhibitor; and an inotropic agent.

* * * * *